United States Patent
Phillips et al.

(10) Patent No.: US 11,723,655 B2
(45) Date of Patent: *Aug. 15, 2023

(54) MAGNET-ASSISTED SUTURE GRASPERS

(71) Applicant: APPLIED MEDICAL TECHNOLOGY, INC., Brecksville, OH (US)

(72) Inventors: Grant Wesley Phillips, Richfield, OH (US); Steven Alfred Soeder, North Royalton, OH (US); George J. Picha, Brecksville, OH (US)

(73) Assignee: Applied Medical Technology, Inc., Brecksville, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/995,788

(22) PCT Filed: May 17, 2022

(86) PCT No.: PCT/US2022/029631
§ 371 (c)(1),
(2) Date: Oct. 7, 2022

(87) PCT Pub. No.: WO2022/245822
PCT Pub. Date: Nov. 24, 2022

(65) Prior Publication Data
US 2023/0119673 A1    Apr. 20, 2023

Related U.S. Application Data

(60) Provisional application No. 63/268,596, filed on Feb. 25, 2022, provisional application No. 63/189,511, filed on May 17, 2021.

(51) Int. Cl.
*A61B 17/06* (2006.01)
*A61B 17/00* (2006.01)

(52) U.S. Cl.
CPC ............... *A61B 17/06166* (2013.01); *A61B 2017/00349* (2013.01); *A61B 2017/00876* (2013.01)

(58) Field of Classification Search
CPC .... A61B 17/06166; A61B 2017/00349; A61B 2017/00876
See application file for complete search history.

(56) References Cited

U.S. PATENT DOCUMENTS 1,212,870 A    1/1917    Zolper
3,762,418 A    10/1973   Wasson
(Continued)

FOREIGN PATENT DOCUMENTS

CN    101040789 B    2/2015
EP    778004 B1      3/2003
(Continued)

OTHER PUBLICATIONS

Medacta International, "FastShuttle Suture Passer System Product Catalog," pp. 1-8 (2019), available at https://media.medacta.com/media/pc-99116sm180-rev-00.pdf, last accessed Sep. 29, 2022.
(Continued)

*Primary Examiner* — Phong Son H Dang
(74) *Attorney, Agent, or Firm* — Pearne & Gordon LLP

(57) ABSTRACT

A magnet-assisted suture grasper for grasping a magnetic suture is provided. The magnet-assisted suture grasper includes a suture retrieval needle, a retriever body, a grasper arm, and a grasper magnet. Translation of the retriever body within a needle lumen of the suture retrieval needle in a first direction causes the grasper arm to move from a first position to a second position, thereby exposing the grasper magnet and allowing contact between the grasper magnet and a magnetic suture attracted thereto. Translation of the retriever body within the needle lumen in a second direction
(Continued)

opposite the first direction causes the grasper arm to move from the second position to the first position, thereby sequestering the grasper magnet and grasping the magnetic suture within the needle lumen. Another magnet-assisted suture grasper including a handle, a stem, first and second grasper jaws, a grasper magnet, and an actuator body also is disclosed.

15 Claims, 21 Drawing Sheets

(56) References Cited

U.S. PATENT DOCUMENTS

| | | | |
|---|---|---|---|
| 4,115,015 A | 9/1978 | Torii | |
| 4,266,881 A | 5/1981 | Rubens | |
| 4,540,300 A | 9/1985 | Midorikawa | |
| 4,560,298 A | 12/1985 | Oki et al. | |
| D292,297 S | 10/1987 | Bingham | |
| 4,711,592 A | 12/1987 | Gregory | |
| 4,759,650 A | 7/1988 | Granoff | |
| 4,969,764 A | 11/1990 | Gregory | |
| 4,986,682 A | 1/1991 | Lu | |
| 5,022,773 A | 6/1991 | Waldinger et al. | |
| 5,026,190 A | 6/1991 | Longarzo | |
| D321,207 S | 10/1991 | Granoff | |
| D321,718 S | 11/1991 | Ambasz | |
| 5,131,775 A | 7/1992 | Chen | |
| 5,152,626 A | 10/1992 | Eppler | |
| 5,174,814 A | 12/1992 | Burwell et al. | |
| 5,364,365 A | 11/1994 | Wortrich | |
| 5,501,692 A | 3/1996 | Riza | |
| 5,651,626 A | 7/1997 | Chen | |
| 5,653,716 A | 8/1997 | Malo et al. | |
| 5,722,981 A | 3/1998 | Stevens | |
| 5,756,941 A | 5/1998 | Snell | |
| 5,824,009 A | 10/1998 | Fukuda et al. | |
| 5,864,490 A | 1/1999 | Van Bost | |
| 5,928,250 A | 7/1999 | Koike et al. | |
| 5,997,204 A | 12/1999 | Ducrocq | |
| 6,159,224 A | 12/2000 | Yoon | |
| 6,213,661 B1 | 4/2001 | Coon | |
| 6,318,921 B1 | 11/2001 | Craine | |
| D457,917 S | 5/2002 | Traut et al. | |
| 6,450,721 B1 | 9/2002 | D'Amico et al. | |
| 6,547,470 B2 | 4/2003 | Legg | |
| 6,551,304 B1 | 4/2003 | Whalen et al. | |
| 6,719,765 B2 | 4/2004 | Bonutti | |
| D494,218 S | 8/2004 | Anand | |
| D495,001 S | 8/2004 | Anand | |
| 6,830,402 B2 | 12/2004 | Sunatori | |
| 6,981,812 B1 | 1/2006 | Hsieh | |
| D537,878 S | 3/2007 | Anand | |
| D542,349 S | 5/2007 | Anand | |
| 7,226,229 B1 | 6/2007 | Register | |
| D548,788 S | 8/2007 | Anand | |
| 7,334,954 B1 | 2/2008 | Rentz | |
| D571,400 S | 6/2008 | Anand | |
| D574,429 S | 8/2008 | Kusaba et al. | |
| D591,136 S | 4/2009 | Cheldin | |
| D616,497 S | 5/2010 | Shiina | |
| 7,887,212 B2 | 2/2011 | Liu | |
| 7,948,648 B2 | 5/2011 | Silverbrook et al. | |
| 7,969,587 B2 | 6/2011 | Silverbrook | |
| 8,031,177 B2 | 10/2011 | Lapstun et al. | |
| 8,087,841 B2 | 1/2012 | Liu | |
| 8,094,325 B2 | 1/2012 | Silverbrook | |
| 8,182,167 B2 | 5/2012 | Liu | |
| 8,240,931 B1 | 8/2012 | Collins | |
| 8,262,241 B2 | 9/2012 | Liu | |
| 8,267,947 B2 | 9/2012 | Pantages et al. | |
| 8,287,204 B2 | 10/2012 | Silverbrook et al. | |
| 8,297,868 B2 | 10/2012 | Underwood et al. | |
| 8,360,669 B2 | 1/2013 | Underwood et al. | |
| 8,414,210 B2 | 4/2013 | Silverbrook et al. | |
| 8,632,270 B2 | 1/2014 | Liu | |
| 8,702,753 B2 | 4/2014 | Mikkaichi et al. | |
| 3,808,313 A1 | 8/2014 | Thorne et al. | |
| D725,112 S | 3/2015 | Bo | |
| 9,232,940 B2 | 1/2016 | Nason | |
| 9,351,721 B2 | 5/2016 | Auerbach et al. | |
| D758,988 S | 6/2016 | An et al. | |
| 9,474,572 B2 | 10/2016 | Lowry | |
| 9,770,238 B2 | 9/2017 | Bonutti | |
| 10,245,021 B2* | 4/2019 | Phillips | A61B 17/0469 |
| 10,299,786 B2 | 5/2019 | Levine et al. | |
| 10,335,140 B2 | 7/2019 | Baird et al. | |
| 10,343,445 B2 | 7/2019 | Wu | |
| 10,503,284 B1 | 12/2019 | Chang et al. | |
| 10,799,241 B2 | 10/2020 | Fung et al. | |
| 10,820,899 B2 | 11/2020 | George et al. | |
| 10,905,555 B2 | 2/2021 | O'Carroll et al. | |
| 10,959,734 B2 | 3/2021 | Fung et al. | |
| 10,960,705 B1 | 3/2021 | Yu | |
| 10,974,540 B1 | 4/2021 | Yu | |
| 11,020,122 B2 | 6/2021 | Miller et al. | |
| 11,026,690 B2 | 6/2021 | Fung et al. | |
| 11,207,073 B2 | 12/2021 | Clark, III et al. | |
| 11,219,447 B2 | 1/2022 | Juan et al. | |
| 11,224,435 B2 | 1/2022 | Fung et al. | |
| 11,241,904 B2 | 2/2022 | Yu | |
| 2003/0139752 A1 | 7/2003 | Pasricha et al. | |
| 2003/0216613 A1 | 11/2003 | Suzuki et al. | |
| 2004/0116963 A1 | 6/2004 | Lattouf | |
| 2005/0154403 A1 | 7/2005 | Sauer et al. | |
| 2006/0069398 A1 | 3/2006 | Suzuki et al. | |
| 2007/0118153 A1 | 5/2007 | Funamura et al. | |
| 2008/0154286 A1 | 6/2008 | Abbott et al. | |
| 2008/0243148 A1* | 10/2008 | Mikkaichi | A61B 17/0469 606/144 |
| 2008/0269783 A1 | 10/2008 | Griffith | |
| 2008/0312664 A1 | 12/2008 | Bardsley et al. | |
| 2009/0224561 A1 | 9/2009 | Jackson, III | |
| 2009/0318958 A1 | 12/2009 | Ochiai | |
| 2010/0280530 A1 | 11/2010 | Hashiba | |
| 2011/0015653 A1 | 1/2011 | Bogart et al. | |
| 2011/0112555 A1 | 5/2011 | Overes et al. | |
| 2011/0118757 A1 | 5/2011 | Pierce | |
| 2011/0144666 A1 | 6/2011 | Egle et al. | |
| 2011/0245850 A1 | 10/2011 | van der Burg et al. | |
| 2012/0277766 A1 | 11/2012 | Ferree | |
| 2013/0074849 A1 | 3/2013 | Rousseau et al. | |
| 2013/0317291 A1 | 11/2013 | Yamamoto | |
| 2015/0038976 A1 | 2/2015 | Roschak et al. | |
| 2015/0039027 A1 | 2/2015 | Broom et al. | |
| 2015/0327850 A1 | 11/2015 | Kostrzewski | |
| 2016/0324517 A1 | 11/2016 | Liu | |
| 2017/0049439 A1 | 2/2017 | Keyser et al. | |
| 2018/0049733 A1 | 2/2018 | Zhao et al. | |
| 2018/0296201 A1 | 10/2018 | Holsten et al. | |
| 2019/0076141 A1 | 3/2019 | Liu | |
| 2020/0214695 A1 | 7/2020 | Liu | |
| 2020/0360017 A1 | 11/2020 | Liu | |
| 2021/0045735 A1 | 2/2021 | Nobles et al. | |
| 2021/0059667 A1 | 3/2021 | Williams et al. | |
| 2022/0104802 A1 | 4/2022 | Liu | |
| 2022/0104803 A1* | 4/2022 | Desjardin | A61B 17/0482 |

FOREIGN PATENT DOCUMENTS

| | | |
|---|---|---|
| JP | 2006-25932 A | 2/2006 |
| JP | 2010514467 A | 5/2010 |
| WO | 2010011777 A1 | 1/2010 |
| WO | 2010129312 A2 | 11/2010 |
| WO | 2011025767 A1 | 3/2011 |
| WO | 2022245819 A1 | 11/2022 |

OTHER PUBLICATIONS

Imhoff, J., "Performing Incision-Less Hernia Repair for Kids," Michigan Health, pp. 1-5 (Feb. 17, 2020), available at https://labblog.uofmhealth.org/industry-dx/performing-incision-less-hernia-repairs-for-kids, last accessed Feb. 16, 2022.

(56) References Cited

OTHER PUBLICATIONS

Johnson, K.N., et al., "Ultrasound-Guided Pediatric Inguinal Hernia Repair," Journal of Pediatric Surgery, vol. 56, pp. 1240-1245 (epublished Mar. 11, 2021).

Young, R., "Rethinking the Simple Suture Passer," Orthopedics This Week, RRY Publications, pp. 1-8 (Apr. 29, 2016), available at https://ryortho.com/2016/04/rethinking-the-simple-suture-passer/, last accessed Apr. 25, 2022.

OrthoMed, Inc., "Suture Passer with Crochet Hook," pp. 1-2 (2022), available at https://www.orthomedinc.com/surgical-instruments/suture-passer-with-crochet-hook, last accessed Sep. 29, 2022.

Mediflex Surgical Products, "5mm Curved Maryland Dissector with Cross Serrations," pp. 1-4 (2022), available at https://mediflex.com/products/5mm-curved-maryland-dissector, last accessed Sep. 29, 2022.

CooperSurgical, Inc., "Carter-Thomason CloseSure System—Port Site Closure," pp. 1-2 (2022), available at https://www.coopersurgical.com/detail/carter-thomason-closesure-system-port-site-closure/, last accessed Sep. 29, 2022.

Endoscopy Superstore, "Arthro-Pro Suture Manipulator Grasper," Manufacturer: Advanced Endoscopy Devices, pp. 1-2 (2022), available at https://www.endoscopysuperstore.com/arthro-pro-suture-manipulator-grasper.aspx#, last accessed Sep. 29, 2022.

Arthrex, Inc., "Back Grasper with SR Handle," pp. 1-3 (2022), available at https://www.arthrex.io/products/AR-12531SR, last accessed Sep. 29, 2022.

Arthrex, Inc., "CrabClaw," pp. 1-3 (2022), available at https://www.arthrex.com/shoulder/crabclaw, last accessed Sep. 29, 2022.

Smith & Nephew, "Meniscus Mender II," pp. 1-2 (2022), available at https://www.smith-nephew.com/professional/products/all-products/meniscus-mender-ii/, last accessed Sep. 29, 2022.

DePuy Synthes, "Chia Percpasser Suture Passer," pp. 1-5 (2021), available at https://www.jnjmedtech.com/en-US/product/chia-percpasserr-suture-passer, last accessed Sep. 29, 2022.

DePuy Synthes, "Ideal Suture Shuttle," pp. 1-4 (2021), available at https://www.jnjmedtech.com/en-US/product/ideal-suture-shuttle, last accessed Sep. 29, 2022.

Arthrex, Inc., "SutureLasso," pp. 1-5 (2022), available at https://www.arthrex.com/shoulder/suturelassos, last accessed Sep. 29, 2022.

Medtronic, "Endoscopic Suturing Devices," pp. 1-3 (2022), available at https://www.medtronic.com/covidien/en-us/products/hand-instruments-ligation/endoscopic-suturing-devices.html, last accessed Sep. 29, 2022.

Zimmer Biomet, "SpeedSnare Surgical Suture Passer," pp. 1-7 (2022), available at https://www.zimmerbiomet.com/en/products-and-solutions/specialties/sports-medicine/speedsnare-surgical-suture-passer.html, last accessed Sep. 29, 2022.

Wikipedia, "Veress needle," pp. 1-3 (Apr. 3, 2022), available at https://en.wikipedia.org/wiki/Veress_needle, last accessed Sep. 29, 2022.

CooperSurgical, Inc., "Carter-Thomason II Port Site Closure System," pp. 1-2 (2022), available at https://www.coopersurgical.com/detail/carter-thomason-ii-port-site-closure-system/, last accessed Sep. 29, 2022.

Mediflex Surgical Products, "SafePass Suture Grasper," pp. 1-4 (2022), available at https://mediflex.com/products/safepass%E2%84%A2-suture-grasper-box-of-10-sterile, last accessed Sep. 29, 2022.

Zimmer Biomet, "Dragon Tongue Suture Passer," pp. 1-5 (2022), available at https://www.zimmerbiomet.com/en/products-and-solutions/specialties/sports-medicine/dragon-tongue-suture-passer.html, last accessed Sep. 29, 2022.

Medtronic, "Port-Site Closure Devices," pp. 1-4 (2022), available at https://www.medtronic.com/covidien/en-us/products/trocars-access/port-site-closure-devices.html; last accessed Sep. 20, 2022.

International Search Report and Written Opinion of PCT/US2022/029627, dated Jul. 26, 2022, pp. 1-11.

U.S. Appl. No. 17/995,779 (pending unpublished application, corresponding to WO2022245819).

Owens, J., "How Does a Clicky Pen Work?" You Tube, pp. 1-8 (2022), available at https://www.youtube.com/watch?v=Zv5Qa2kGL04, last accessed Sep. 29, 2022.

\* cited by examiner

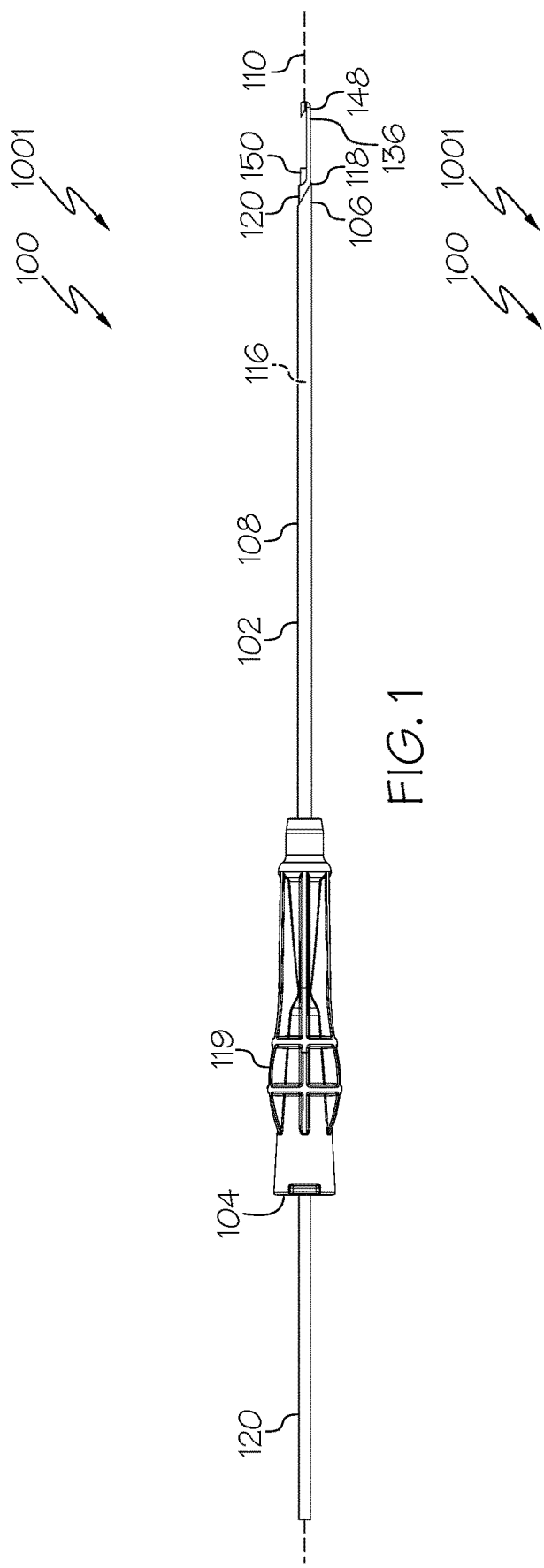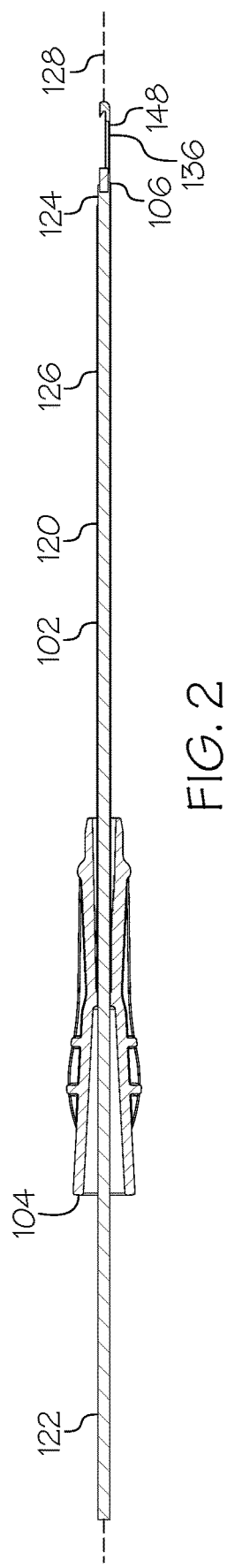

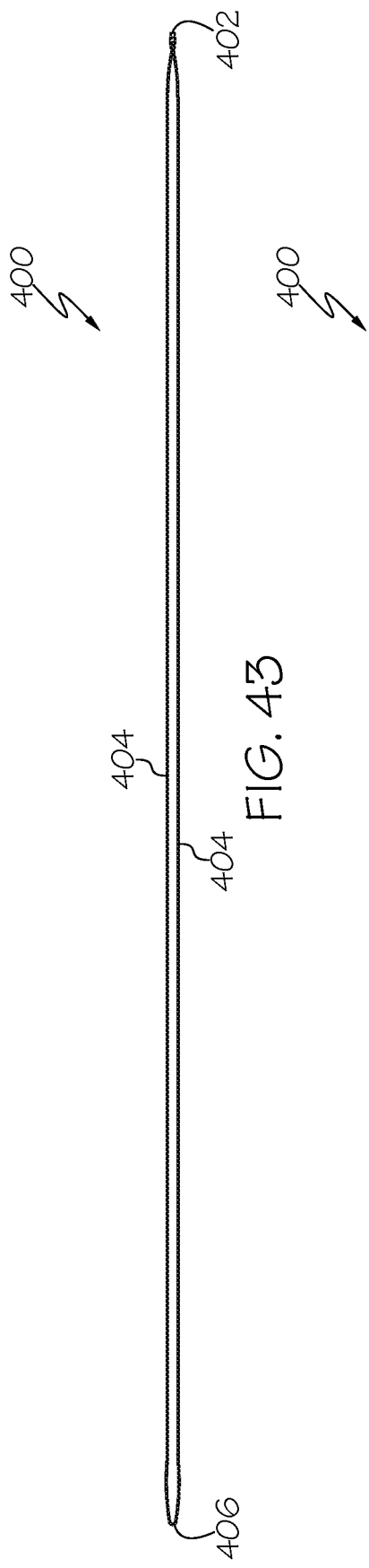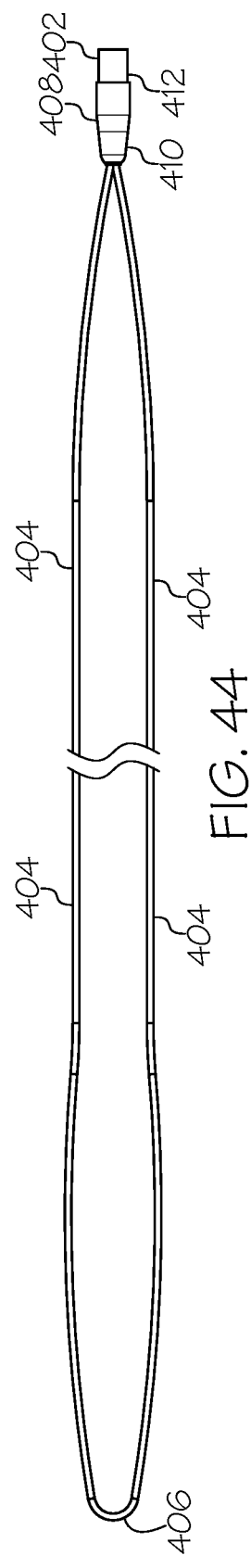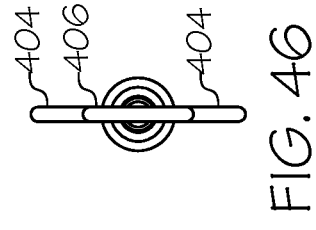
FIG. 43
FIG. 44
FIG. 45
FIG. 46

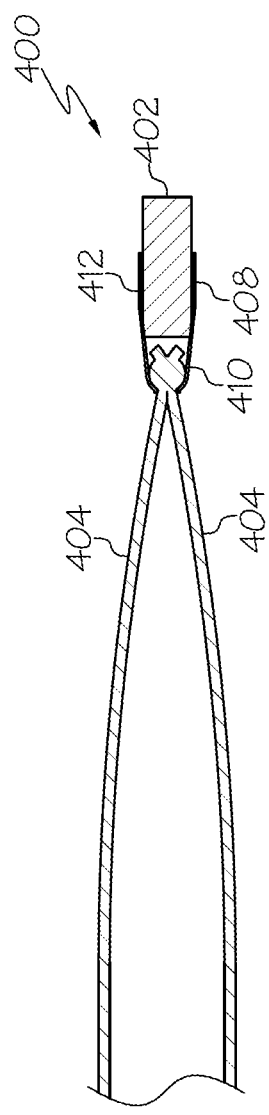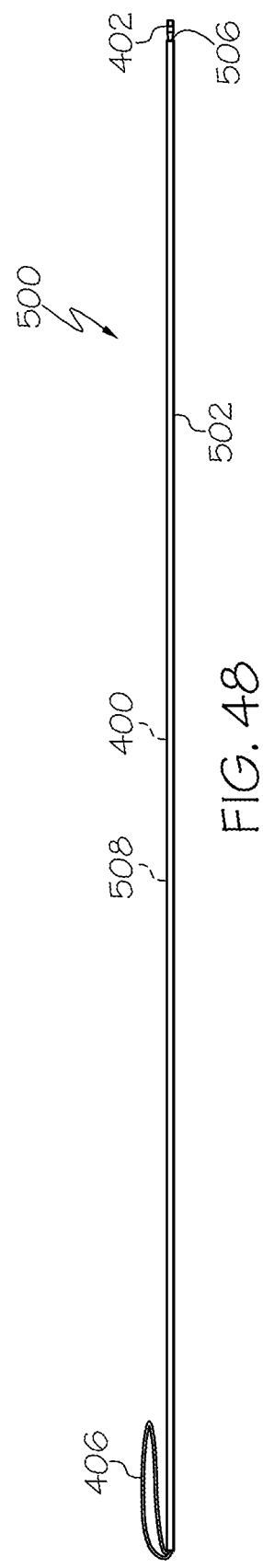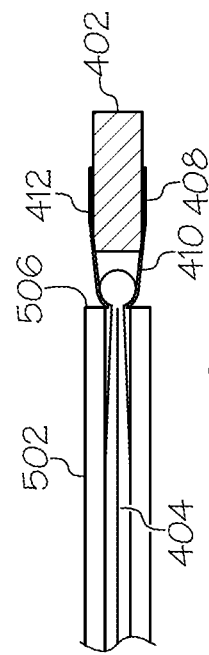

MAGNET-ASSISTED SUTURE GRASPERS

FIELD OF THE INVENTION

The invention relates to magnet-assisted suture graspers for grasping a magnetic suture, and more particularly to a magnet-assisted suture grasper for grasping a magnetic suture comprising a suture retrieval needle, a retriever body, a grasper arm, and a grasper magnet and a magnet-assisted suture grasper for grasping a magnetic suture comprising a handle, a stem, first and second grasper jaws, a grasper magnet, and an actuator body.

BACKGROUND OF THE INVENTION

Suture passing is required in many surgical procedures. A suture passer is a surgical instrument which provides a means of delivery and/or retrieval of a suture through some bodily tissue. There are many existing instruments on the market which utilize a mechanical solution to secure a suture for passing.

Increasingly, minimally invasive techniques are being employed over open surgery due to reduction in risk, faster recovery time, and generally better cosmesis. Minimally invasive techniques typically make use of a scope and specialized tools that can be inserted through existing openings of a patient (e.g., via endoscope, colonoscope, etc.) or artificially created openings of the patient (e.g., via laparoscope, arthroscope, etc.) to gain access to the targeted intracorporeal working space.

Working with indirect visualization of surgical instruments through a scope presents a significant technical challenge to the use of suture passers for retrieval. Retrieving a suture using a typical suture passer requires precise positioning and careful manipulation of the suture passer to position one or more grasping elements of the suture passer around the suture. The suture passer must be held relatively steady in position while the grasping elements are closed about the suture, capturing the suture and holding it firmly so it can be retrieved. Skillful manipulation in this manner is hampered by the fact that most scopes employ a single camera and present a two-dimensional image to the suture passer operator and thus do not provide stereoscopic imaging. The lack of stereoscopic imaging hampers the operator's ability to perceive depth, which increases the level of difficulty associated with precisely positioning the grasping elements around the suture. While three-dimensional imaging systems exist, they are expensive and to date remain relatively rare in the field.

Most existing suture passer designs utilize a multi-arm design, where two or more arms are opened and brought around a suture, then closed around the suture to capture it. The arms may be separate, creating a pincer-style grasper with jaws to grasp a suture, or they may be connected, forming a snare-type grasper forming an eye through which a suture can be threaded.

Unfortunately, regardless of the arm design, these devices require precise positioning to get the jaws of the grasper around the suture, or to thread the suture through the eye of the snare before the suture can be captured. As noted, this is difficult under indirect visualization because camera systems for indirect visualization are typically non-stereoscopic. Without a three-dimensional image, a surgeon must rely on visual cues to judge the instrument position and depth, which makes it difficult to get the instrument positioned properly. Once the instrument is in position, the surgeon then needs to hold the instrument and the suture very steady while attempting to close the grasper around the suture. The long moment arm created by the length of the instrument magnifies even very minor movements, so that a small movement can bring the two components out of alignment. Failed attempts at grasping a suture can extend procedure times and lead to frustration in the operating room.

A magnetic U-stitch suturing device intended to address these difficulties has been disclosed in U.S. Pat. No. 10,245,021. The magnetic U-stitch suturing device is made of two hypodermic needles allowing one or more sutures, at the same time, and a retrieval probe to be advanced into a cavity, such as a stomach cavity, of a patient. The one or more sutures can be magnetic sutures, each including a suture magnet, as described in U.S. Pub. No. 2021/0059667. Both the suture and retrieval probe comprise magnets of opposite polarities on their leading ends. Thus, after the suture and retrieval probe are inside the stomach cavity, the suture and retrieval probe may mate and the suture may be transferred from one hypodermic needle to the other using magnetic attraction. In doing so, the suture forms a loop through the stomach. Once removed, this loop, having two ends that are positioned outside the patient's body, can be pulled tight in order to pull the stomach wall closer to the surface of the patient's body. With the stomach wall close to the surface of the patient's body, it is easier to insert a gastrostomy device.

Unfortunately, certain procedures, such as inguinal hernia repair through high ligation of the patent processus vaginalis, require passing of a suture in a space, e.g., a peritoneal cavity, that is not sufficiently large to permit advancement of the two hypodermic needles of the magnetic U-stitch suturing device simultaneously.

Other suture instruments and/or sutures including magnets also have been disclosed. For example, U.S. Pat. No. 10,299,786 discloses a suture insertion device utilizing small gauge needles for threading one or more sutures through subcutaneous tissue. The suture insertion device can include a magnetic capture mechanism for contacting a magnetically attractive strand in transverse alignment. U.S. Pat. Nos. 6,719,765 and 9,770,238 disclose instruments for passing a medical implement through tissue with magnetic forces. U.S. Pat. No. 8,702,753 and U.S. Pub. No. 2008/0243148 disclose sutures to which magnetic anchors are attached. U.S. Pub. No. 2020/0360017 discloses a suturing apparatus in which a suture thread may be automatically passed between a needle and a transfer tube. The suturing apparatus can include electromagnetic coils to engage and release a suture from the system. U.S. Pub. No. 2020/0214695 discloses a suturing system including a forceps arm and a suture that may be magnetic to thus engage with each other. U.S. Pub. No. 2022/0104802 discloses a suturing system including a rod having a magnetic tube extending from an end thereof and a magnetic needle having an end attracted into the tube to magnetically engage therewith. U.S. Pub. No. 2021/0059667 discloses a magnetic suture that has a ferrule with a tapered region in which a knotted suture is provided and secured with an adhesive and a straight region in which a magnet is provided.

Improved suture passers that reduce the technical difficulty associated with capturing and retrieving sutures under indirect non-stereoscopic visualization are needed.

BRIEF SUMMARY OF THE INVENTION

A magnet-assisted suture grasper for grasping a magnetic suture is disclosed. The magnet-assisted suture grasper comprises: (a) a suture retrieval needle comprising a proximal end, a distal end, and a needle body extending therebetween, the needle body defining a needle body axis between the proximal and distal ends of the suture retrieval needle, the needle body having a proximal hole, a distal hole, and a needle lumen extending therebetween along the needle body axis; (b) a retriever body disposed within the needle lumen and translatable therein along the needle body axis; (c) a grasper arm comprising a proximal end, a proximal-to-intermediate portion, a distal portion, and a distal end, the grasper arm extending from the distal end of the retriever body and being reversibly moveable between a first position and a second position; and (d) a grasper magnet being disposed adjacent the proximal-to-intermediate portion of the grasper arm, the magnet-assisted suture grasper sequestering the grasper magnet within the needle lumen when the grasper arm is in the first position and exposing the grasper magnet from the needle lumen when the grasper arm is in the second position. The distal end of the grasper arm extends further distally than the grasper magnet. Translation of the retriever body within the needle lumen in a first direction along the needle body axis causes the grasper arm to move from the first position to the second position, thereby exposing the grasper magnet and allowing contact between the grasper magnet and a magnetic suture attracted thereto. Translation of the retriever body within the needle lumen in a second direction opposite the first direction along the needle body axis causes the grasper arm to move from the second position to the first position, thereby sequestering the grasper magnet and grasping the magnetic suture within the needle lumen.

In some embodiments, the suture retrieval needle is straight, the needle body axis thereby being straight.

In some embodiments, the suture retrieval needle is curved, the needle body axis thereby being curved.

In some embodiments, the suture retrieval needle has a sharp tip.

In some embodiments, the grasper arm is integral to the retriever body.

In some embodiments, the grasper magnet is fixedly attached to the distal end of the retriever body, either directly or indirectly.

In some embodiments, the grasper magnet is fixedly attached to the grasper arm, either directly or indirectly, at the proximal-to-intermediate portion of the grasper arm. Also in some embodiments.

In some embodiments, the magnet-assisted suture grasper further comprises a magnet wire having a proximal end and a distal end, wherein the proximal end of the magnet wire is fixedly disposed within the retriever body and the grasper magnet is fixedly attached to the distal end of the magnet wire, either directly or indirectly.

In some embodiments, the grasper arm further comprises an enlarged distal terminus at the distal end of the grasper arm; the grasper arm is reversibly moveable between the first position and the second position based on translation of the grasper arm from inside of the needle lumen to outside of the needle lumen through the distal hole of the needle body; and the enlarged distal terminus at the distal end of the grasper arm has a size sufficiently small to allow contact between the grasper magnet and a suture magnet of a magnetic suture attracted thereto when the grasper arm is in the second position and to allow a suture of the magnetic suture to pass when the grasper arm is in the first position, and sufficiently large to block the suture magnet of the magnetic suture from exiting the needle lumen through the distal hole of the needle body when the grasper arm is in the first position. In some of these embodiments, the enlarged distal terminus comprises a hook.

In some embodiments, the grasper arm is a first grasper arm; the magnet-assisted suture grasper further comprises a second grasper arm comprising a proximal end, a proximal-to-intermediate portion, a distal portion, and a distal end, the second grasper arm extending from the distal end of the retriever body and being reversibly moveable between the first position and the second position; the first grasper arm further comprises an enlarged distal terminus at the distal end of the first grasper arm; the second grasper arm further comprises an enlarged distal terminus at the distal end of the second grasper arm; the first and second grasper arms are reversibly moveable between the first position and the second position based on translation of the first and second grasper arms from inside of the needle lumen to outside of the needle lumen through the distal hole of the needle body; and the enlarged distal termini of the first and second grasper arms have sizes sufficiently small to allow contact between the grasper magnet and a suture magnet of a magnetic suture attracted thereto when the first and second grasper arms are in the second position and to allow a suture of a magnetic suture to pass when the first and second grasper arms are in the first position, and sufficiently large to block the suture magnet of the magnetic suture from exiting the needle lumen through the distal hole of the needle body when the first and second grasper arms are in the first position. In some of these embodiments, the magnet-assisted suture grasper further comprises at least one additional grasper arm extending distally from the retriever body.

In some embodiments, the grasper arm is a first grasper arm; the magnet-assisted suture grasper further comprises a second grasper arm comprising a proximal end, a proximal-to-intermediate portion, a distal portion, and a distal end, the second grasper arm extending from the distal end of the retriever body and being reversibly moveable between the first position and the second position; the first and second grasper arms are connected at their distal ends, thereby forming a grasper arm loop; the grasper arm loop is reversibly moveable between the first position and the second position based on translation of the grasper arm loop from inside of the needle lumen to outside of the needle lumen through the distal hole of the needle body; the grasper arm loop circumscribes an area sufficiently large to allow contact between the grasper magnet and a suture of a magnetic suture attracted thereto when the grasper arm loop is in the second position; and the grasper arm loop has a thickness sufficiently great to block the suture magnet of the magnetic suture from exiting the needle lumen through the distal hole of the needle body when the grasper arm loop is in the first position.

In some embodiments, the grasper arm is a first grasper arm; the magnet-assisted suture grasper further comprises a second grasper arm comprising a proximal end, a proximal-to-intermediate portion, a distal portion, and a distal end, the second grasper arm extending from the distal end of the retriever body and being reversibly moveable between the first position and the second position; the first and second grasper arms are connected at their distal ends, thereby forming a grasper arm loop; the first and second grasper arms further comprise an enlarged distal terminus at the distal ends of the first and second grasper arms; the grasper arm loop is reversibly moveable between the first position and the second position based on translation of the grasper arm loop from inside of the needle lumen to outside of the needle lumen through the distal hole of the needle body; the grasper arm loop circumscribes an area sufficiently large, and the enlarged distal terminus at the distal ends of the first and second grasper arms has a size sufficiently small, to allow contact between the grasper magnet and a suture magnet of a magnetic suture attracted thereto when the grasper arm loop is in the second position; the enlarged distal terminus at the distal ends of the first and second grasper arms has a size sufficiently small to allow a suture of the magnetic suture to pass when the grasper arm loop is in the first position; and the enlarged distal terminus at the distal ends of the first and second grasper arms has a size sufficiently large to block the suture magnet of the magnetic suture from exiting the needle lumen through the distal hole of the needle body when the grasper arm loop is in the first position.

In some embodiments, the grasper arm is a first grasper arm; the magnet-assisted suture grasper further comprises a second grasper arm comprising a proximal end, a proximal-to-intermediate portion, a distal portion, and a distal end, the second grasper arm extending from the distal end of the retriever body and being reversibly moveable between the first position and the second position; the first grasper arm further comprises an enlarged distal terminus at the distal end of the first grasper arm; the second grasper arm further comprises an enlarged distal terminus at the distal end of the second grasper arm; the first and second grasper arms are reversibly moveable between the first position and the second position based on translation of the first and second grasper arms from inside of the needle lumen to outside of the needle lumen through the distal hole of the needle body; the proximal-to-intermediate portions of the first and second grasper arms are substantially parallel to the needle body axis when the first and second grasper arms are in the first position; at least one of the first or second grasper arms pivots reversibly outwardly from the needle body axis sufficiently far to allow contact between the grasper magnet and a suture magnet of a magnetic suture attracted thereto when the first and second grasper arms are in the second position; and the enlarged distal termini of the first and second grasper arms have sizes sufficiently small to allow a suture of the magnetic suture to pass when the first and second grasper arms are in the first position, and sufficiently large to block the suture magnet of the magnetic suture from exiting the needle lumen through the distal hole of the needle body when the first and second grasper arms are in the first position.

A system for passing a magnetic suture also is disclosed. The system comprises the magnet-assisted suture grasper comprising (a) a suture retrieval needle, (b) a retriever body, (c) a grasper arm, and (d) a grasper magnet as described above. The system also comprises a magnetic suture comprising a suture magnet and a suture extending from the suture magnet.

Another system for passing a magnetic suture also is disclosed. The system comprises the magnet-assisted suture grasper comprising (a) a suture retrieval needle, (b) a retriever body, (c) a grasper arm, and (d) a grasper magnet as described above. The system also comprises a magnetic suture loop comprising a suture magnet and a bifurcated suture extending from the suture magnet and forming a suture loop. In some embodiments, the system further comprises a cartridge tube, wherein: the cartridge tube comprises a cartridge tube proximal opening, a cartridge tube distal opening, and a cartridge tube lumen therebetween; the suture loop traverses the cartridge tube lumen based on having been inserted through the cartridge tube distal opening; and the suture magnet is disposed outside of the cartridge tube lumen adjacent the cartridge tube distal opening.

Another magnet-assisted suture grasper for grasping a magnetic suture also is disclosed. The magnet-assisted suture grasper comprises: (a) a handle; (b) a stem comprising a proximal end, a distal end, and a stem body extending therebetween, the stem being connected to the handle adjacent the proximal end of the stem, the stem body defining a stem body axis and including a stem lumen extending along the stem; (c) a first grasper jaw comprising a proximal end, a proximal-to-intermediate portion, a distal portion, and a distal end, the first grasper jaw extending from the stem adjacent the distal end of the stem and being reversibly moveable between a first position and a second position; (d) a second grasper jaw comprising a proximal end, a proximal-to-intermediate portion, a distal portion, and a distal end, the second grasper jaw extending from the stem adjacent the distal end of the stem; (e) a grasper magnet being disposed adjacent the proximal-to-intermediate portion of the first grasper jaw, the magnet-assisted suture grasper sequestering the grasper magnet between the first and second grasper jaws in a recess formed in at least one of the first or second grasper jaws when the first grasper jaw is in the first position and exposing the grasper magnet from the recess when the first grasper jaw is in the second position; and (f) an actuator body disposed within the stem lumen and translatable therein along the stem body axis, the actuator body connected to the handle and the first grasper jaw and configured for pivotal actuation of the first grasper jaw by movement of the handle. The distal ends of the first and second grasper jaws extend further distally than the grasper magnet. Translation of the actuator body within the stem lumen in a first direction along the stem body axis causes the first grasper jaw to pivot from the first position to the second position, thereby exposing the grasper magnet and allowing contact between the grasper magnet and a magnetic suture attracted thereto. Translation of the actuator body within the stem lumen in a second direction opposite the first direction along the stem body axis causes the first grasper jaw to pivot from the second position to the first position, thereby sequestering the grasper magnet and grasping the magnetic suture within the recess.

In some embodiments, the first grasper jaw is straight from the proximal end of the first grasper jaw to the distal end of the first grasper jaw relative to the stem body axis.

In some embodiments, the first grasper jaw is curved from the proximal end of the first grasper jaw to the distal end of the first grasper jaw relative to the stem body axis.

In some embodiments, the first grasper jaw defines a first grasper jaw axis and the proximal-to-intermediate portion of the first grasper jaw comprises a recessed portion along the first grasper jaw axis that defines at least part of the recess.

In some embodiments, the second grasper jaw defines a second grasper jaw axis and the proximal-to-intermediate portion of the second grasper jaw comprises a recessed portion along the second grasper jaw axis that defines at least part of the recess.

In some embodiments, the first grasper jaw defines a first grasper jaw axis, the second grasper jaw defines a second grasper jaw axis, and the proximal-to-intermediate portions of the first and second grasper jaws comprise recessed portions along the first grasper jaw axis and the second grasper jaw axis, respectively, that define the recess.

In some embodiments, the grasper magnet is fixedly attached to the proximal-to-intermediate portion of the first grasper jaw.

In some embodiments, the grasper magnet is fixedly attached to the proximal-to-intermediate portion of the second grasper jaw.

In some embodiments, the grasper magnet is fixedly attached to the stem between the proximal-to-intermediate portions of the first and second grasper jaws.

In some embodiments, the second grasper jaw is reversibly moveable; the actuator body is further connected to the second grasper jaw and configured for pivotal actuation of the second grasper jaw by movement of the handle; translation of the actuator body within the stem lumen in the first direction causes the second grasper jaw to pivot away from the first grasper jaw, thereby further exposing the grasper magnet and allowing contact between the grasper magnet and a magnetic suture attracted thereto; and translation of the actuator body within the stem lumen in the second direction causes the second grasper jaw to pivot toward the first grasper jaw, thereby contributing to sequestering the grasper magnet and grasping the magnetic suture within the recess.

In some embodiments, the distal ends of the first and second grasper jaws have sharp tips.

Another system for passing a magnetic suture also is disclosed. The system comprises the magnet-assisted suture grasper comprising (a) a handle, (b) a stem, (c) a first grasper jaw, (d) a second grasper jaw, (e) a grasper magnet, and (f) an actuator body as described above. The system also comprises a magnetic suture comprising a suture magnet and a suture extending from the suture magnet.

Another system for passing a magnetic suture also is disclosed. The system comprises the magnet-assisted suture grasper comprising (a) a handle, (b) a stem, (c) a first grasper jaw, (d) a second grasper jaw, (e) a grasper magnet, and (f) an actuator body as described above. The system also comprises a magnetic suture loop comprising a suture magnet and a bifurcated suture extending from the suture magnet and forming a suture loop.

In some embodiments, the system further comprises a cartridge tube, wherein: the cartridge tube comprises a cartridge tube proximal opening, a cartridge tube distal opening, and a cartridge tube lumen therebetween; the suture loop traverses the cartridge tube lumen based on having been inserted through the cartridge tube distal opening; and the suture magnet is disposed outside of the cartridge tube lumen adjacent the cartridge tube distal opening.

BRIEF DESCRIPTION OF THE DRAWINGS

These and other features, aspects, and advantages of the present disclosure are better understood when the following detailed description is read with reference to the accompanying drawings, which are as follows.

FIG. 1 is a side view of a first magnet-assisted suture grasper as disclosed herein. The magnet-assisted suture grasper comprises a suture retrieval needle, a retriever body, a grasper arm, and a grasper magnet. The grasper arm is in a position exposing the grasper magnet and allowing contact between the grasper magnet and a magnetic suture attracted thereto, termed the second position, as discussed herein. The grasper magnet is attached directly to the retriever body.

FIG. 2 is a sectional view of the magnet-assisted suture grasper of FIG. 1, in which the grasper arm is in the second position.

FIG. 43 is a top view of a magnetic suture loop as disclosed herein.

FIG. 44 is an expanded view of a loop-end and a magnet-end of the magnetic suture loop of FIG. 43.

FIG. 45 is a front view of the magnetic suture loop of FIG. 43.

FIG. 46 is a back view of the magnetic suture loop of FIG. 43.

FIG. 47 is an expanded sectional view of the magnet-end of the magnetic suture loop of FIG. 43.

FIG. 48 is a side view of a preloaded magnetic suture cartridge as disclosed herein.

FIG. 49 is a sectional view of the magnet-end of the preloaded magnetic suture cartridge of FIG. 48.

DETAILED DESCRIPTION

Figure 3:
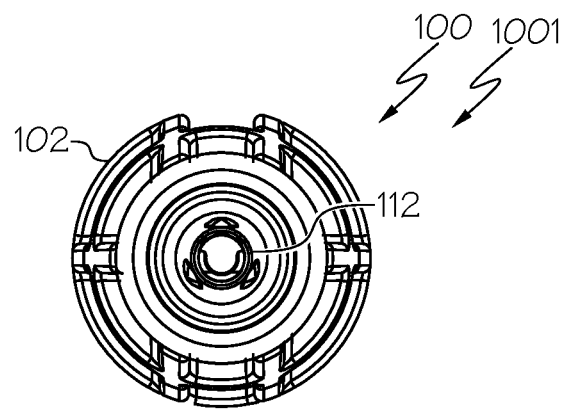
FIG. 3 is a front view of the magnet-assisted suture grasper of FIG. 1, in which the grasper arm is in the second position.
Figure 4:
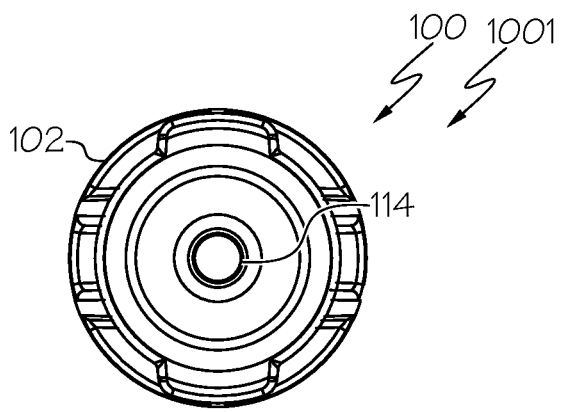
FIG. 4 is a back view of the magnet-assisted suture grasper of FIG. 1.

A magnet-assisted suture grasper for grasping a magnetic suture is disclosed. The magnet-assisted suture grasper comprises (a) a suture retrieval needle, (b) a retriever body, (c) a grasper arm, and (d) a grasper magnet. The suture retrieval needle comprises a proximal end, a distal end, and a needle body extending therebetween. The needle body defines a needle body axis between the proximal and distal ends of the suture retrieval needle. The needle body has a proximal hole, a distal hole, and a needle lumen extending therebetween along the needle body axis. The retriever body is disposed within the needle lumen and translatable therein along the needle body axis. The grasper arm comprises a proximal end, a proximal-to-intermediate portion, a distal portion, and a distal end. The grasper arm extends from the distal end of the retriever body and is reversibly moveable between a first position and a second position. The grasper magnet is disposed adjacent the proximal-to-intermediate portion of the grasper arm. The magnet-assisted suture grasper sequesters the grasper magnet within the needle lumen when the grasper arm is in the first position and exposes the grasper magnet from the needle lumen when the grasper arm is in the second position. The distal end of the grasper arm extends further distally than the grasper magnet. Translation of the retriever body within the needle lumen in a first direction along the needle body axis causes the grasper arm to move from the first position to the second position, thereby exposing the grasper magnet and allowing contact between the grasper magnet and a magnetic suture attracted thereto. Translation of the retriever body within the needle lumen in a second direction opposite the first direction along the needle body axis causes the grasper arm to move from the second position to the first position, thereby sequestering the grasper magnet and grasping the magnetic suture within the needle lumen.

A magnet-assisted suture grasper for grasping a magnetic suture comprising (a) a handle, (b) a stem, (c) a first grasper jaw, (d) a second grasper jaw, (e) a grasper magnet, and (f) an actuator body also is disclosed. The stem comprises a proximal end, a distal end, and a stem body extending therebetween. The stem is connected to the handle adjacent the proximal end of the stem. The stem body defines a stem body axis and includes a stem lumen extending along the stem. T first grasper jaw comprises a proximal end, a proximal-to-intermediate portion, a distal portion, and a distal end. The first grasper jaw extends from the stem adjacent the distal end of the stem and is reversibly moveable between a first position and a second position. The second grasper jaw comprises a proximal end, a proximal-to-intermediate portion, a distal portion, and a distal end. The second grasper jaw extends from the stem adjacent the distal end of the stem. The grasper magnet is disposed adjacent the proximal-to-intermediate portion of the first grasper jaw. The magnet-assisted suture grasper sequesters the grasper magnet between the first and second grasper jaws in a recess formed in at least one of the first or second grasper jaws when the first grasper jaw is in the first position and exposes the grasper magnet from the recess when the first grasper jaw is in the second position. The actuator body is disposed within the stem lumen and is translatable therein along the stem body axis. The actuator body is connected to the handle and the first grasper jaw and configured for pivotal actuation of the first grasper jaw by movement of the handle. The distal ends of the first and second grasper jaws extend further distally than the grasper magnet. Translation of the actuator body within the stem lumen in a first direction along the stem body axis causes the first grasper jaw to pivot from the first position to the second position, thereby exposing the grasper magnet and allowing contact between the grasper magnet and a magnetic suture attracted thereto. Translation of the actuator body within the stem lumen in a second direction opposite the first direction along the stem body axis causes the first grasper jaw to pivot from the second position to the first position, thereby sequestering the grasper magnet and grasping the magnetic suture within the recess.

Our magnet-assisted suture graspers address the technical difficulty associated with capturing and retrieving sutures under indirect non-stereoscopic visualization. Our magnet-assisted suture graspers involve use of two dipole magnets, a grasper magnet of a magnet-assisted suture grasper and a suture magnet of a magnetic suture, to assist with the initial positioning and holding of a magnetic suture while the magnetic suture is captured by a secondary mechanical means of the magnet-assisted suture grasper. The use of the two dipole magnets allows for a self-aligning feature, whereby the attractive forces of the northern and southern poles of the grasper magnet and the suture magnet cause the two magnets to align in a predictable manner, improving aspects of repeatability and reliability of function. Our magnet-assisted suture graspers greatly reduce the need to precisely position a suture passer, as the two magnetic aspects need only be brought near enough to one another that the magnetic fields can interact. The magnetic aspect of the suture is pulled into contact with the grasper magnet. This occurs without need for precise positioning to make contact. The secondary mechanical means then provides a steady-state connection between the magnetic suture and the magnet-assisted suture grasper that serves to hold the suture to the magnet-assisted suture grasper, allowing retrieval of the suture through soft tissue of a patient without needing to rely on magnetic attraction between the grasper magnet and the suture magnetic during the retrieval.

While we initially envisioned that sutures would be retrieved from a patient's body relying on the magnetic attraction between the grasper magnet and the suture magnet, in vitro testing revealed a problem whereby frictional drag associated with pulling a suture through soft tissues was greater than the attractive force between the grasper magnet and the suture magnet, resulting in separation of the magnets. The two magnets were too small. The size of the magnets is restricted by the need to pass them through a cannula for delivery, and the desire to minimize the size of the cannula to minimize trauma associated with tissue penetration by the cannula. We could not increase the size of the magnets to provide a greater attractive strength. We realized, though, that we could solve this problem by using a mechanical trap that works in conjunction with the walls of the cannula to secure the suture against greater loads than the magnetic connection can withstand.

More specifically, initially we intended to incorporate a magnetic suture, including a suture magnet, such as the magnetic suture described in U.S. Pub. No. 2021/0059667, and a device including a magnetic suture retriever with a magnetic end, similar to the retrieval probe of the magnetic U-stitch suturing device described in U.S. Pat. No. 10,245, 021. The suture would be introduced using a 17 gauge hypodermic needle. For certain procedures, such as the inguinal hernia repair technique referenced above, the needle must then be removed before introduction of a retriever. In the inguinal hernia repair procedure, the suture would be deposited with the magnetic end inside the peritoneal cavity, and the suture extending through the abdominal wall. The magnetic suture retriever would then be introduced through the same percutaneous site, using a 17 gauge needle. This could be a second needle, or it could be the same needle that was used to introduce the suture. The magnetic suture retriever would then be brought near the magnetic end of the suture so that the magnets would connect. Once the magnets were connected, the magnetic retriever would be withdrawn, pulling the suture with it.

While prototyping this device, we determined that the attractive force between the magnets of the magnetic suture retriever and the magnetic suture was not strong enough to resist the frictional drag that results from pulling the suture through soft tissue. For comparison, for the magnetic U-stitch device described in U.S. Pat. No. 10,245,021, the suture never contacts tissue during retrieval. Instead, the suture travels through one cannula, into an open space, and then back through another cannula. There is minimal drag created by passing the suture through these cannulas. However, in the case of the inguinal hernia procedure, which is typically done on pediatric patients, there is not sufficient room for two needles to occupy relevant space in the patient simultaneously. The suture needs to be dropped first from an introducer needle. Then the introducer needle needs to be removed. Then the magnetic suture retriever would need to be able to retrieve the suture.

We realized, though, that the frictional drag created by pulling the suture through soft tissue is a problem. The drag creates a tensile load on the suture which is greater than the attractive force between the magnets, causing the magnets to disconnect and the suture to be dropped. Due to the small size of the pediatric patients, increasing the size of the introducer needle would be disadvantageous. However, without increasing the size of the needle, the diameter of magnets that can be used is limited, which limits the strength of the attractive force between the magnets. A current design for the magnetic U-stitch device uses a 17 gauge XT wall hypodermic needle that has an inner lumen diameter of 0.049-0.051 inches (1.24 to 1.30 mm), accounting for manufacturing tolerances. The corresponding magnet has a nominal outer diameter of 0.035 inches (0.889 mm), and a ferrule diameter of 0.037±0.001 inches (0.940±0.025 mm). Each magnet has a pull force of approximately 0.102 lbf (0.454 N). Even increasing the magnet diameter to the theoretical max of 0.042 inches (1.07 mm), allowing for manufacturing tolerances and a minimal clearance of only 0.001 inches (0.025 mm), would only increase that pull force to approximately 0.145 lbf (0.645 N). A much larger magnet would be needed to overcome the drag of the soft tissue, but a larger magnet cannot be used due to the limitation imposed on needle size.

We have solved this problem, among other ways, by pairing the magnet on the retrieval device, termed a grasper magnet, with a mechanical arm, termed a grasper arm or a grasper jaw, in which the grasper arm has an enlarged distal terminus, a loop configuration, and/or other features that can mechanically block the exit path of the magnetic suture once the suture has been pulled into a needle of the retrieval device, or in which first and second grasper jaws can be pivotally closed about the magnetic suture, forming a recess into which a suture magnet of the magnetic suture can fit and also mechanically blocking the exit path of the magnetic suture once the grasper jaws have been pivotally closed about the magnetic suture. With the mechanical block in place, the ability to retain the magnetic suture against a tensile load is limited only by the strength of the mechanical arm, which can be far greater than the attractive force between the small grasper magnet and the small suture magnet. Our testing shows that the grasper arm advantageously retains the magnetic suture against forces far greater than the grasper magnet and the suture magnet can withstand. Indeed, the grasper arm advantageously retains the magnetic suture against forces great enough to break the suture, which is required to have a tensile strength of at least 3 lbf (13 N) by USP standards. The grasper jaws should be similarly effective. The mechanical solution is therefore at least approximately 30 times stronger than the grasper magnet and suture magnet alone.

Importantly, we realized that the retrieval instrument with a grasper magnet only needs to be brought near enough to the magnetic suture for the magnetic fields of the grasper magnet and the suture magnet to interact. Advantageously, this does not require very precise positioning. The magnetic fields are oriented such that when the fields begin to interact, the suture magnet is pulled towards the grasper magnet and the magnets self-align and connect in the same orientation each time. While the strength of the grasper magnet and the suture magnet is not great enough to pull the magnetic suture through soft tissue on its own, we realized that it is strong enough to keep the magnets in contact with each other while the retrieval instrument is manipulated, allowing the user to mechanically capture the magnetic suture, even if the retrieval instrument and the magnetic suture are not held very steady.

Figure 20:
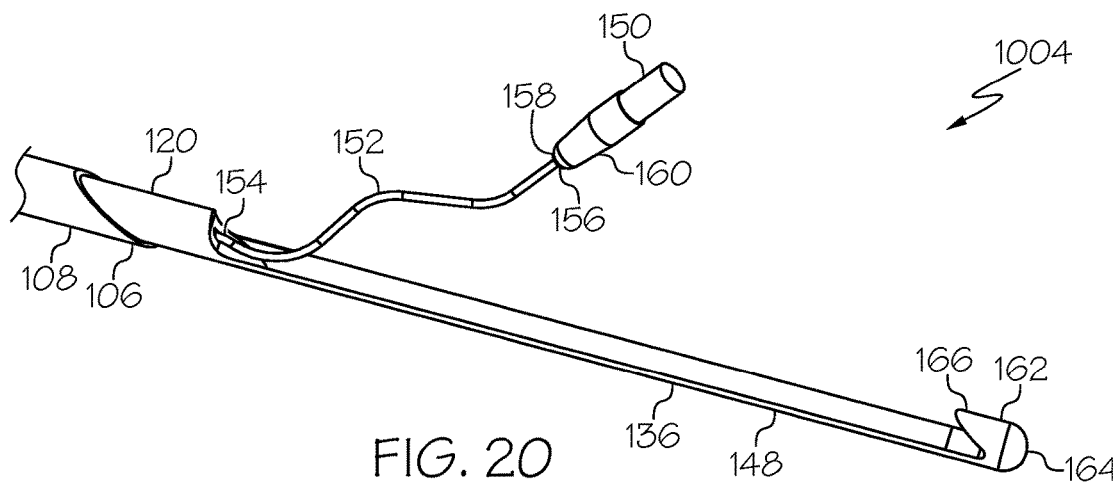
FIG. 20 is a perspective view of a third alternate embodiment of a grasper arm of a magnet-assisted suture grasper as disclosed herein, in which the grasper arm is in the second position and in which the grasper magnet is attached to the retriever body by a magnet wire.
Figure 21:
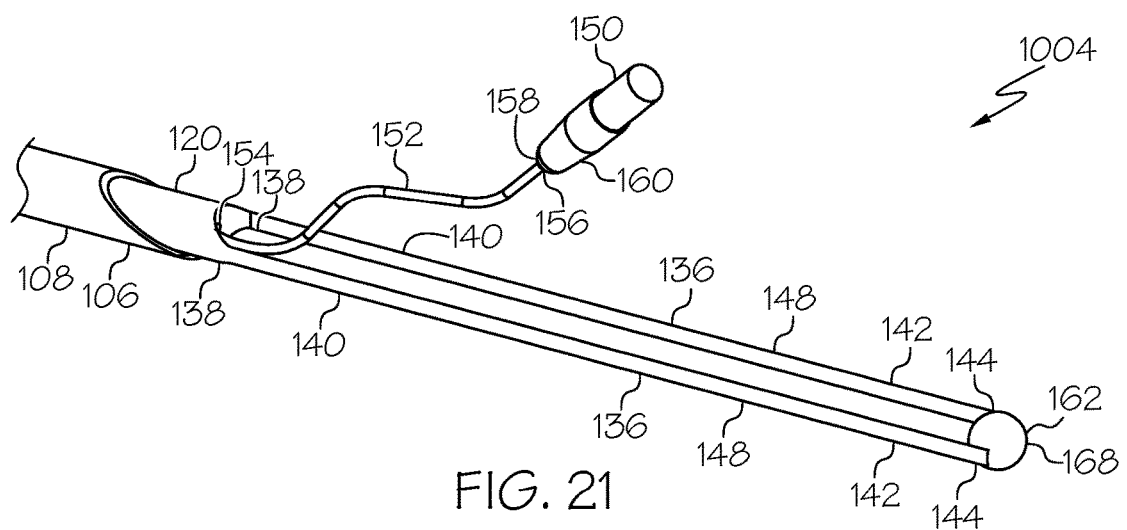
FIG. 21 is a perspective view of a fourth alternate embodiment of a grasper arm of a magnet-assisted suture grasper as disclosed herein, in which the magnet-assisted suture grasper comprises first and second grasper arms that form a grasper loop and that comprise an enlarged distal terminus at their distal ends and the grasper magnet is attached to the retriever body by a magnet wire.

FIGS. 1-11 illustrate a first embodiment 1001 of the magnet-assisted suture grasper 100 comprising (a) a suture retrieval needle, (b) a retriever body, (c) a grasper arm, and (d) a grasper magnet as disclosed herein. FIGS. 12-15 illustrate a second embodiment 1002. FIGS. 16-19 illustrate a third embodiment 1003. FIG. 20 and FIG. 21 illustrate a fourth embodiment 1004 and a fifth embodiment 1005, respectively. The magnet-assisted suture grasper 100 is discussed mainly with respect to the first embodiment 1001. Differences between the second through fifth embodiments 1002-1005 and the first embodiment 1001 also are discussed. Except to the extent that differences are indicated or apparent, the discussion regarding the first embodiment 1001 also applies to the second through fifth embodiments 1002-1005.

Figure 7:
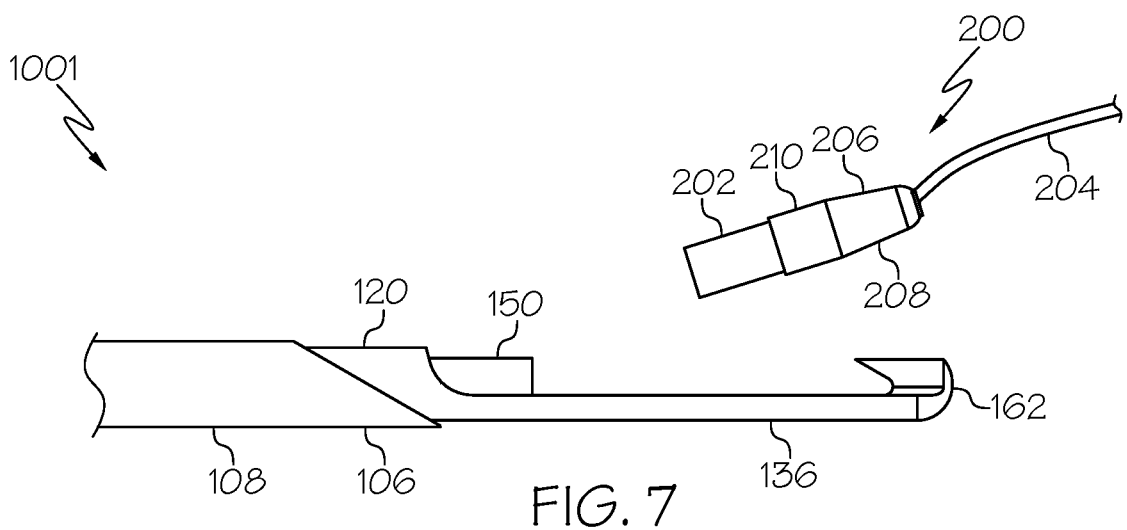
FIG. 7 is a side view of a distal end of the magnet-assisted suture grasper of FIG. 1 in which the grasper arm is in the second position and the grasper magnet is attracting a magnetic suture.
Figure 8:
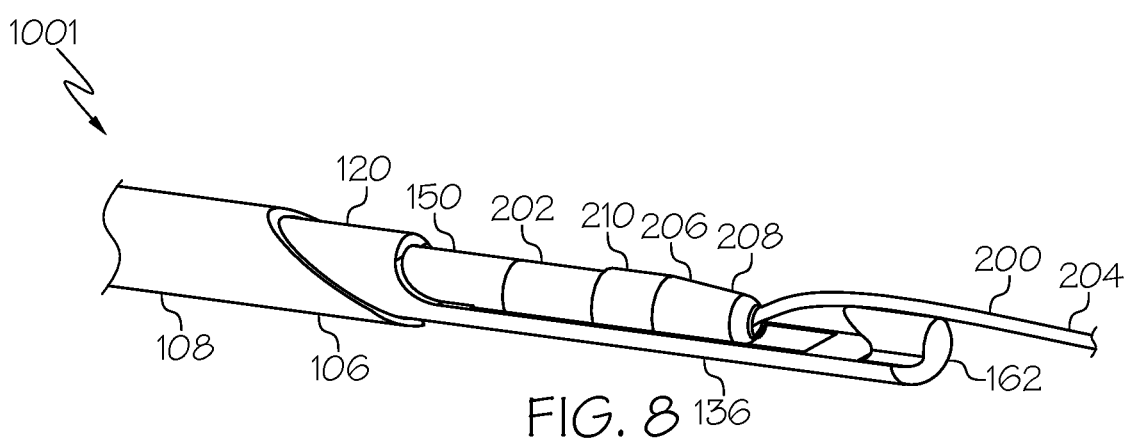
FIG. 8 is a perspective view of a distal portion of the magnet-assisted suture grasper of FIG. 1 in which the grasper arm is in the second position and the grasper magnet is attracting a magnetic suture and is contact with the magnetic suture.

With reference to FIG. 7, the magnetic suture 200 to be grasped can comprise a suture magnet 202 and a suture 204 extending from the suture magnet 202. The magnetic suture 200 can be, for example, a magnetic suture as described in U.S. Pub. No. 2021/0059667, which is incorporated herein by reference. Thus, the magnetic suture 200 can further comprise a ferrule 206 with a tapered region 208 in which the suture 204 is provided knotted and secured with an adhesive and a straight region 210 in which the suture magnet 202 is provided.

As shown in FIGS. 1-4 for the first embodiment 1001, the magnet-assisted suture grasper 100 comprises a suture retrieval needle 102 comprising a proximal end 104, a distal end 106, and a needle body 108 extending therebetween. The needle body 108 defines a needle body axis 110 between the proximal end 104 and distal end 106 of the suture retrieval needle 102. The needle body 108 has a proximal hole 112, a distal hole 114, and a needle lumen 116 extending therebetween along the needle body axis 110.

As shown in FIG. 1 for the first embodiment 1001, the suture retrieval needle 102 can be a hypodermic needle. For example, the suture retrieval needle 102 can be an introducer needle designed for introducing guide wires into a vessel, applied here as the suture retrieval needle 102. Also for example, the suture retrieval needle 102 can be a 24-gauge needle, a 21-gauge needle, an 18-gauge needle, a 17-gauge needle, a 16-gauge needle, or a 14 gauge needle.

Accordingly, in some embodiments, the suture retrieval needle 102 is a hypodermic needle. In some embodiments, the suture retrieval needle 102 is an introducer needle. In some embodiments, the suture retrieval needle 102 is a 24-gauge needle, a 21-gauge needle, an 18-gauge needle, a 17-gauge needle, a 16-gauge needle, or a 14 gauge needle.

As shown in FIG. 1 for the first embodiment 1001, in some embodiments the suture retrieval needle 102 is straight. In accordance with these embodiments, the needle body axis 110 thereby is straight. Alternatively, in some embodiments, the suture retrieval needle 102 is curved. In accordance with these embodiments, the needle body axis 110 thereby is curved. In some embodiments, one or more portions of the suture retrieval needle 102 can be straight, and one or more portions can be curved. For example, in some embodiments, the suture retrieval needle 102 includes a curve at or near its distal end 106 but otherwise is straight. In accordance with these embodiments, the needle body axis 110 also includes a curve at or near the distal end 106 of the suture retrieval needle 102, but otherwise is straight.

Figure 9:
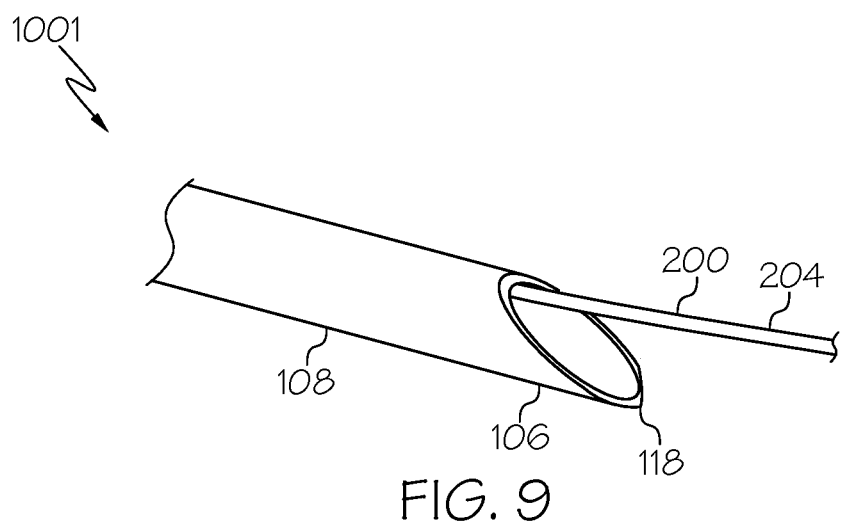
FIG. 9 is a perspective view a distal portion of the magnet-assisted suture grasper of FIG. 1 in which the grasper arm is in a position sequestering the grasper magnet within the needle lumen, termed the first position, and the grasper magnet is attracting the magnetic suture and in contact with the magnetic suture, such that the magnetic suture has been captured within the needle lumen of the suture retrieval needle of the magnet-assisted suture grasper.
Figure 14:
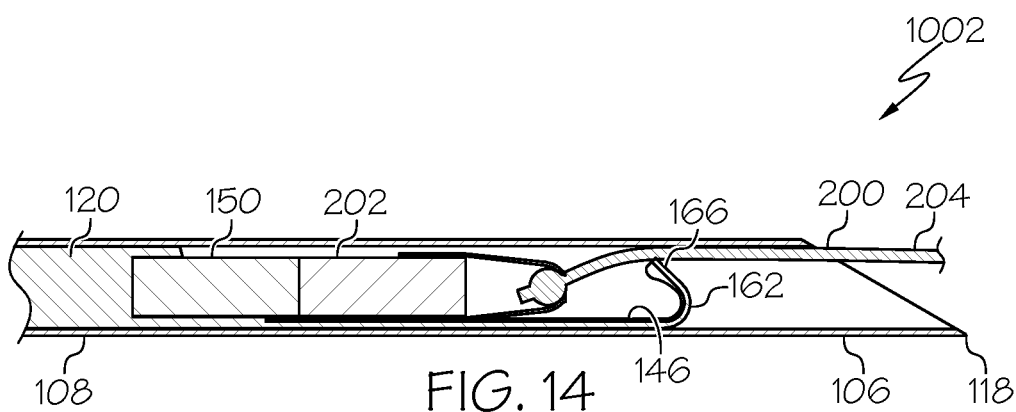
FIG. 14 is a sectional view of the first alternate embodiment of a grasper arm of a magnet-assisted suture grasper as disclosed herein, in which the grasper arm is in the first position and the grasper magnet is attracting the magnetic suture and in contact with the magnetic suture, such that the magnetic suture has been captured within the needle lumen of the suture retrieval needle of the magnet-assisted suture grasper.
Figure 15:
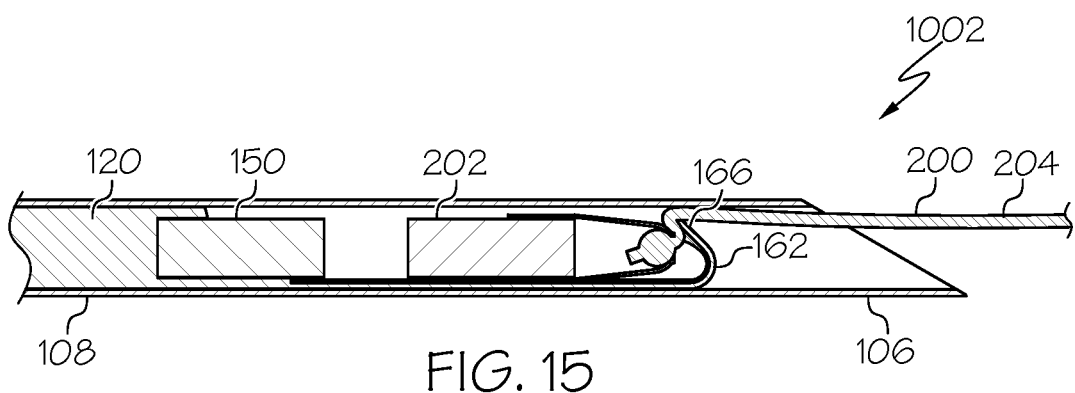
FIG. 15 is a sectional view of the first alternate embodiment of a grasper arm of a magnet-assisted suture grasper as disclosed herein, in which the grasper arm is in a position intermediate between the first position and the second position, and an enlarged distal terminus at the distal end of the grasper arm is grasping the magnetic suture, such that the magnetic suture remains captured within the needle lumen of the suture retrieval needle of the magnet-assisted suture grasper.
Figure 18:
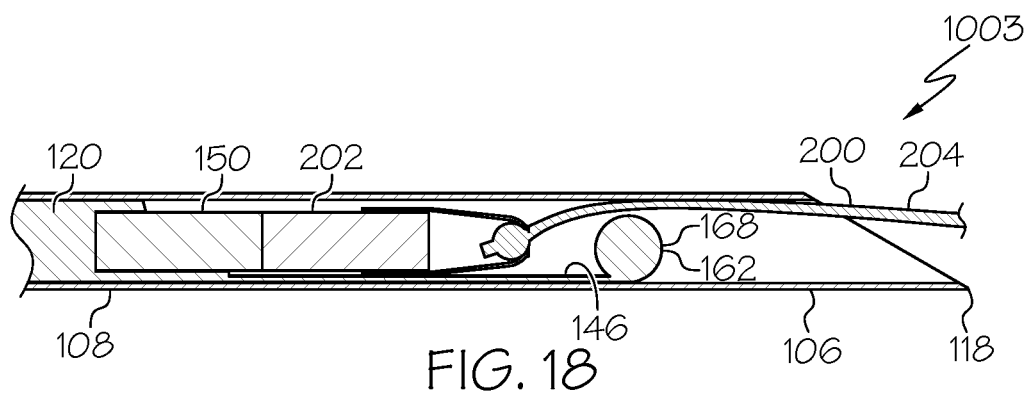
FIG. 18 is a sectional view of the second alternate embodiment of a grasper arm of a magnet-assisted suture grasper as disclosed herein, in which the grasper arm is in the first position and the grasper magnet is attracting the magnetic suture and in contact with the magnetic suture, such that the magnetic suture has been captured within the needle lumen of the suture retrieval needle of the magnet-assisted suture grasper.
Figure 19:
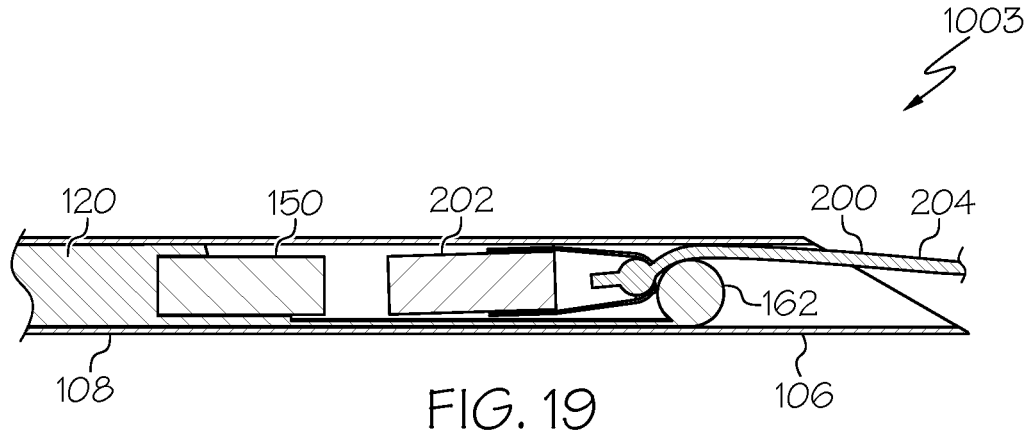
FIG. 19 is a sectional view of the second alternate embodiment of a grasper arm of a magnet-assisted suture grasper as disclosed herein, in which the grasper arm is in a position intermediate between the first position and the second position, and an enlarged distal terminus at the distal end of the grasper arm is grasping the magnetic suture, such that the magnetic suture remains captured within the needle lumen of the suture retrieval needle of the magnet-assisted suture grasper.

As shown in FIG. 1 and FIG. 9 for the first embodiment 1001, in FIG. 14 for the second embodiment 1002, and in FIG. 18 for the third embodiment 1003, in some embodiments the suture retrieval needle 102 has a sharp tip 118. This can be advantageous for piercing tissue during insertion of the suture retrieval needle 102 into a patient.

As shown in FIG. 1 for the first embodiment 1001, in some embodiments the suture retrieval needle 102 further comprises a hub 119. The hub 119 can have an open lumen.

As shown in FIG. 1, FIG. 12, FIG. 16, FIG. 20, and FIG. 21 for the first to fifth embodiments 1001-1005, respectively, the magnet-assisted suture grasper 100 also comprises a retriever body 120. The retriever body 120 is disposed within the needle lumen 116 and translatable therein along the needle body axis 110. The retriever body 120 can be made from a polymer, such as nylon, polyether ether ketone, polycarbonate, or acrylonitrile butadiene styrene, or a metal, such as stainless steel or Nitinol.

As shown in FIG. 2 for the first embodiment 1001, in some embodiments, the retriever body 120 comprises a proximal end 122, a distal end 124, and a retriever tube 126 extending therebetween. In these embodiments, the retriever tube 126 defines a retriever tube axis 128 between the proximal end 122 and distal end 124 of the retriever body 120, the retriever tube 126 has a proximal hole, a distal hole, and a retriever tube lumen extending therebetween along the retriever tube axis 128. In these embodiments, the proximal hole of the retriever tube 126 is in fluid communication with the distal hole 114 of the needle body 108 through the retriever tube lumen and the needle lumen 116. In these embodiments, the retriever body 120 preferably is made from a polymer such as nylon to facilitate making the retriever body 120 including the retriever tube lumen.

This can be advantageous by allowing recovery of liquids and/or gasses from a surgical site of a patient and/or delivery of contrast agents to the surgical site through the retriever tube lumen of the retriever body 120. Providing the ability to exchange fluids through the retriever body 120 and thus through the magnet-assisted suture grasper 100 broadens the applicability of the magnet-assisted suture grasper 100 for use with interventional techniques that employ fluid exchange to confirm the intracorporeal position of the distal end 106 of the suture retrieval needle 102 of the magnet-assisted suture grasper 100. For example, a need exists within the field of interventional radiology for the ability to confirm the location of cannulas inside the gastric lumens of patients during gastropexy. With the magnet-assisted suture grasper 100 comprising the retriever body 120 comprising the retriever tube lumen, following introduction of the suture retrieval needle 102 into a patient, aspiration of a small amount of stomach juice or air can be used to confirm the intraluminal position of the distal end 106 of the suture retrieval needle 102. Alternatively, a small amount of liquid radiographic contrast agent can be injected through the retriever tube lumen of the retriever body 120 into the gastric lumen of the patient, allowing the intraluminal position to be confirmed through radiographic imaging.

Also in some embodiments, the retriever body 120 is more flexible than the needle body 108. This can be advantageous for suture retrieval needles 102 in which one or more portions of the suture retrieval needle 102 are curved, e.g., a suture retrieval needle 102 that includes a curve at or near its distal end 106 but otherwise is straight. Then the retriever body 120 is preferentially made of a polymeric material, or a metal with a high proportional limit, such as Nitinol, to allow the retriever body 120 to elastically deform around the curve of the suture retrieval needle 102.

Also in some embodiments the retriever body 120 can be transparent. This allows for the use of photo-initiated adhesives, which can be advantageous for assembly of components. Photo-initiated adhesives provide more open time for component positioning, while requiring minimal fixture time due to a very rapid cure profile.

Figure 5:
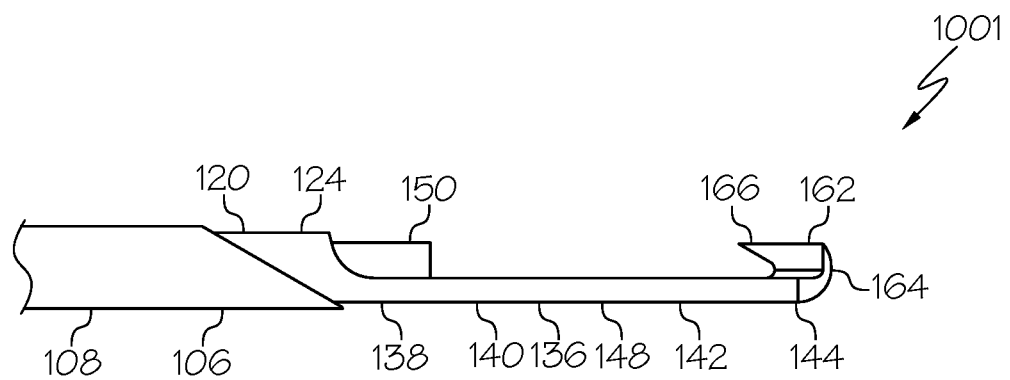
FIG. 5 is a side view of the distal end of the magnet-assisted suture grasper of FIG. 1 comprising the distal end of the suture retrieval needle, the distal end of the retriever body, the grasper arm, and the grasper magnet, in which the grasper arm is in the second position.
Figure 6:
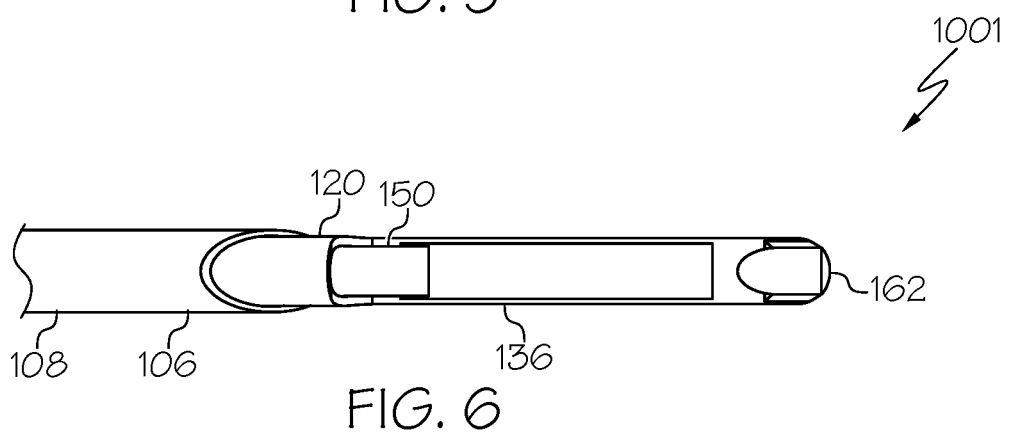
FIG. 6 is a top view of a distal end of the magnet-assisted suture grasper of FIG. 1 comprising the distal end of the suture retrieval needle, the distal end of the retriever body, the grasper arm, and the grasper magnet, in which the grasper arm is in the second position.

As shown in FIG. 1, FIG. 12, FIG. 16, FIG. 20, and FIG. 21 for the first to fifth embodiments 1001-1005, respectively, the magnet-assisted suture grasper 100 also comprises a grasper arm 136. As shown in FIG. 5 for the first embodiment 1001, the grasper arm 136 comprises a proximal end 138, a proximal-to-intermediate portion 140, a distal portion 142, and a distal end 144. Like the retriever body 120, the grasper arm 136 can be made from a polymer, such as nylon, polyether ether ketone, polycarbonate, or acrylonitrile butadiene styrene, or a metal, such as stainless steel or Nitinol. The grasper arm 136 also can be, for example, a wire, although other structures, such as a tube or other elongated member can be suitable too. Regarding the grasper arm 136 being a wire, the grasper arm 136 can be, for example, a metal wire, such as a Nitinol wire or a stainless steel wire, or a plastic wire, and can be formed, for example, as a solid wire, a stranded wire, or a braided wire, and can have a shape, for example, based on being a shaped wire and/or a stamped wire, and can comprise, for example, one or more wires joined together at one or more common points, for example, by welding, soldering, braiding, crimping, adhesive, or other means.

Figure 10:
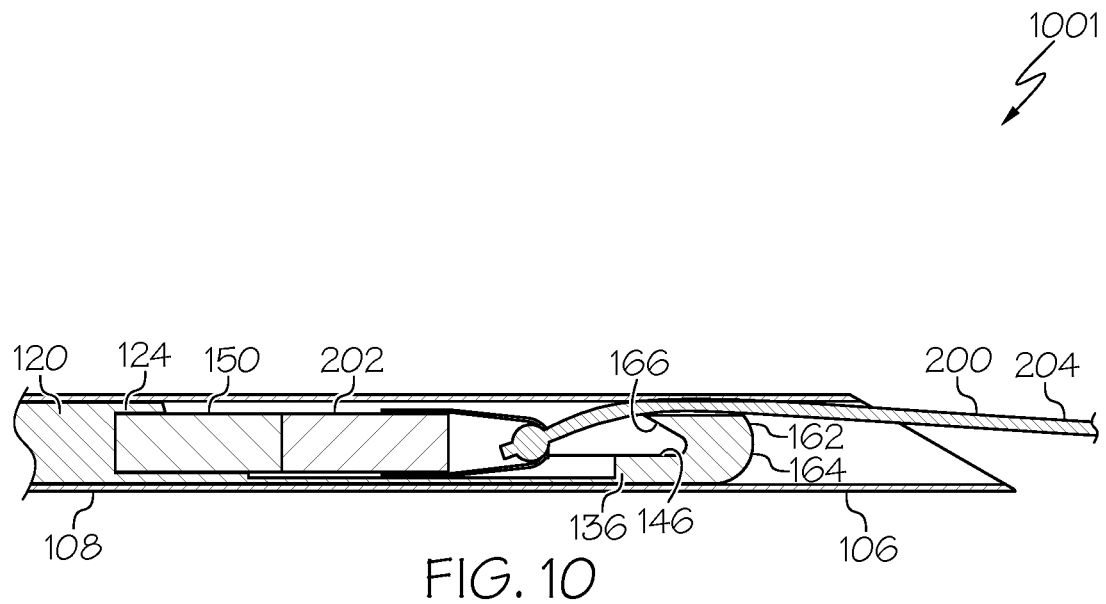
FIG. 10 is a sectional view a distal portion of the magnet-assisted suture grasper of FIG. 1 in which the grasper arm is in the first position and the grasper magnet is attracting the magnetic suture and in contact with the magnetic suture, such that the magnetic suture has been captured within the needle lumen of the suture retrieval needle of the magnet-assisted suture grasper.
Figure 11:
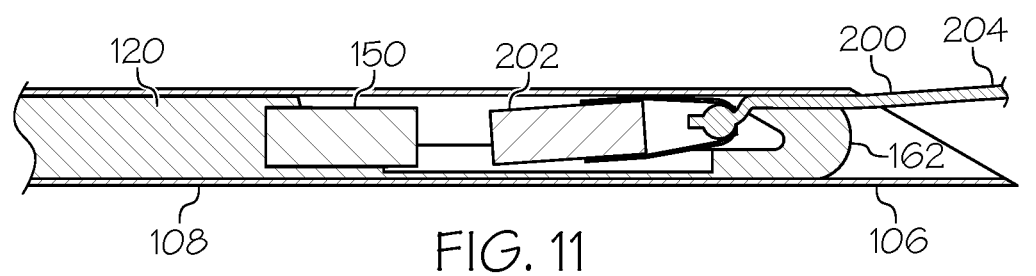
FIG. 11 is a sectional view a distal portion of the magnet-assisted suture grasper of FIG. 1 in which the grasper arm is in a position intermediate between the first position and the second position, and an enlarged distal terminus at the distal end of the grasper arm is grasping the magnetic suture, such that the magnetic suture remains captured within the needle lumen of the suture retrieval needle of the magnet-assisted suture grasper.

As shown by comparison of FIG. 5 and FIG. 10 for the first embodiment 1001, the grasper arm 136 extends from the distal end 124 of the retriever body 120 and is reversibly moveable between a first position 146 and a second position 148.

As shown for in FIG. 5 for the first embodiment 1001, the grasper arm 136 can extend from the distal end 124 of the retriever body 120, among other ways, based on the grasper arm 136 being integral to the retriever body 120. By this it is meant that the grasper arm 136 and the retriever body 120 can be adjacent portions of a single segment of material, such as a wire, e.g., a solid, stranded, or braided wire segment from which the retriever body 120 and the grasper arm 136 have been formed. In such examples the grasper arm 136 extends from the distal end 124 of the retriever body 120 based on the grasper arm 136 and the retriever body 120 forming a continuous wire segment through the distal end 124 of the retriever body 120.

Also for example, the grasper arm 136 can extend from the distal end 124 of the retriever body 120 directly, based on adhesion or other direct attachment of the grasper arm 136 to the retriever body 120. In these examples the grasper arm 136 can extend from the distal end 124 of the retriever body 120 based on the grasper arm 136 and the retriever body 120 forming segments of material connected at the distal end 124 of the retriever body 120 by adhesion.

Also for example, the grasper arm 136 can extend from the distal end 124 of the retriever body 120 indirectly, based on attachment through one, two, or more intermediate parts, such as a ring or a sleeve, among other intermediate parts. In these examples the grasper arm 136 can extend from the distal end 124 of the retriever body 120 based on the grasper arm 136 and the retriever body 120 forming wire segments connected at the distal end 124 of the retriever body 120 via intermediate parts.

As shown in FIG. 5, FIG. 12, FIG. 16, FIG. 20, and FIG. 21 for the first to fifth embodiments 1001-1005, respectively, the magnet-assisted suture grasper 100 also comprises a grasper magnet 150 disposed adjacent the proximal-to-intermediate portion 140 of the grasper arm 136. The magnet-assisted suture grasper 100 sequesters the grasper magnet 150 within the needle lumen 116 when the grasper arm 136 is in the first position 146 and exposes the grasper magnet 150 from the needle lumen 116 when the at least grasper arm 136 is in the second position 148. The grasper magnet 150 can be, for example, a permanent dipole magnet.

As shown in FIG. 5 with respect to the first embodiment 1001, in some embodiments the grasper magnet 150 is fixedly attached to the distal end 124 of the retriever body 120, either directly, e.g., based on adhesion or other direct attachment, or indirectly, e.g., based on attachment through one or more intermediate parts, such as a ferrule, ring, or sleeve, among other intermediate parts. For example, the grasper magnet 150 can be fixedly attached to the distal end 124 of the retriever body 120 within a pocket at the distal end 124 of the retriever body 120 by adhesion. Having the grasper magnet 150 fixedly attached to the distal end 124 of the retriever body 120 can be advantageous by allowing for use of a relatively short grasper arm 136.

Also in some embodiments the grasper magnet 150 is fixedly attached to the grasper arm 136, either directly or indirectly, at the proximal-to-intermediate portion 140 of the grasper arm 136.

As shown in FIG. 20 and FIG. 21 for the fourth embodiment 1001 and the fifth embodiment 1005, respectively, in some embodiments the magnet-assisted suture grasper 100 further comprises a magnet wire 152 having a proximal end 154 and a distal end 156, wherein the proximal end 154 of the magnet wire 152 is fixedly disposed within the retriever body 120 and the grasper magnet 150 is fixedly attached to the distal end 156 of the magnet wire 152, either directly, e.g., based on adhesion or other direct attachment, or indirectly, e.g., based on attachment through one or more intermediate parts, such as a ferrule, ring, or sleeve, among other intermediate parts. In accordance with these embodiments, translation of the retriever body 120 also results in translation of the magnet wire 152, and thus also the grasper magnet 150.

The magnet wire 152 can be fixedly disposed within the retriever body 120 by inserting the proximal end 154 of the magnet wire 152 into the retriever body 120 and securing the magnet wire 152 to the retriever body 120 so that the magnet wire 152 is translationally and rotationally fixed to the retriever body 120. The preferred method of assembly is to insert the magnet wire 152 into a lumen of the retriever body 120 and apply an adhesive to join the magnet wire 152 to the retriever body 120, but other means of attachment are also suitable.

As shown in FIG. 20 and FIG. 21 for the fourth embodiment 1001 and the fifth embodiment 1005, respectively, in some of these embodiments the magnet wire 152 further comprises a magnet wire distal terminus 158 at the distal end 156 of the magnet wire 152, the magnet-assisted suture grasper 100 further comprises a ferrule 160 attached to the magnet wire distal terminus 158 at the distal end 156 of the magnet wire 152, and the grasper magnet 150 is attached to the ferrule 160.

The magnet wire 152 can be, for example, a metal wire, such as a Nitinol wire or a stainless steel wire, or a plastic wire, and can be formed, for example, as a solid wire, a stranded wire, or a braided wire, and can have a shape, for example, based on being a shaped wire and/or a stamped wire, and can comprise, for example, one or more wires joined together at one or more common points, for example, by welding, soldering, braiding, crimping, adhesive, or other means.

Considering attachment of the grasper magnet 150 to the magnet wire 152 in more detail, the grasper magnet 150 can be attached to the magnet wire 152, for example, similarly as described in U.S. Pub. No. 2021/0059667 for attachment of a magnet to a suture. This can be accomplished as follows. The grasper magnet 150 can be attached to a ferrule 160, which is attached to a magnet wire 152 having an enlarged magnet wire distal terminus 158. With reference to U.S. Pub. No. 2021/0059667, the enlarged magnet wire distal terminus 158 would replace the knot tied in a suture. A ball end is the preferred shape for the magnet wire distal terminus 158 and a mono-filament with a round cross-section is the preferred shape of the magnet wire 152. However, as long as the magnet wire 152 and the magnet wire distal terminus 158 are sized appropriately, other constructions and final shapes would also be suitable. The magnet wire distal terminus 158 may be formed into any shape, e.g., cubic, cylindrical, pyramidal, organic, etc., and the magnet wire 152 may be of any cross sectional shape, e.g., square, rectangular, cruciform, etc., and may be of mono- or multi-filament construction.

The magnet wire 152 must be sized small enough to fit through the small opening of the ferrule 160, while the magnet wire distal terminus 158 must be sized larger than the small opening of the ferrule 160 and smaller than the large opening of the ferrule 160. The magnet wire distal terminus 158 may be integrated into the magnet wire 152, e.g., the magnet wire distal terminus 158 can be melt formed, coined, bent, etc., or it may be a separate component. If a separate component, it may be attached by mechanical means, e.g., swaged, threaded, interference fit, pinned, etc., by adhesive means, or by other means, e.g., welding, soldering, brazing, etc.

To assemble the grasper magnet 150, the ferrule 160, and the magnet wire 152, the magnet wire 152 is first passed through the ferrule 160 from its distal end to its proximal end, so that the magnet wire distal terminus 158 becomes positioned inside the ferrule. The grasper magnet 150 is then installed from the distal end, and attached to the ferrule 160. The grasper magnet 150 can be attached by mechanical means, e.g., swaged, threaded, interference fit, pinned, etc., or adhesive means or other means, e.g., welding, brazing, etc. Once the grasper magnet 150 is attached, the magnet wire distal terminus 158 is permanently captured between the grasper magnet 150 and the ferrule 160, and the subassembly is complete.

As shown in FIG. 20 and FIG. 21 for the fourth embodiment 1001 and the fifth embodiment 1005, respectively, in some embodiments of the magnet-assisted suture grasper 100 that further comprises a magnet wire 152 to which the grasper magnet 150 is fixedly attached as described, the grasper magnet 150 is displaced radially from the needle body axis 110 when the grasper arm 136 is in the second position 148. This can be advantageous by providing an operator of the magnet-assisted suture grasper 100 an additional range of motion to move the grasper magnet 150 within a site of a patient by rotation of the magnet-assisted suture grasper 100 and thus greater versatility in positioning the grasper magnet 150 relative to a magnetic suture 200 in the site.

As shown in FIG. 5, FIG. 12, FIG. 16, FIG. 20, and FIG. 21 for the first to fifth embodiments 1001-1005, respectively, the distal end 144 of the grasper arm 136 extends further distally than the grasper magnet 150. This means that when the grasper arm 136 is in the first position 146 that the distal end 144 of the grasper arm 136 extends further distally within the needle lumen 116 than does any portion of the grasper magnet 150. This also means that when the grasper arm 136 is in the second position 148 that the distal end 144 of the grasper arm 136 extends further distally from the suture retrieval needle 102 than does any portion of the grasper magnet 150. This also means that when the grasper arm 136 is in the second position 148 that the grasper magnet 150 is closer to the distal end 106 of the suture retrieval needle 102 than is the distal end 144 of the grasper arm 136.

Figure 12:
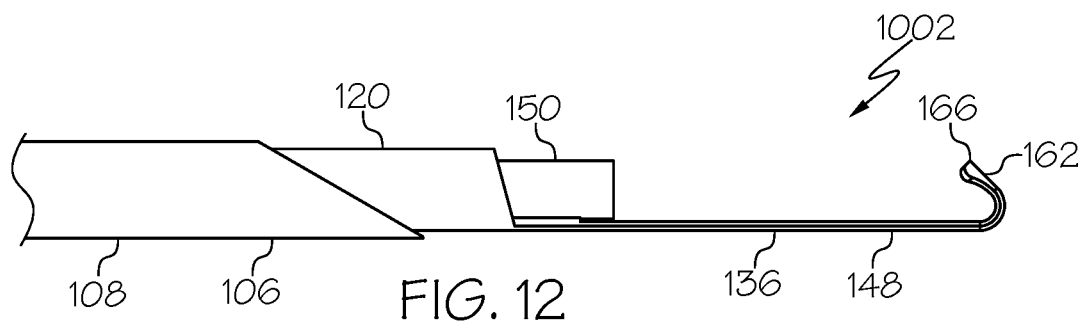
FIG. 12 is a side view of a first alternate embodiment of a grasper arm of a magnet-assisted suture grasper as disclosed herein, in which the grasper arm is in the second position.
Figure 13:
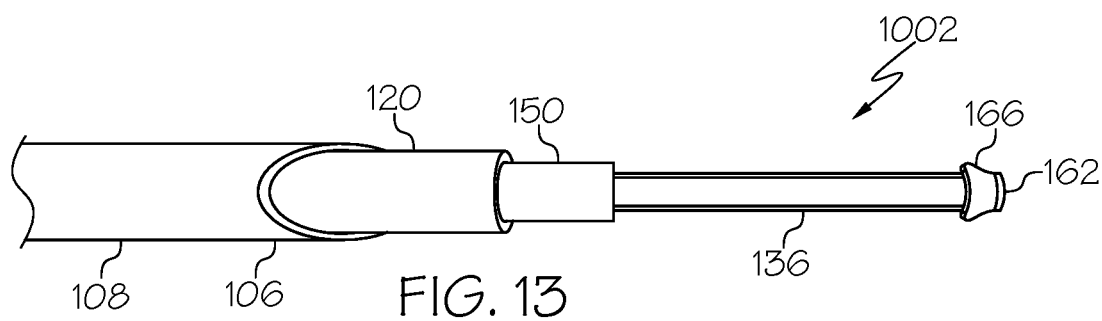
FIG. 13 is a top view of the first alternate embodiment of a grasper arm of a magnet-assisted suture grasper as disclosed herein, in which the grasper arm is in the second position.
Figure 16:
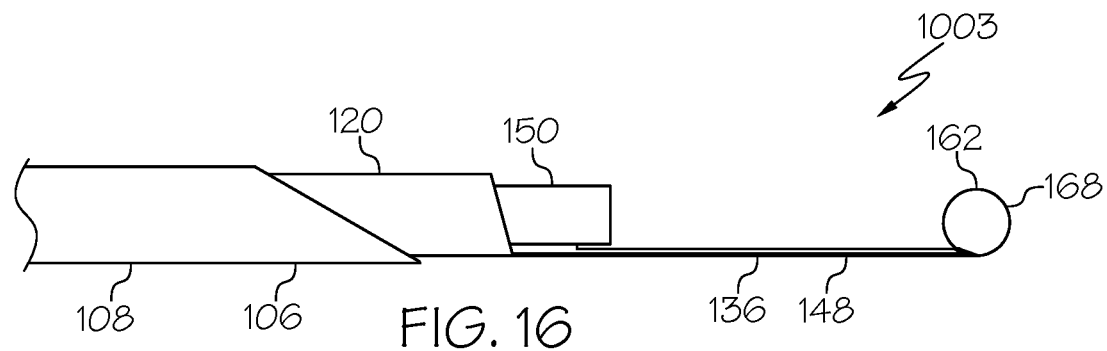
FIG. 16 is a side view of a second alternate embodiment of a grasper arm of a magnet-assisted suture grasper as disclosed herein, in which the grasper arm is in the second position.
Figure 17:
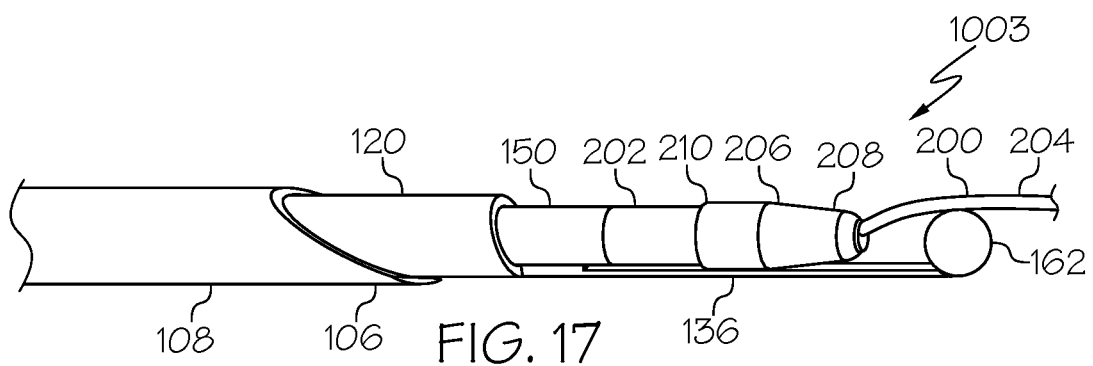
FIG. 17 is a top view of the second alternate embodiment of a grasper arm of a magnet-assisted suture grasper as disclosed herein, in which the grasper arm is in the second position.

As shown by comparison of FIG. 10 with FIG. 5 for the first embodiment 1001, comparison of FIG. 14 with FIG. 12 for the second embodiment 1002, and comparison of FIG. 18 with FIG. 16 for the third embodiment 1003, translation of the retriever body 120 within the needle lumen 116 in a first direction along the needle body axis 110 causes the grasper arm 136 to move from the first position 146 to the second position 148, thereby exposing the grasper magnet 150 and allowing contact between the grasper magnet 150 and a magnetic suture 200 attracted thereto. The translation of the retriever body 120 results in translation of the grasper arm 136. The translation of the retriever body 120 in the first direction can be translation of the retriever body 120 within the needle lumen 116 in a direction from the proximal end 104 of the suture retrieval needle 102 toward the distal end 106 of the suture retrieval needle 102. When the grasper arm 136 is in the first position 146 the grasper magnet 150 can be disposed entirely inside the needle lumen 116, and thus sequestered within the needle lumen 116. In accordance with these embodiments, such translation of the retriever body 120 within the needle lumen 116 in the first direction can move the grasper magnet 150 from inside the needle lumen 116 to outside the needle lumen 116, thus exposing the grasper magnet 150.

The grasper arm 136 can be sufficiently stiff so that translation of the retriever body 120 within the needle lumen 116 in the first direction moves the grasper arm 136 from inside the needle lumen 116 to outside the needle lumen 116, thus exposing the grasper magnet 150. This may be accomplished by making the grasper arm 136 sufficiently stiff so as to moveable by translation of retriever body 120.

As shown by comparison of FIG. 5 with FIG. 10 for the first embodiment 1001, comparison of FIG. 12 with FIG. 14 for the second embodiment 1002, and comparison of FIG. 16 with FIG. 18 for the third embodiment 1003, translation of the retriever body 120 within the needle lumen 116 in a second direction opposite the first direction along the needle body axis 110 causes the grasper arm 136 to move from the second position 148 to the first position 146, thereby sequestering the grasper magnet 150 and grasping the magnetic suture 200 within the needle lumen 116. The translation of the retriever body 120 in the second direction can be translation of the retriever body 120 within the needle lumen 116 in a direction from the distal end 106 of suture retrieval needle 102 toward the proximal end 104 of the suture retrieval needle 102. Such translation of the retriever body 120 within the needle lumen 116 in the second direction can move the grasper magnet 150 from outside the needle lumen 116 to inside the needle lumen 116, thus sequestering the grasper magnet 150 again and grasping the magnetic suture 200 within the needle lumen 116.

This can be accomplished as follows. Because the grasper magnet 150 is closer to the distal end 106 of the suture retrieval needle 102 than is the distal end 144 of the grasper arm 136 while the grasper arm 136 is in the second position 148, when a suture magnet 202 of a magnetic suture 200 contacts the grasper magnet 150 and the retriever body 120 is translated in the second direction to the first position 146, the grasper magnet 150 and the suture magnet 202 of the magnetic suture 200 enter the needle lumen 116 before the distal end 144 of the grasper arm 136 does. Once the distal end 144 of the grasper arm 136 has followed the suture magnet 202 into the needle lumen 116, the suture magnet 202 cannot exit the needle lumen 116 while the distal end 144 of the grasper arm 136 remains in the needle lumen 116. The grasper arm 136 blocks exit of the suture magnet 202, thereby mechanically capturing the magnetic suture 200. The suture magnet 202 of the magnetic suture 200 thus can be grasped by the grasper arm 136 as the magnet-assisted suture grasper 100 is used to pull the magnetic suture 200 through soft tissue of a patient. The grasper arm 136 is sufficiently strong to resist the frictional drag that results from pulling the magnetic suture 200 through the soft tissue.

As noted above, the grasper arm 136 comprises a proximal end 138, a proximal-to-intermediate portion 140, a distal portion 142, and a distal end 144. Also as noted, the grasper magnet 150 is disposed adjacent the proximal-to-intermediate portion 140 of the grasper arm 136. The distal portion 142 of the grasper arm 136 has a length and orientation sufficient to allow the suture magnet 202 of a magnetic suture 200 to fit between the grasper magnet 150 and the distal end 144 of the grasper arm 136 when the grasper arm 136 is in the second position 148, so that the suture magnet 202 of the magnetic suture 200 can contact the grasper magnet 150 for magnetic attraction, and when the grasper arm 136 has been returned to the first position 146, so that the suture magnet 202 of the magnetic suture 200 can fit within the needle lumen 116 along with the grasper magnet 150 and the grasper arm 136 for mechanical capture. The proximal-to-intermediate portion 140 of the grasper arm 136 adjacent to which the grasper magnet 150 is disposed can be any portion of the grasper arm 136 distal to the proximal end 138 and proximal to the distal portion 142, so long as sufficient space is provided for a suture magnet 202 to fit between the grasper magnet 150 and the distal end 144 of the grasper arm 136.

The grasper arm 136 can grasp a magnetic suture 200 for example by serving as a mechanical plug by addition of an enlarged distal terminus 162. The enlarged distal terminus 162 can be sized to allow contact between the grasper magnet 150 and a suture magnet 202 of a magnetic suture 200 attracted thereto when the grasper arm 136 is in the second position 148 outside the needle lumen 116. The enlarged distal terminus 162 also can be sized such that when the grasper arm 136 is in the first position 146 inside the needle lumen 116, a suture 204 of the magnetic suture 200 can pass by the enlarged distal terminus 162, but the suture magnet 202 of the magnetic suture 200 cannot.

This can be accomplished by use of an enlarged distal terminus 162 corresponding to a partial spheroid end comprising a hook, which can create a blockage within the needle lumen 116 by which the suture magnet 202 of the magnetic suture 200 cannot pass. The enlarged partial spheroid feature can have a size, e.g., a diameter or a width transverse to the needle body axis 110, corresponding for example to about 10% to about 90% the inner diameter of the needle lumen 116. This can be accomplished various additional ways too. For example, the enlarged distal terminus 162 can be an enlarged hook alone or an enlarged spheroid alone. These provide an advantage of being simpler to manufacture than a partial spheroid end comprising a hook. The enlarged hook alone and the enlarged spheroid alone also can have a size, e.g., a diameter or a width transverse to the needle body axis 110, corresponding for example to about 10% to about 90% the inner diameter of the needle lumen 116. Alternatively, two or more grasper arms 136 could be employed. This provides an advantage that multiple grasper arms 136 of a smaller cross-section could be employed to obtain an equivalent strength to a single grasper arm 136 of a larger cross-section, but the multiple grasper arms 136 would not intrude as far into the needle lumen 116, allowing for maximization of the diameter of the grasper magnet 150. A similar effect could be achieved by using a grasper arm 136 with a non-round profile. Mechanical plugs corresponding to an enlarged partial spheroid comprising a hook, an enlarged hook, and an enlarged spheroid alone can be melt formed from the grasper arm 136 or may a separate mechanical plug element that is attached, such as by swaging, or by employing an adhesive. The mechanical plug element also does not need to be spheroid, as its shape is not critical to its function. Thus the mechanical plug element alternatively could be shaped as, for example, an elongated cylinder, or a pyramid, or a toroid. Also alternatively, the grasper arms 136 could simply terminate in a pig-tailed coil, forming a basket-like shape.

The grasper arm 136 also can grasp a magnetic suture 200 for example by forming a grasper arm loop. This can be accomplished for example by using first and second grasper arms 136 that are connected at their distal ends 144, thereby forming a grasper arm loop. The grasper arm loop can have a length and shape such that the grasper arm loop circumscribes an area sufficiently large to allow contact between the grasper magnet 150 and a suture magnet 202 of a magnetic suture 200 attracted thereto when the grasper arm loop is in the second position 148. For example, the grasper arm loop can have a length and shape such that the corresponding circumscribed area is sufficiently large to fit both the grasper magnet 150 and the suture magnet 202 when the grasper magnet 150 and the suture magnet 202 are in contact at their respective poles. The grasper arm loop also can be sized such that the grasper arm loop has a thickness, e.g., a mean diameter, sufficiently great to block the suture magnet 202 of the magnetic suture 200 from exiting the needle lumen 116 through the distal hole 114 of the suture retrieval needle 102 when the grasper arm loop is in the first position 146.

Accordingly, as shown in FIG. 5, FIG. 12, FIG. 16, and FIG. 20, and FIG. 21 for the first to fifth embodiments 1001-1005, respectively, in some embodiments the grasper arm 136 further comprises an enlarged distal terminus 162 at the distal end 144 of the grasper arm 136. In these embodiments, the grasper arm 136 is reversibly moveable between the first position 146 and the second position 148 based on translation of the grasper arm 136 from inside of the needle lumen 116 to outside of the needle lumen 116 through the distal hole 114 of the needle body 108. In these embodiments, the enlarged distal terminus 162 at the distal end 144 of the grasper arm 136 has a size sufficiently small to allow contact between the grasper magnet 150 and a suture magnet 202 of a magnetic suture 200 attracted thereto when the grasper arm 136 is in the second position 148 and to allow a suture 204 of the magnetic suture 200 to pass when the grasper arm 136 is in the first position 146, and sufficiently large to block the suture magnet 202 of the magnetic suture 200 from exiting the needle lumen 116 through the distal hole 114 of the needle body 108 when the grasper arm 136 is in the first position 146. These embodiments can be advantageous for being relatively simple to manufacture in comparison, for example, to embodiments including multiple grasper arms 136. In some examples of these embodiments, the size of the enlarged distal terminus 162 is about 10% to about 90% the inner diameter of the needle lumen 116. For example, the enlarged distal terminus 162 can have a diameter or a width transverse to the needle body axis 110 that is about 10% to about 90% the inner diameter of the needle lumen 116.

Figure 22:
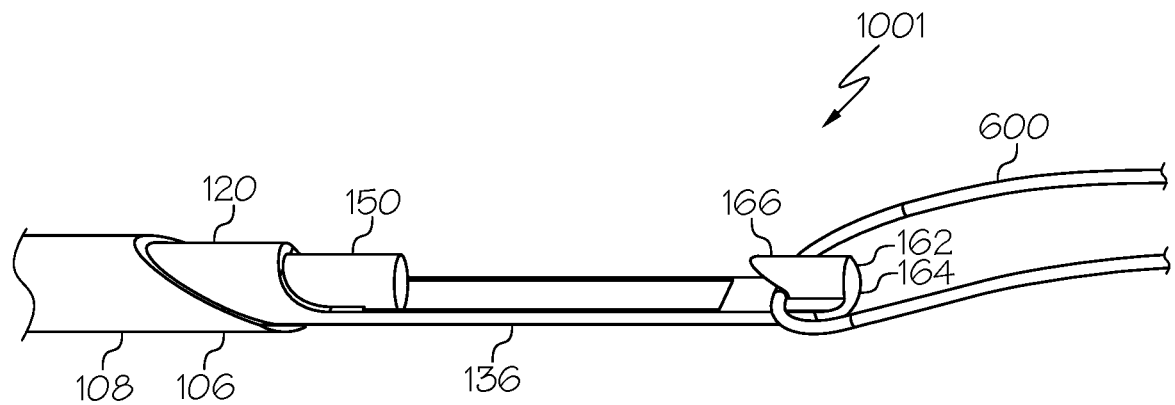
FIG. 22 is a perspective view of the distal end of the magnet-assisted suture grasper of FIG. 1 in which the enlarged distal terminus at the distal end of the grasper arm comprises a hook and a nonmagnetic suture has been captured by the hook.
Figure 23:
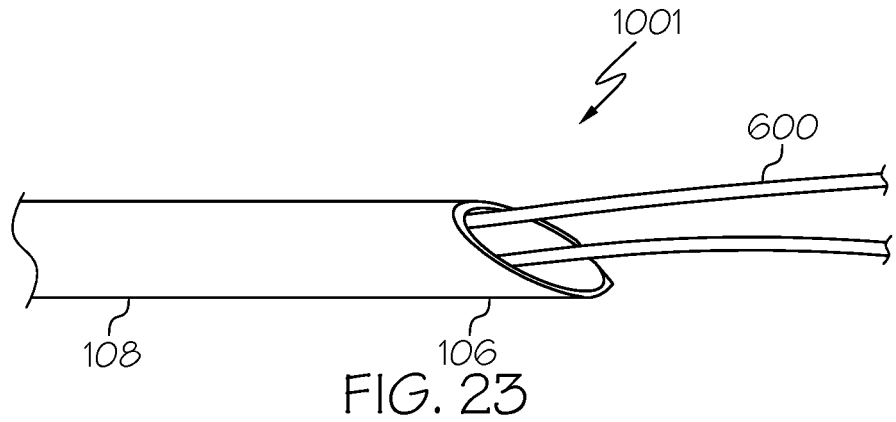
FIG. 23 is a perspective view of the distal end of the magnet-assisted suture grasper of FIG. 1 in which the grasper arm is in the first position and a nonmagnetic suture has been captured within the needle lumen of the suture retrieval needle.
Figure 24:
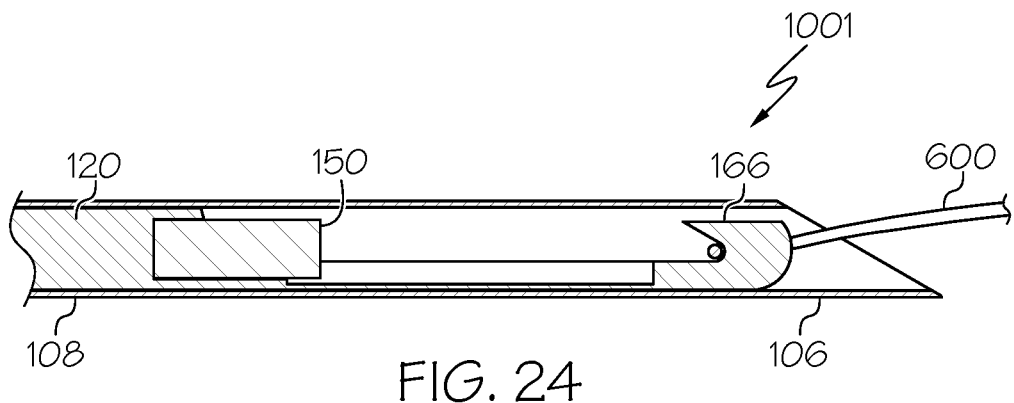
FIG. 24 is a sectional view of the distal end of the magnet-assisted suture grasper of FIG. 1 in which the grasper arm is in the first position and a nonmagnetic suture has been captured within the needle lumen of the suture retrieval needle.

With reference to FIG. 5 and FIG. 20 for the first embodiment 1001 and the fourth embodiment 1004, respectively, in some of these embodiments the enlarged distal terminus 162 comprises a partial spheroid 164 comprising a hook 166. Also, with reference to FIG. 12 for second embodiment 1002, in some of these embodiments the enlarged distal terminus 162 comprises a hook 166 alone. As shown in FIGS. 22-24 for the first embodiment 1001, these embodiments comprising a hook 136 also can be advantageous for allowing capture of nonmagnetic sutures 600. With reference to FIG. 16 and FIG. 21 for the third embodiment 1003 and the fifth embodiment 1005, in some of these embodiments the enlarged distal terminus 162 comprises a spheroid 168 alone. In some examples of these embodiments, the size of the enlarged distal terminus 162, such as the partial spheroid 164 comprising a hook 166, the hook 166 alone, or the spheroid 168 alone, is about 10% to about 90% the inner diameter of the needle lumen 116. For example, the enlarged distal terminus 162 can have a diameter or a width transverse to the needle body axis 110 that is about 10% to about 90% the inner diameter of the needle lumen 116.

Also, as shown in FIG. 21 for the fifth embodiment 1005, in some embodiments the grasper arm 136 is a first grasper arm 136. In these embodiments, the magnet-assisted suture grasper 100 further comprises a second grasper arm 136 comprising a proximal end 138, a proximal-to-intermediate portion 140, a distal portion 142, and a distal end 144, the second grasper arm 136 extending from the distal end 124 of the retriever body 120 and being reversibly moveable between the first position 146 and the second position 148. In these embodiments, the first and second grasper arms 136 are connected at their distal ends 144, thereby forming a grasper arm loop. In these embodiments, the first and second grasper arms 136 further comprise an enlarged distal terminus 162 at the distal ends 144 of the first and second grasper arms 136. In these embodiments, the grasper arm loop 136 is reversibly moveable between the first position 146 and the second position 148 based on translation of the grasper arm loop from inside of the needle lumen 116 to outside of the needle lumen 116 through the distal hole 114 of the needle body 108. In these embodiments, the grasper arm loop circumscribes an area sufficiently large, and the enlarged distal terminus 162 at the distal ends 144 of the first and second grasper arms 136 has a size sufficiently small, to allow contact between the grasper magnet 150 and a magnetic suture 202 of the magnetic suture 200 attracted thereto when the grasper arm loop is in the second position 148. In these embodiments, the enlarged distal terminus 162 at the distal ends 144 of the first and second grasper arms 136 has a size sufficiently small to allow a suture 204 of a magnetic suture 200 to pass when the grasper arm loop is in the first position 146. In these embodiments, the enlarged distal terminus 162 at the distal ends 144 of the first and second grasper arms 136 has a size sufficiently large to block the suture magnet 202 of the magnetic suture 200 from exiting the needle lumen 116 through the distal hole 114 of the needle body 108 when the grasper arm loop is in the first position 146. These embodiments are advantageous for allowing use of grasper arms 126 having relatively smaller diameters. In some examples of these embodiments, the size of the enlarged distal terminus 162 is about 10% to about 90% the inner diameter of the needle lumen 116. For example, the enlarged distal terminus 162 can have a diameter or a width transverse to the needle body axis 110 that is about 10% to about 90% the inner diameter of the needle lumen 116.

Also in some embodiments the grasper arm 136 is a first grasper arm 136. In these embodiments, the magnet-assisted suture grasper 100 further comprises a second grasper arm 136 comprising a proximal end 138, a proximal-to-intermediate portion 140, a distal portion 142, and a distal end 144, the second grasper arm 136 extending from the distal end 124 of the retriever body 120 and being reversibly moveable between the first position 146 and the second position 148. In these embodiments, the first grasper arm 146 further comprises an enlarged distal terminus 162 at the distal end 144 of the first grasper arm 136. In these embodiments, the second grasper arm 136 further comprises an enlarged distal terminus 162 at the distal end of the second grasper arm 136. In these embodiments, the first and second grasper arms 136 are reversibly moveable between the first position 146 and the second position 148 based on translation of the first and second grasper arms 136 from inside of the needle lumen 116 to outside of the needle lumen 116 through the distal hole 114 of the needle body 108. In these embodiments, the enlarged distal termini 162 of the first and second grasper arms 136 have sizes sufficiently small to allow contact between the grasper magnet 150 and a suture magnet 202 of a magnetic suture 200 attracted thereto when the first and second grasper arms 136 are in the second position 148 and to allow a suture 204 of the suture magnet 200 to pass when the first and second grasper arms 136 are in the first position 146, and sufficiently large to block the suture magnet 202 of the magnetic suture 200 from exiting the needle lumen 116 through the distal hole 114 of the needle body 108 when the first and second grasper arms 136 are in the first position 146. In some of these embodiments, the magnet-assisted suture grasper 100 can further comprise at least one additional grasper arm 136 extending distally from the retriever body 120. These embodiments can be advantageous by allowing for a larger grasper magnet 150 than an equivalent single grasper arm 136 having the same total cross-sectional area. This is because the two or more grasper arms 136 can be positioned radially about the inner surface of a needle lumen 116, allowing for the cross-sectional area of the grasper arms 136 to be distributed unequally. This leaves more usable space for the grasper magnet 150 to occupy. For example, a dual grasper arm design provides a 12% increase in usable space over a single grasper arm design, while a quadruple grasper arm design provides a 20% increase in usable space over the single grasper arm design. Moreover, the same effect could be achieved by using a non-round profile for the grasper arm 136.

Also in some embodiments the grasper arm 136 is a first grasper arm 136. In these embodiments, the magnet-assisted suture grasper 100 further comprises a second grasper arm 136 comprising a proximal end 138, a proximal-to-intermediate portion 140, a distal portion 142, and a distal end 144, the second grasper arm 136 extending from the distal end 124 of the retriever body 120 and being reversibly moveable between the first position 146 and the second position 148. In these embodiments, the first and second grasper arms 136 are connected at their distal ends 144, thereby forming a grasper arm loop. In these embodiments, the grasper arm loop 136 is reversibly moveable between the first position 146 and the second position 148 based on translation of the grasper arm loop from inside of the needle lumen 116 to outside of the needle lumen 116 through the distal hole 114 of the needle body 108. In these embodiments, the grasper arm loop circumscribes an area sufficiently large to allow contact between the grasper magnet 150 and a suture magnet 202 of a magnetic suture 200 attracted thereto when the grasper arm loop is in the second position 148. In some of these embodiments, the grasper arm loop has a thickness sufficiently great to block the suture magnet 202 of the magnetic suture 200 from exiting the needle lumen through the distal hole 114 of the needle body 108 when the grasper arm loop is in the first position 146. For these embodiments in which the grasper arms 136 do not comprise an enlarged distal terminus 162 at their distal ends 144, advantages include ease of manufacture and the possibility of using a larger grasper magnet 150.

Also in some embodiments the grasper arm 136 is a first grasper arm 136. In these embodiments, the magnet-assisted suture grasper 100 further comprises a second grasper arm 136 comprising a proximal end 138, a proximal-to-intermediate portion 140, a distal portion 142, and a distal end 144, the second grasper arm 136 extending from the distal end 124 of the retriever body 120 and being reversibly moveable between the first position 146 and the second position 148. In these embodiments, the first grasper arm 136 further comprises an enlarged distal terminus 162 at the distal end 144 of the first grasper arm 136. In these embodiments, the second grasper arm 136 further comprises an enlarged distal terminus 162 at the distal end 144 of the second grasper arm 136. In these embodiments, the first and second grasper arms 136 are reversibly moveable between the first position 146 and the second position 148 based on translation of the first and second grasper arms 136 from inside of the needle lumen 116 to outside of the needle lumen 116 through the distal hole 114 of the needle body 108. In these embodiments, the proximal-to-intermediate portions 140 of the first and second grasper arms 136 are substantially parallel to the needle body axis 110 when the first and second grasper arms 136 are in the first position 146. In these embodiments, at least one of the first or second grasper arms 136 pivots reversibly outwardly from the needle body axis 110 sufficiently far to allow contact between the grasper magnet 150 and a suture magnet 202 of a magnetic suture 200 attracted thereto when the first and second grasper arms 136 are in the second position 148. In these embodiments, the enlarged distal termini 162 of the first and second grasper arms 136 have sizes sufficiently small to allow a suture 204 of the magnetic suture 200 to pass when the first and second grasper arms 136 are in the first position 146, and sufficiently large to block the suture magnet 202 of the magnetic suture 200 from exiting the needle lumen 116 through the distal hole 114 of the needle body 108 when the first and second grasper arms 136 are in the first position 146. In these embodiments, the two grasper arms 136 can function as a pincer that includes a crotch. In such embodiments, the grasper magnet 150 can advantageously be attached to the crotch of the pincer to attract and hold a magnetic suture 200 in place, thereby easing capture by the pincer. In some examples of these embodiments, both the first and second grasper arms 136 pivot reversibly outwardly from the needle body axis 110 when the first and second grasper arms 136 are in the second position 148.

Considering the first embodiment 1001 of the magnet-assisted suture grasper 100 further, in some embodiments the magnet-assisted suture grasper 100 further comprises the hub 119 of the suture retrieval needle 102 and a suture retriever needle handle attached to the retriever body 120. This is advantageous for improving the ergonomics of the magnet-assisted suture grasper 100 by allowing for single-handed operation. The suture retriever needle handle would preferentially include a non-axisymmetric design so as to rotationally fix the suture retriever needle handle and the retriever body 120.

Also in some embodiments the magnet-assisted suture grasper 100 further comprises a return mechanism, such as a spring. In these embodiments, the retriever body 120 can be attached directly to the suture retriever needle handle, so that when the suture retriever needle handle is depressed, the retriever body 120 is advanced, which in turn advances the grasper arm 136 and the grasper magnet 150 from the needle lumen 116. When the suture retriever needle handle is released, the spring returns the suture retriever needle handle to the original position. This returns the grasper arm 136 and the grasper magnet 150 to the needle lumen 116.

The embodiment 1001 of the magnet-assisted suture grasper 100 can be operated as follows.

After a magnetic suture 200 has been deposited inside a patient, the suture retrieval needle 102 is introduced into the patient to gain access to the site of the suture. The retriever body 120 is used to advance the grasper arm 136 and the grasper magnet 150 through the needle lumen 116 of the suture retrieval needle 102 until the grasper arm 136 and the grasper magnet 150 exit the needle lumen 116, extending past the distal hole 114 of the suture retrieval needle 102. The grasper arm 136 and the grasper magnet 150 are brought near the suture magnet 202 of the magnetic suture 200, so that the magnetic fields of the grasper magnet 150 and the suture magnet 202 can interact. The attractive force between the grasper magnet 150 and the suture magnet 202 pulls the suture magnet 202 towards the grasper magnet 150 and brings them into contact and axial alignment.

Then the retriever body 120 is used to pull the grasper arm 136 and the grasper magnet 150 back inside the needle lumen 116 of the suture retrieval needle 102. The attractive force between the grasper magnet 150 and the suture magnet 202 allows the grasper magnet 150 to tow the suture magnet 202, and the attached suture 204, along with it. The retriever body 120 is pulled back until the grasper magnet 150 and the suture magnet 202 are brought entirely inside the needle lumen 116. At this point, the magnetic suture 200 cannot escape the suture retrieval needle 102, because the distal end 144 of the grasper arm 136 blocks the exit path. The proximal end 138 of the grasper arm 136 is attached to the retriever body 120, so the grasper arm 136 is not moved by the suture 204.

Once the magnetic suture 200 has been captured, the magnet-assisted suture grasper 100 can be used to pull or push the magnetic suture 200 to a new location. The grasper arm 136 allows the magnet-assisted suture grasper 100 to hold the magnetic suture 200 securely, even when the magnetic suture 200 is heavily loaded to the point that the load exceeds the attractive force between grasper magnet 150 and the suture magnet 202. The grasper arm 136 prevents the suture magnet 202 of the magnetic suture 200 from being pulled back out of the needle lumen 116, even when the force applied exceeds the strength of attraction between the grasper magnet 150 and the suture magnet 202.

Once the magnetic suture 200 has been passed to the desired location, the magnetic suture 200 can be released from the magnet-assisted suture grasper 100. To release the magnetic suture 200, the retriever body 120 is used to advance the grasper arm 136, the grasper magnet 150, and the suture magnet 202 out of the needle lumen 116, and the suture 204 can then be pulled to disconnect the grasper magnet 150 and the suture magnet 202.

Figure 31:
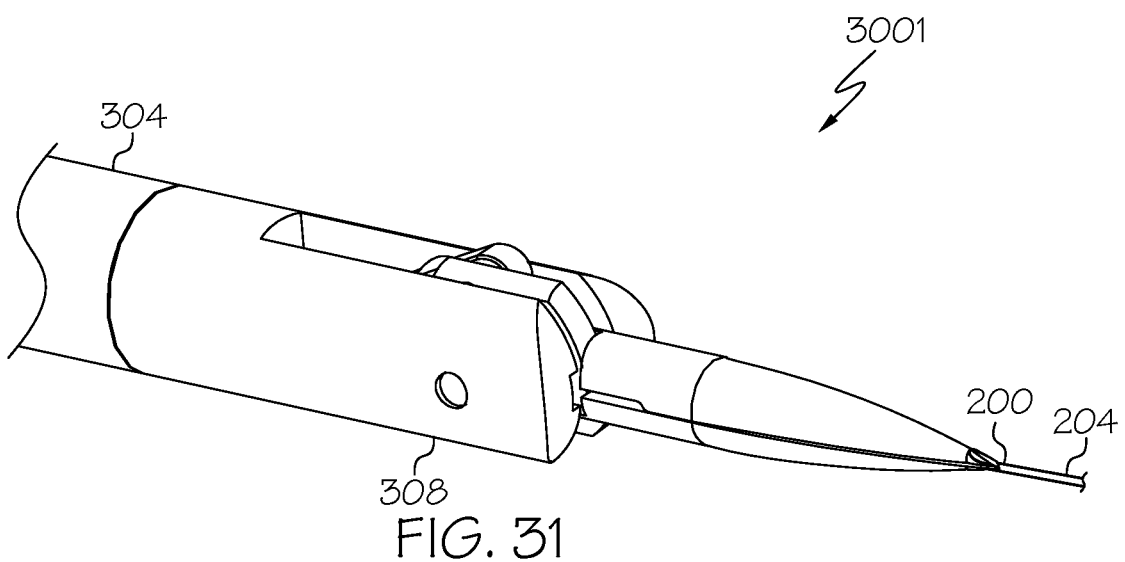
FIG. 31 is a perspective view of the distal end of the magnet-assisted suture grasper of FIG. 25, in which the first grasper jaw is in a position in which the grasper magnet is being sequestered in a recess between the first and second grasper jaws, termed the first position, and the grasper magnet is attracting the magnetic suture and in contact with the magnetic suture, such that the magnetic suture has been captured within the recess of the magnet-assisted suture grasper.
Figure 32:
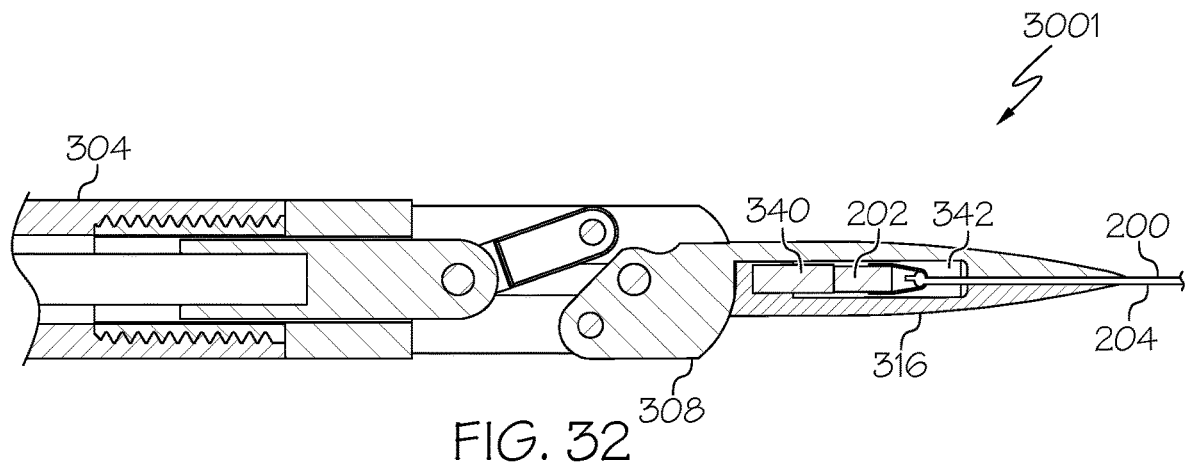
FIG. 32 is a sectional view of the distal end of the magnet-assisted suture grasper of FIG. 25, in which the first grasper jaw is in a position in which the grasper magnet is being sequestered in a recess between the first and second grasper jaws, termed the first position, and the grasper magnet is attracting the magnetic suture and in contact with the magnetic suture, such that the magnetic suture has been captured within the recess of the magnet-assisted suture grasper.
Figure 33:
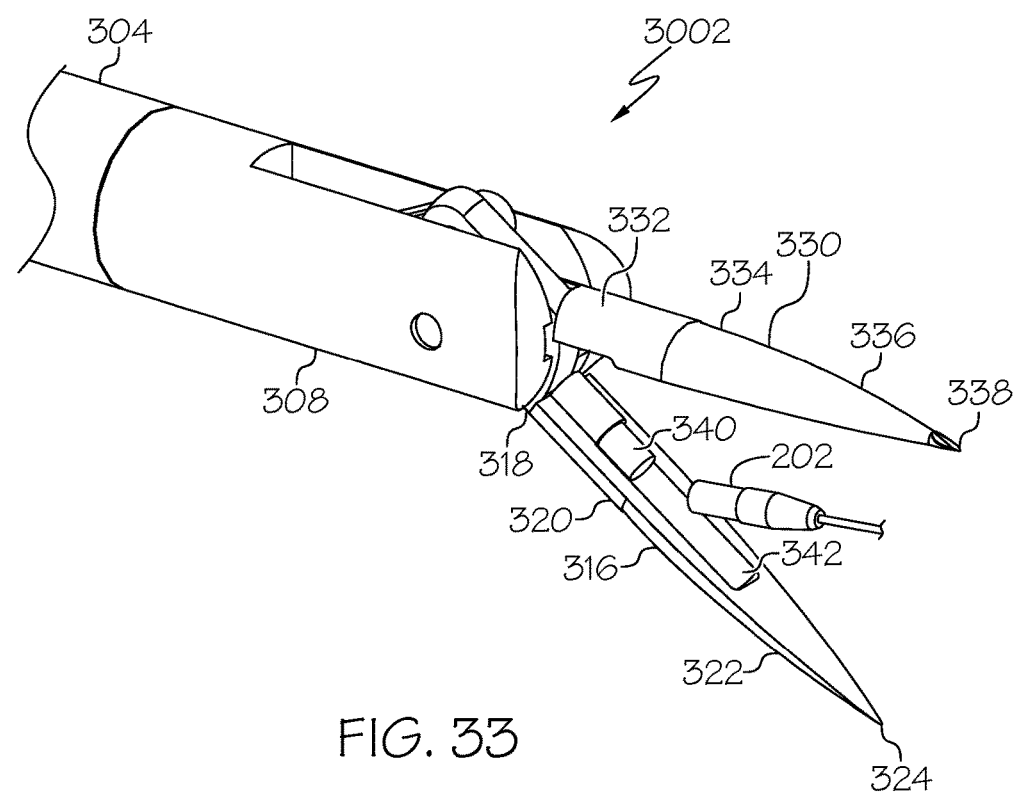
FIG. 33 is a perspective view of a first alternate embodiment of the magnet-assisted suture grasper of FIG. 25, in which the first grasper jaw is in the second position, the second grasper jaw is not pivotally moveable relative to the stem, and the grasper magnet is attracting a magnetic suture.
Figure 34:
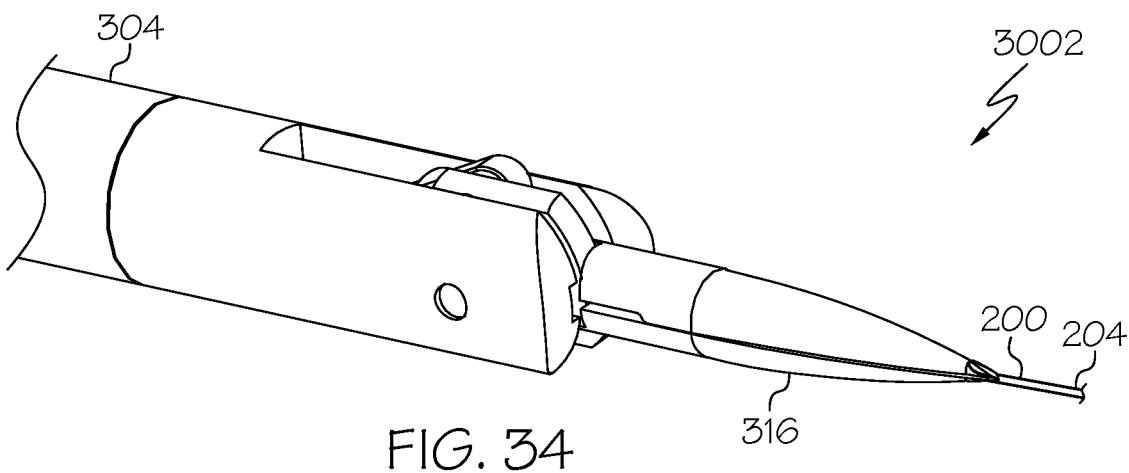
FIG. 34 is a perspective view of the first alternate embodiment of the magnet-assisted suture grasper of FIG. 25, in which the first grasper jaw is in the first position, the grasper magnet is attracting the magnetic suture and in contact with the magnetic suture, such that the magnetic suture has been captured within the recess of the magnet-assisted suture grasper.
Figure 35:
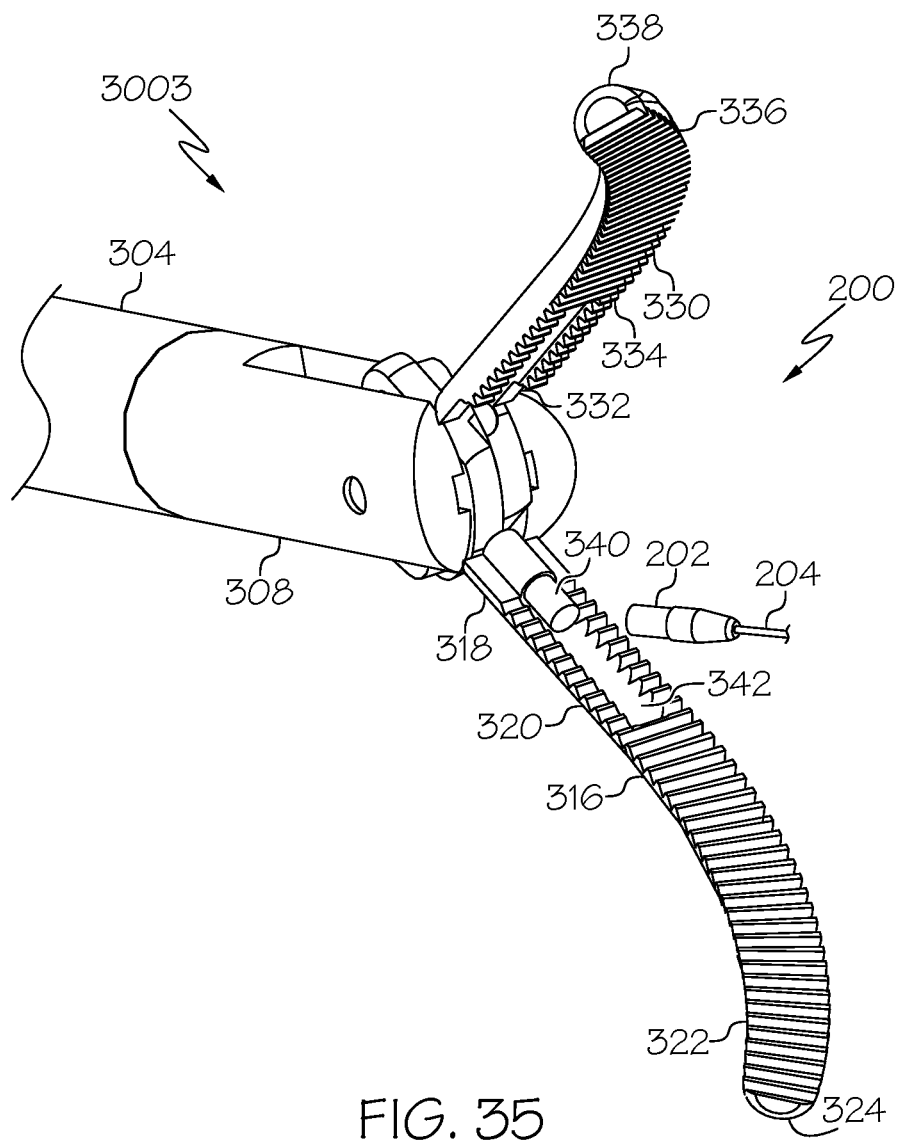
FIG. 35 is a perspective view of a second alternate embodiment of the magnet-assisted suture grasper of FIG. 25, in which the distal ends of the first and second grasper jaws do not have sharp tips, the first grasper jaw is in the second position, the second grasper jaw has pivoted away from the first grasper jaw, and the grasper magnet is attracting a magnetic suture.
Figure 36:
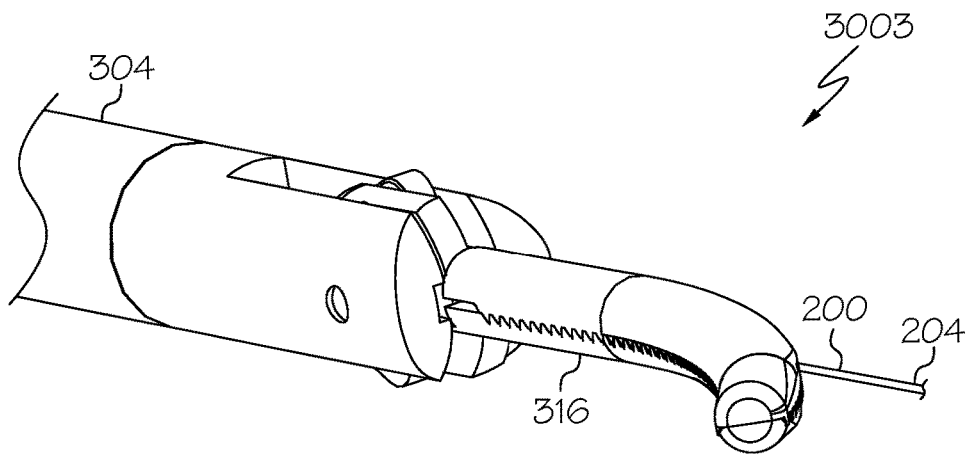
FIG. 36 is a perspective view of the second alternate embodiment of the magnet-assisted suture grasper of FIG. 25, in which the first grasper jaw is in the first position, the second grasper jaw has pivoted toward the first grasper jaw, and the grasper magnet is attracting the magnetic suture and in contact with the magnetic suture, such that the magnetic suture has been captured within the recess of the magnet-assisted suture grasper.
Figure 37:
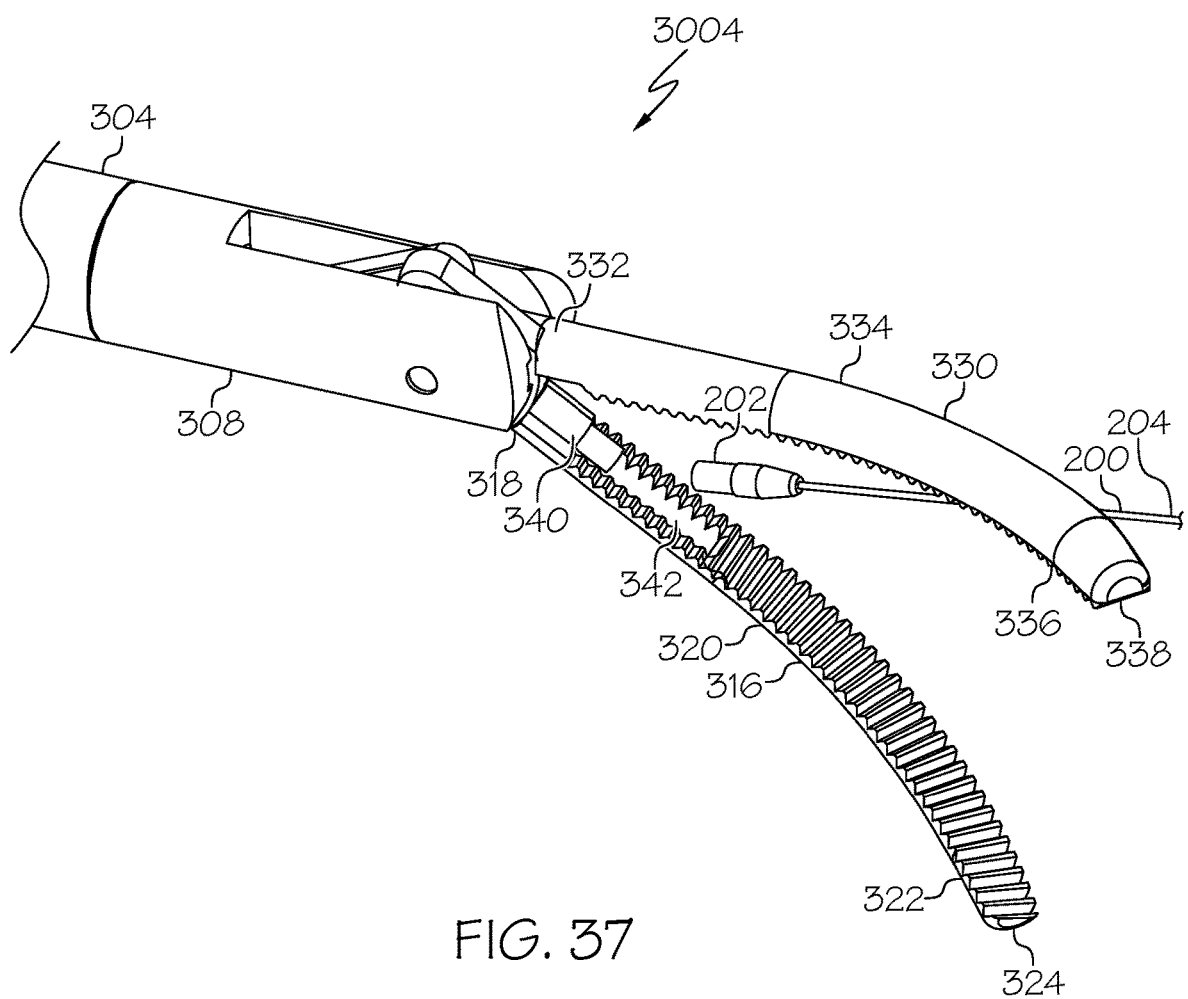
FIG. 37 is a perspective view of a third alternate embodiment of the magnet-assisted suture grasper of FIG. 25, in which the distal ends of the first and second grasper jaws do not have sharp tips, the first grasper jaw is in the second position, the second grasper jaw is not pivotally moveable relative to the stem, and the grasper magnet is attracting a magnetic suture.
Figure 38:
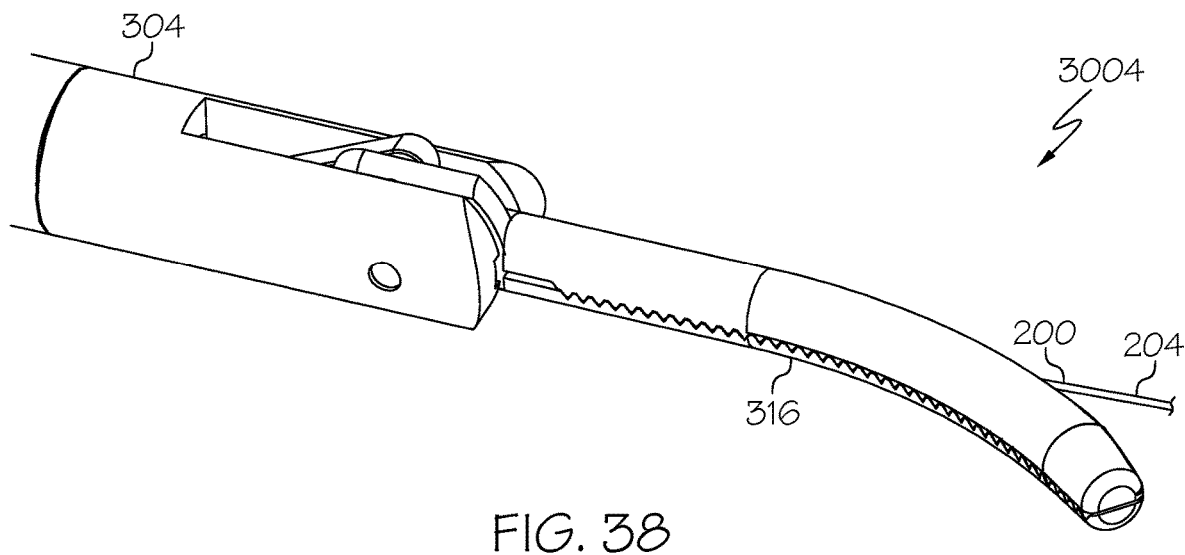
FIG. 38 is a perspective view of the third alternate embodiment of the magnet-assisted suture grasper of FIG. 25, in which the first grasper jaw is in the first position and the grasper magnet is attracting the magnetic suture and in contact with the magnetic suture, such that the magnetic suture has been captured within the recess of the magnet-assisted suture grasper.
Figure 39:
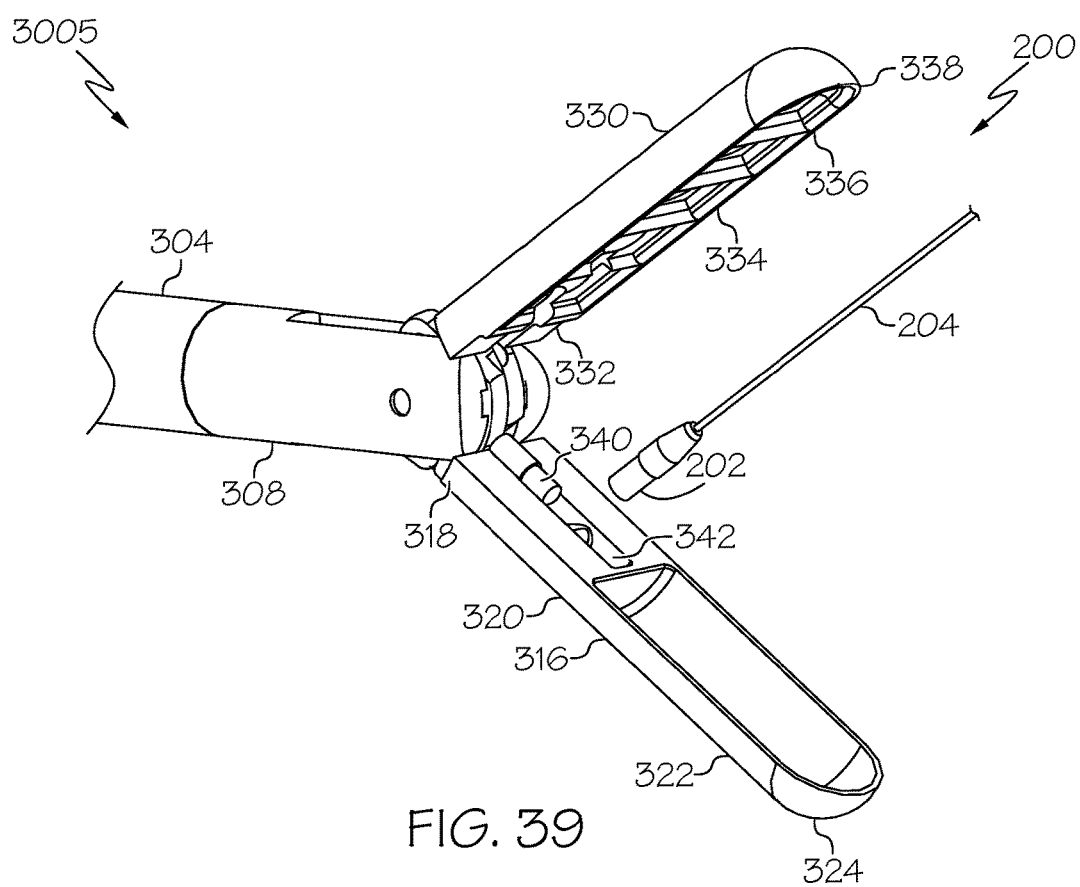
FIG. 39 is a perspective view of a fourth alternate embodiment of the magnet-assisted suture grasper of FIG. 25, in which the distal ends of the first and second grasper jaws do not have sharp tips, the first grasper jaw is in the second position, the second grasper jaw has pivoted away from the first grasper jaw, and the grasper magnet is attracting a magnetic suture.
Figure 40:
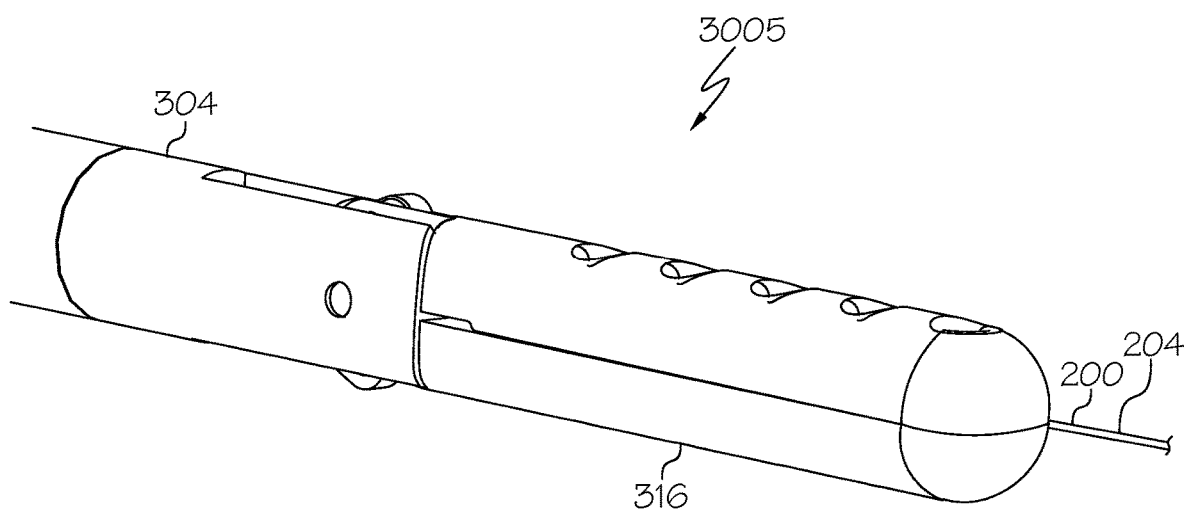
FIG. 40 is a perspective view of the fourth alternate embodiment of the magnet-assisted suture grasper of FIG. 25, in which the first grasper jaw is in the first position, the second grasper jaw has pivoted toward the first grasper jaw, and the grasper magnet is attracting the magnetic suture and in contact with the magnetic suture, such that the magnetic suture has been captured within the recess of the magnet-assisted suture grasper.
Figure 41:
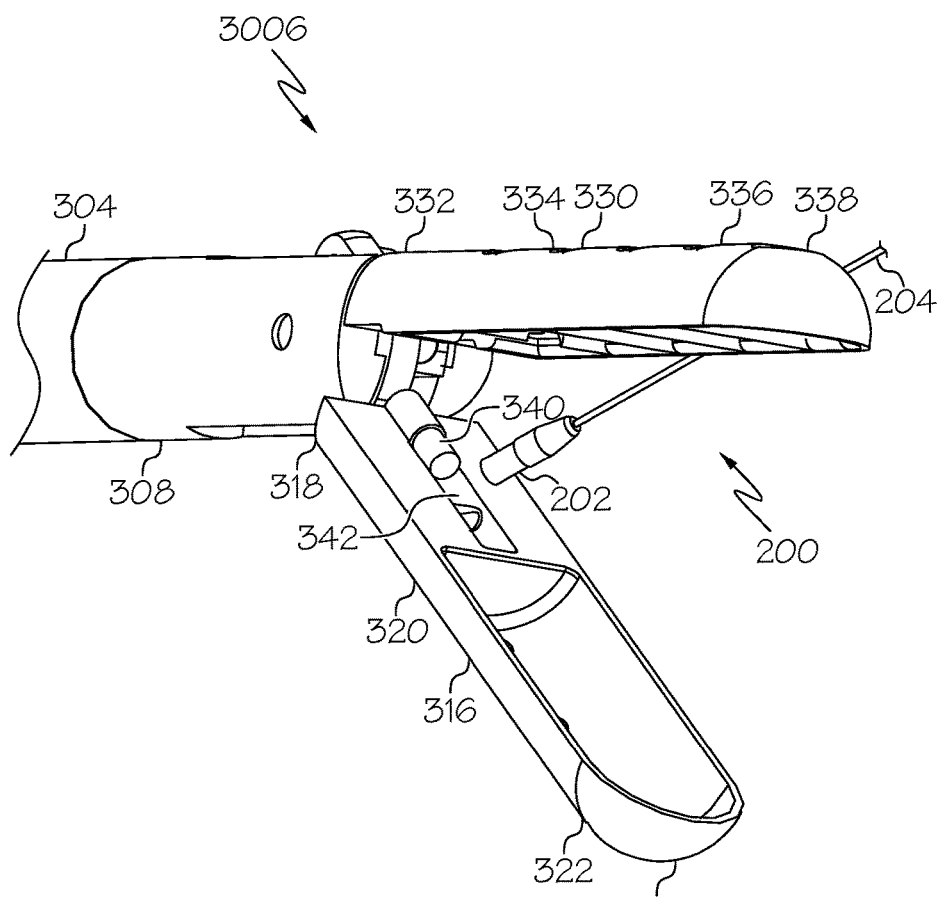
FIG. 41 is a perspective view of a fifth alternate embodiment of the magnet-assisted suture grasper of FIG. 25, in which the distal ends of the first and second grasper jaws do not have sharp tips, the first grasper jaw is in the second position, the second grasper jaw is not pivotally moveable relative to the stem, and the grasper magnet is attracting a magnetic suture.
Figure 42:
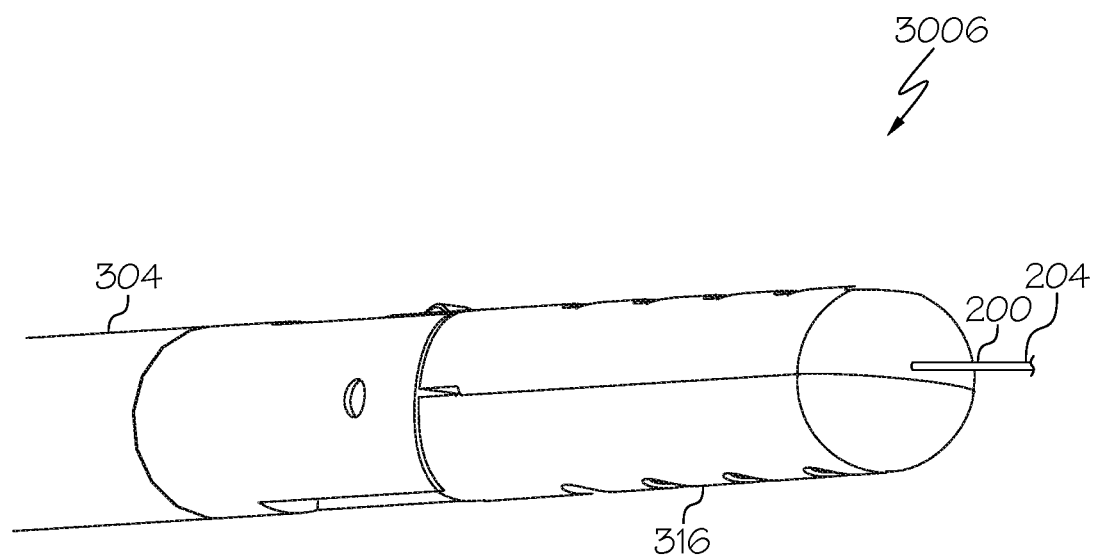
FIG. 42 is a perspective view of the fifth alternate embodiment of the magnet-assisted suture grasper of FIG. 25, in which the first grasper jaw is in the first position and the grasper magnet is attracting the magnetic suture and in contact with the magnetic suture, such that the magnetic suture has been captured within the recess of the magnet-assisted suture grasper.
Figure 50:
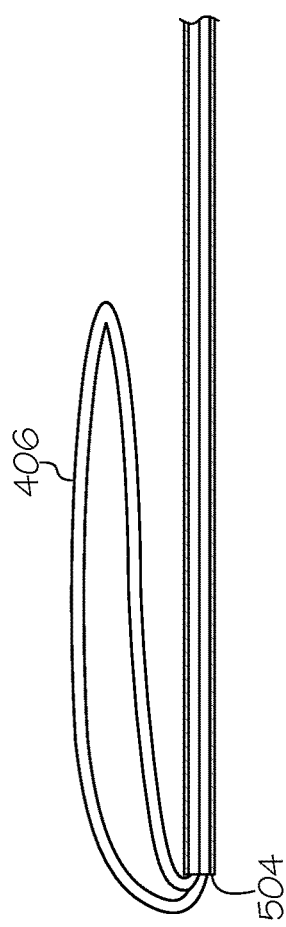
FIG. 50 is a sectional view of the loop-end of the preloaded magnetic suture cartridge of FIG. 48.
Figure 51:
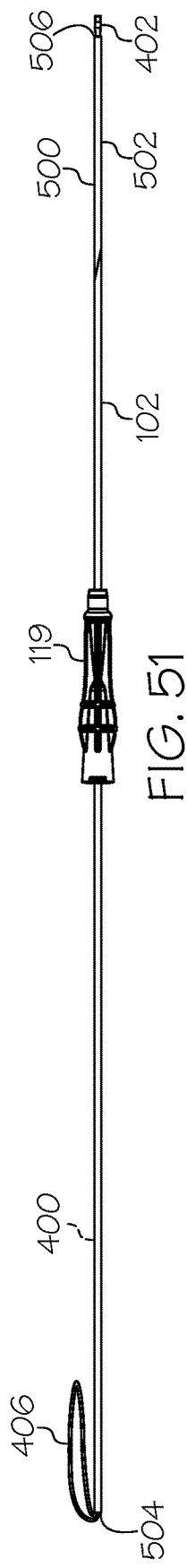
FIG. 51 is a side view of the preloaded magnetic suture cartridge of FIG. 48 in an introducer needle.
Figure 52:
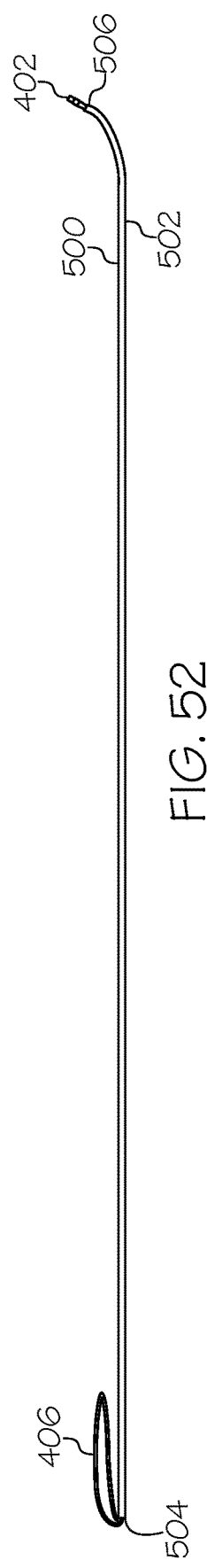
FIG. 52 is a side view of an alternate embodiment a preloaded magnetic suture cartridge as disclosed herein in which the magnet-end of the preloaded magnetic suture cartridge is curved.

FIGS. 24-32 illustrate a first embodiment 3001 of the magnet-assisted suture grasper 300 comprising (a) a handle, (b) a stem, (c) a first grasper jaw, (d) a second grasper jaw, (e) a grasper magnet, and (f) an actuator body as disclosed herein. FIG. 33 and FIG. 34 illustrate a second embodiment 3002. FIG. 35 and FIG. 36 illustrate a third embodiment 3003. FIG. 37 and FIG. 38 illustrate a fourth embodiment 3004. FIG. 39 and FIG. 40 illustrate a fifth embodiment 3005. FIG. 41 and FIG. 42 illustrate a sixth embodiment 3006. The magnet-assisted suture grasper 300 is discussed mainly with respect to the first embodiment 3001. Differences between the second through sixth embodiments 3002-3006 and the first embodiment 3001 also are discussed. Except to the extent that differences are indicated or apparent, the discussion regarding the first embodiment 3001 also applies to the second through sixth embodiments 3002-3006.

Figure 25:
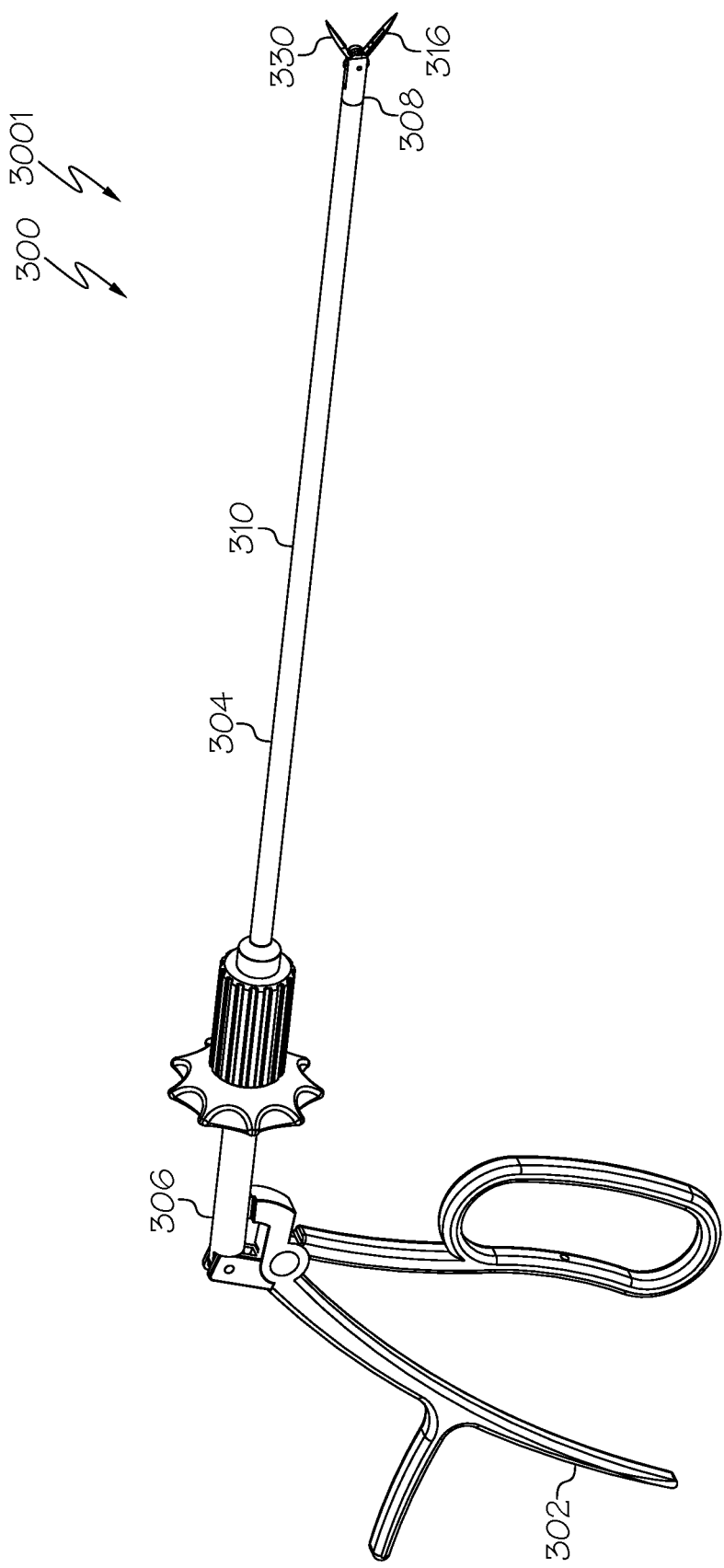
FIG. 25 is a perspective view of a second magnet-assisted suture grasper as disclosed herein. The magnet-assisted suture grasper comprises a handle, a stem, first and second grasper jaws, a grasper magnet, and an actuator body. The first grasper jaw is in a position exposing the grasper magnet from a recess formed in at least one of the first or second grasper jaws, termed the second position, as discussed herein. The second grasper jaw has pivoted away from the first grasper jaw. The distal ends of the first and second grasper jaws have sharp tips.
Figure 26:
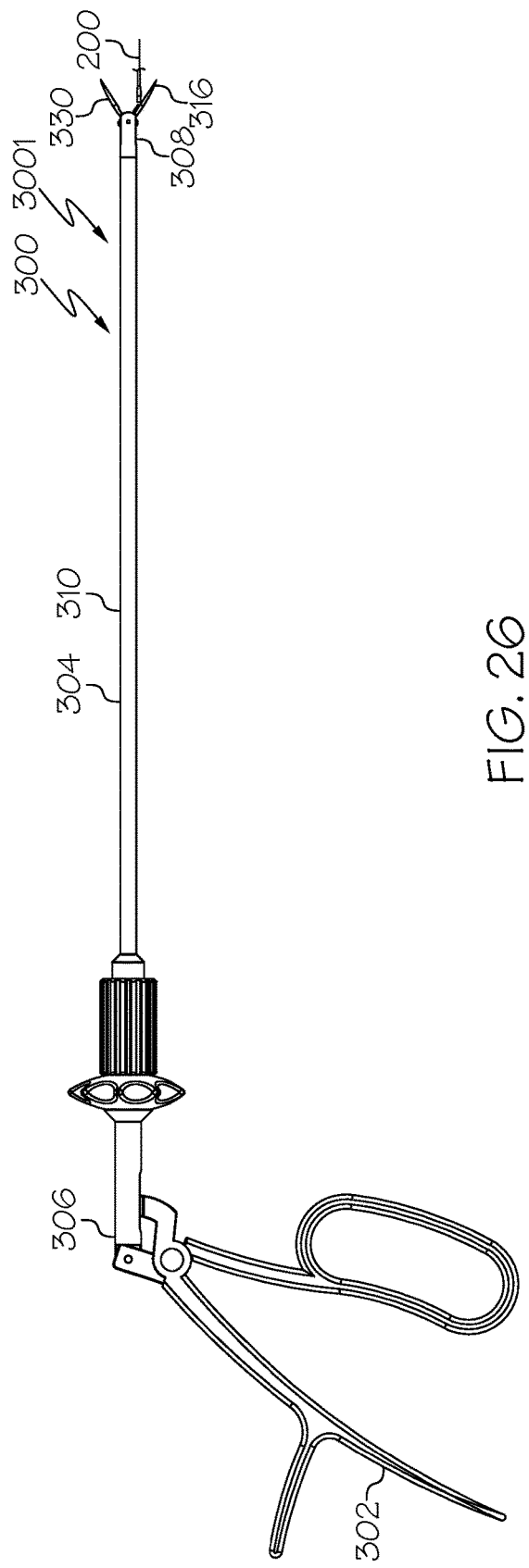
FIG. 26 is a side view of the magnet-assisted suture grasper of FIG. 25 in which the first grasper jaw is in the second position, the second grasper jaw has pivoted away from the first grasper jaw, and the grasper magnet is attracting a magnetic suture.
Figure 27:
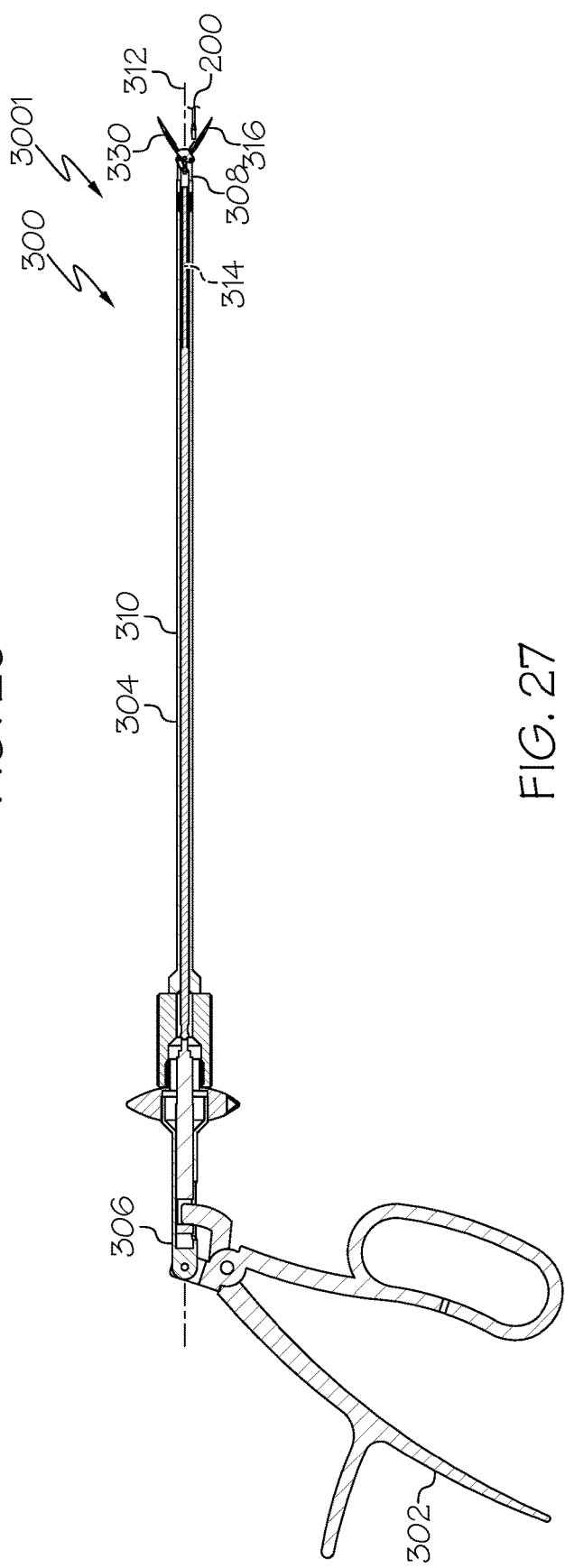
FIG. 27 is a sectional view of the magnet-assisted suture grasper of FIG. 25 in which the first grasper jaw is in the second position, the second grasper jaw has pivoted away from the first grasper jaw, and the grasper magnet is attracting a suture magnet of a magnetic suture.

As shown in FIGS. 25-27 for the first embodiment 3001, the magnet-assisted suture grasper 300 comprises a handle 302. The handle 302 is used by an operator for actuation of the magnet-assisted suture grasper 300. The handle 302 can be made of metal, such as stainless steel or titanium, or plastic or other material suitable for use of the handle 302 in actuation of the magnet-assisted suture grasper 300.

As shown in FIG. 25, FIG. 33, FIG. 35, FIG. 37, FIG. 39, and FIG. 41 for the first to sixth embodiments 3001-3006, respectively, the magnet-assisted suture grasper 300 also comprises a stem 304. As shown in FIG. 25 for the first embodiment, the stem 304 comprises a proximal end 306, a distal end 308, and a stem body 310 extending therebetween. The stem 304 is connected to the handle 302 adjacent the proximal end 306 of the stem 304. The stem body 304 defines a stem body axis 312 and includes a stem lumen 314 extending along the stem 304. The stem 304 can have a diameter sufficiently small so that the stem 304 fits through a port for accessing a site in a patient. The stem 304 can be made of metal, such as stainless steel or titanium, or plastic or other material suitable for providing structural support.

As shown in FIG. 30, FIG. 33, FIG. 35, FIG. 37, FIG. 39, and FIG. 41 for the first to sixth embodiments 3001-3006, respectively, the magnet-assisted suture grasper 300 also comprises a first grasper jaw 316 comprising a proximal end 318, a proximal-to-intermediate portion 320, a distal portion 322, and a distal end 324. The first grasper jaw 316 can be made of metal, such as stainless steel or titanium, or plastic or other suitable material for grasping a magnetic suture 200.

The first grasper jaw 316 extends from the stem 304 adjacent the distal end 308 of the stem 304 and is reversibly moveable between a first position 326 and a second position 328.

As shown in FIG. 30, FIG. 33, FIG. 35, FIG. 37, FIG. 39, and FIG. 41 for the first to sixth embodiments 3001-3006, respectively, the first grasper jaw 316 can extend from the stem 304 adjacent the distal end 308 of the stem 304, among other ways, by being pivotally connected to the stem 304 adjacent the distal end 308 of the stem 304.

As shown in FIG. 30, FIG. 33, FIG. 35, FIG. 37, FIG. 39, and FIG. 41 for the first to sixth embodiments 3001-3006, respectively, the magnet-assisted suture grasper 300 also comprises a second grasper jaw 330 comprising a proximal end 332, a proximal-to-intermediate portion 334, a distal portion 336, and a distal end 338. The second grasper jaw 330 can be made of metal, such as stainless steel or titanium, or plastic or other suitable material for grasping a magnetic suture 200.

Like the first grasper jaw 316, the first grasper jaw 330 extends from the stem 304 adjacent the distal end 308 of the stem 304. As discussed below, in some embodiments the second grasper jaw 330 also is reversibly moveable, whereas in other embodiments the second grasper 330 is not reversibly moveable. The second grasper jaw 330 can extend from the stem 304 adjacent the distal end 308 of the stem 304, among other ways, by being pivotally connected to the stem 304 adjacent the distal end 308 of the stem 304.

As shown in FIG. 30, FIG. 33, FIG. 39, and FIG. 41 for the first embodiment 3001, the second embodiment 3002, the fifth embodiment 3005, and the sixth embodiment 3006, respectively, in some embodiments the first grasper jaw 316 is straight from the proximal end 318 of the first grasper jaw 316 to the distal end 324 of the first grasper jaw 316 relative to the stem body axis 312. Also as shown in FIG. 35 and FIG. 37 for the third embodiment 3003 and the fourth embodiment 3004, respectively, in some embodiments the first grasper jaw 316 is curved from the proximal end 318 of the first grasper jaw 316 to the distal end 324 of the first grasper jaw 316 relative to the stem body axis 312. The second grasper jaw 330 also can be straight or curved. Preferably, both the first and second grasper jaws 316, 330 are straight or both are curved.

As shown in FIG. 30, FIG. 33, FIG. 35, FIG. 37, FIG. 39, and FIG. 41 for the first to sixth embodiments 3001-3006, respectively, the magnet-assisted suture grasper 300 also comprises a grasper magnet 340 being disposed adjacent the proximal-to-intermediate portion 320 of the first grasper jaw 316. With reference to FIG. 32 for the first embodiment 3001, the magnet-assisted suture grasper 100 sequesters the grasper magnet 340 between the first and second grasper jaws 316, 330 in a recess 342 formed in at least one of the first or second grasper jaws 316, 330 when the first grasper jaw 316 is in the first position 326 and exposing the grasper magnet 340 from the recess 342 when the first grasper jaw 316 is in the second position 328. The grasper magnet 340 can be, for example, a permanent dipole magnet.

As shown in FIG. 30, FIG. 33, FIG. 35, FIG. 37, FIG. 39, and FIG. 41 for the first to sixth embodiments 3001-3006, respectively, in some embodiments the grasper magnet 340 is fixedly attached to the proximal-to-intermediate portion 320 of the first grasper jaw 316. Alternatively, in some embodiments the grasper magnet 340 is fixedly attached to the proximal-to-intermediate portion 334 of the second grasper jaw 330. Also, in some embodiments the grasper magnet 340 is fixedly attached to the stem 304 between the proximal-to-intermediate portions 320, 334 of the first and second grasper jaws 316, 330.

Figure 29:
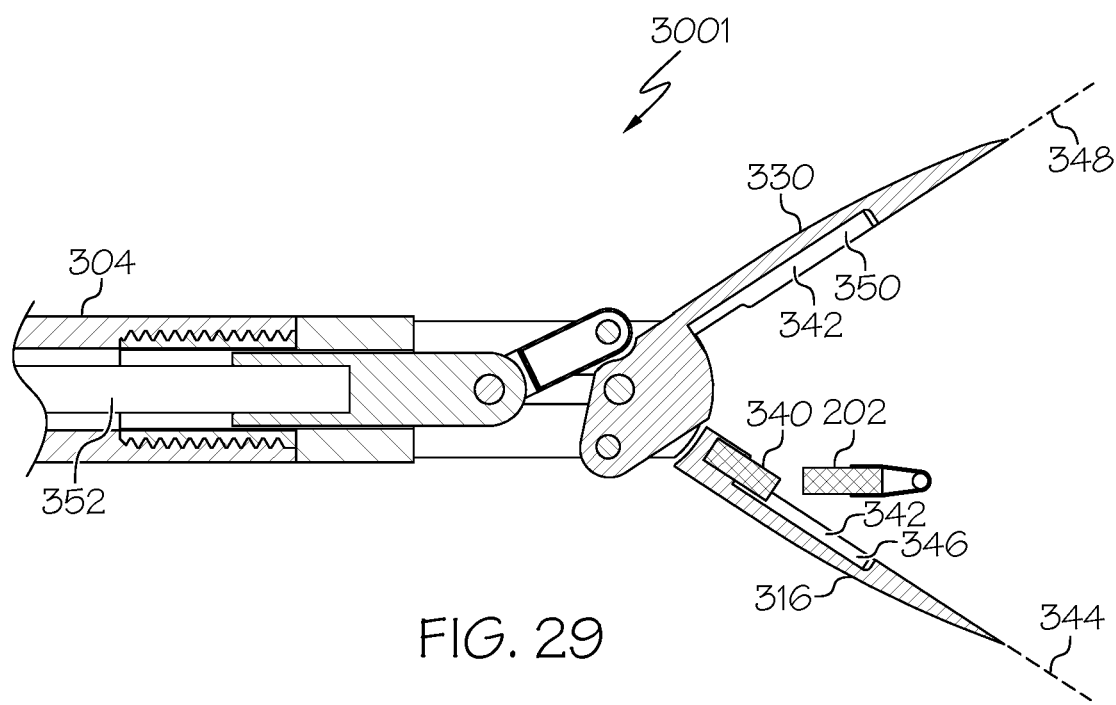
FIG. 29 is a sectional view of the distal end of the magnet-assisted suture grasper of FIG. 25, in which the first grasper jaw is in the second position, the second grasper jaw has pivoted away from the first grasper jaw, and the grasper magnet is attracting a suture magnet of a magnetic suture (the suture of the magnetic suture is not shown).

As noted above and as shown in FIG. 32 for the first embodiment 3001, the magnet-assisted suture grasper 300 sequesters the grasper magnet 340 between the first and second grasper jaws 316, 330 in a recess 342 formed in at least one of the first or second grasper jaws 316, 330 when the first grasper jaw 316 is in the first position 326. As shown in FIG. 29 for the first embodiment 3001, in some embodiments the first grasper jaw 316 defines a first grasper jaw axis 344 and the proximal-to-intermediate portion 320 of the first grasper jaw 316 comprises a recessed portion 346 along the first grasper jaw axis 344 that defines at least part of the recess 342. Also as shown, in some embodiments the second grasper jaw 330 defines a second grasper jaw axis 348 and the proximal-to-intermediate portion 334 of the second grasper jaw 330 comprises a recessed portion 350 along the second grasper jaw axis 348 that defines at least part of the recess 342. Also as shown, in some embodiments the first grasper jaw 316 defines a first grasper jaw axis 344, the second grasper jaw 330 defines a second grasper jaw axis 348, and the proximal-to-intermediate portions 320, 334 of the first and second grasper jaws 316, 330 comprise recessed portions 346, 350 along the first grasper jaw axis 344 and the second grasper jaw axis 348, respectively, that define the recess 342.

Also as shown in FIG. 29 for the first embodiment 3001, in some embodiments the grasper magnet 340 is a permanent dipole magnet. Also as shown in FIG. 29, in some examples of these embodiments the grasper magnet 340 is fixedly attached to the proximal-to-intermediate portion 320 of the first grasper jaw 316 such that the poles of grasper magnet 340 are positioned along the first grasper jaw axis 344. In other examples of these embodiments the grasper magnet 340 is fixedly attached to the proximal-to-intermediate portion 334 of the second grasper jaw 330 such that the poles of grasper magnet 340 are positioned along the second grasper jaw axis 348. In still other examples of these embodiments the grasper magnet 340 is fixedly attached to the stem 304 at the distal end 308 such that the poles of grasper magnet 340 are positioned along the stem body axis 312.

Figure 28:
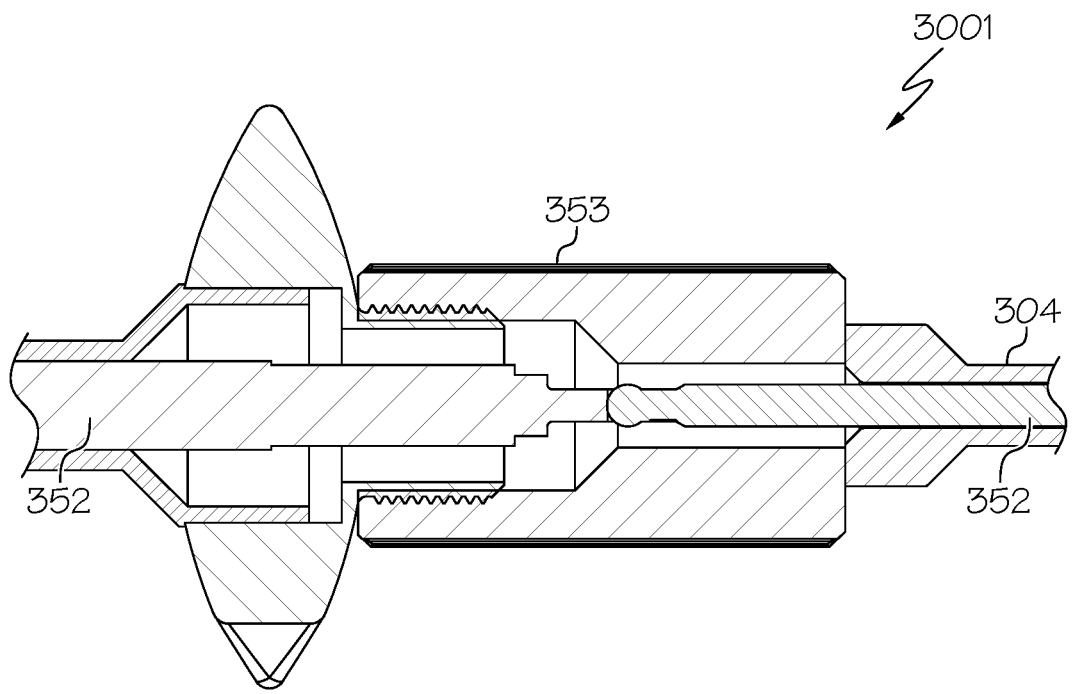
FIG. 28 is a sectional view of a proximal rotation collar of the magnet-assisted suture grasper of FIG. 25.

As shown in FIGS. 27-29 for the first embodiment 3001, the magnet-assisted suture grasper 300 also comprises an actuator body 352 disposed within the stem lumen 314 and translatable therein along the stem body axis 312. The actuator body 352 is connected to the handle 302 and the first grasper jaw 316 and is configured for pivotal actuation of the first grasper jaw 316 by movement of the handle 302. The actuator body 352 can be configured, for example, so that in a resting state the first grasper jaw 316 is in the second position 328. In accordance with this example, when an operator squeezes the handle 302, the squeezing of the handle 302 causes the actuator body 352 to translate proximally, thereby pivotally actuating the first grasper jaw 316 to move from the second position 328 to the first position 326. Also in accordance with this example, when the operator releases the handle 302, the releasing of the handle 302 causes the actuator body 352 to translate distally, thereby pivotally actuating the first grasper jaw 316 to move from the first position 326 to the second position 328. This is a typical configuration for actuating grasper jaws of suture passers with articulating grasper jaws. Other configurations can be suitable too. The actuator body 352 can be made of metal, such as stainless steel or titanium, or plastic or other suitable material for accomplishing actuation of the first grasper jaw 316.

As shown in FIG. 28, in some embodiments the actuator body 352 comprises multiple elongated parts. This can be advantageous, for example, for a magnet-assisted suture grasper 300 that comprises a rotating collar 353 that allows rotation of first and second grasper jaws 316, 330 without requiring rotation of the handle 302.

As shown in FIG. 30, FIG. 33, FIG. 35, FIG. 37, FIG. 39, and FIG. 41 for the first to sixth embodiments 3001-3006, respectively, the distal ends 324, 338 of the first and second grasper jaws 316, 330 extend further distally than the grasper magnet 340. This means that the distal ends 324, 338 of the first and second grasper jaws 316, 330 extend further distally from the stem 304 than does any portion of the grasper magnet 340. Thus, the grasper magnet 340 is closer to the distal end 308 of the stem 304 than are the distal ends 324, 338 of the first and second grasper jaws 316, 330.

Figure 30:
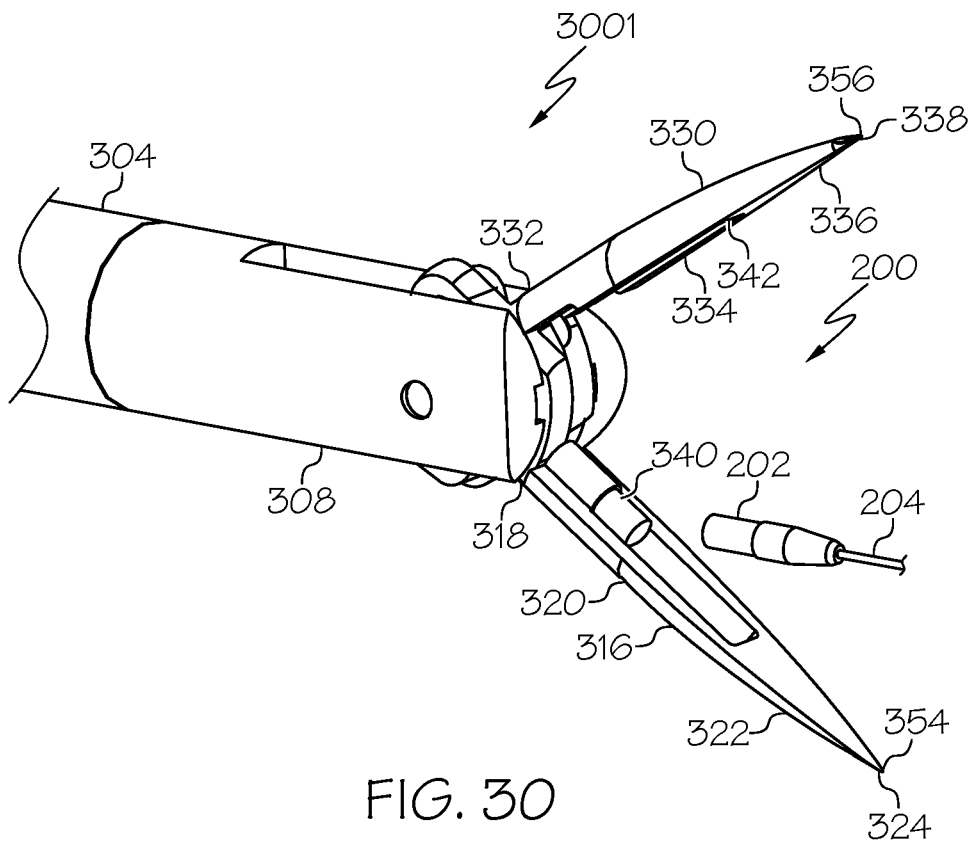
FIG. 30 is a perspective view of the distal end of the magnet-assisted suture grasper of FIG. 25, in which the first grasper jaw is in the second position, the second grasper jaw has pivoted away from the first grasper jaw, and the grasper magnet is attracting a magnetic suture.

As shown by comparison of FIG. 31 with FIG. 30 for the first embodiment 3001, comparison of FIG. 34 with FIG. 33 for the second embodiment 3002, comparison of FIG. 36 with FIG. 35 for the third embodiment 3003, comparison of FIG. 38 with FIG. 37 for the fourth embodiment 3004, comparison of FIG. 40 with FIG. 39 for the fifth embodiment 3002, and comparison of FIG. 42 with FIG. 41 for the sixth embodiment 3006, translation of the actuator body 352 within the stem lumen 314 in a first direction along the stem body axis 312 causes the first grasper jaw 316 to pivot from the first position 326 to the second position 328, thereby exposing the grasper magnet 340 and allowing contact between the grasper magnet 340 and a magnetic suture 300 attracted thereto. The translation of the actuator body 352 results in pivoting of the first grasper jaw 316. The translation of the actuator body 352 in the first direction can be translation of the actuator body 352 within the stem lumen 314 in a direction from the proximal end 306 of the stem 304 toward the distal end 308 of the stem 304. When the first grasper jaw 316 is in the first position 326 the grasper magnet 340 can be disposed entirely inside the recess 342, and thus sequestered within the first and second grasper jaws 316, 330. In accordance with these embodiments, such translation of the actuator body 352 within the stem lumen 314 in the first direction can pivotally move the first grasper jaw 316 away from the second grasper jaw 330, thus exposing the grasper magnet 340.

As shown by comparison of FIG. 30 with FIG. 31 for the first embodiment 3001, comparison of FIG. 33 with FIG. 34 for the second embodiment 3002, comparison of FIG. 35 with FIG. 36 for the third embodiment 3003, comparison of FIG. 37 with FIG. 38 for the fourth embodiment 3004, comparison of FIG. 39 with FIG. 40 for the fifth embodiment 3002, and comparison of FIG. 41 with FIG. 42 for the sixth embodiment 3006, translation of the actuator body 352 within the stem lumen 314 in a second direction opposite the first direction along the stem body axis 312 causes the first grasper jaw 316 to pivot from the second position 328 to the first position 326, thereby sequestering the grasper magnet 340 and grasping the magnetic suture 200 within the recess 342. The translation of the actuator body 352 in the second direction can be translation of the actuator body 352 within the stem 304 in a direction from the distal end 108 of the stem 304 toward the proximal end 106 of the stem 304. Such translation of the actuator body 352 within the stem lumen 314 in the second direction can pivotally move the first grasper jaw 316 toward the second grasper jaw 330, thus sequestering the grasper magnet 340 again and grasping the magnetic suture 200 within the first and second grasper jaws 316, 330.

This can be accomplished as follows. Because the grasper magnet 340 is closer to the distal end 308 of the stem 304 than are the distal ends 324, 338 of the first and second grasper jaws 316, 330, when a suture magnet 202 of a magnetic suture 200 contacts the grasper magnet 340 and the actuator body 352 is translated in the second direction to the first position 326, the grasper magnet 340 and the suture magnet 202 of the magnetic suture 200 fit within the recess 342 before the first grasper jaw 316 closes on the second grasper jaw 330, and thus the suture magnet 202 of the magnetic suture 200 is grasped by the first and second grasper jaws 316, 330 as the magnet-assisted suture grasper 100 is used to pull the magnetic suture 200 through soft tissue of a patient. The first and second grasper jaws 316, 330 are sufficiently strong to resist the frictional drag that results from pulling the magnetic suture 200 through the soft tissue.

As noted above, the first grasper jaw 316 comprises a proximal end 318, a proximal-to-intermediate portion 320, a distal portion 322, and a distal end 324. Also as noted, the grasper magnet 340 is disposed adjacent the proximal-to-intermediate portion 320 of the first grasper jaw 316. The recess 342 formed in at least one of the first or second grasper jaws 316, 330 when the first grasper jaw 316 is in the first position 326 has a length and orientation sufficient to allow the suture magnet 202 of a magnetic suture 200 to fit between the grasper magnet 340 and the distal end 324 of the first grasper jaw 316 when the first grasper jaw 316 is in the second position 328, so that the suture magnet 202 of the magnetic suture 200 can contact the grasper magnet 340 for magnetic attraction, and when the first grasper jaw 316 has been returned to the first position 326, so that the suture magnet 202 of the magnetic suture 200 can fit within the recess 342 along with the grasper magnet 340. The proximal-to-intermediate portion 320 of the first grasper jaw 316 adjacent to which the grasper magnet 340 is disposed can be any portion of the first grasper jaw 316 distal to the proximal end 318 and proximal to the distal portion 322, so long as sufficient space is provided for a suture magnet 202 to fit between the grasper magnet 340 and the distal end 324 of the first grasper jaw 316 within the recess 342.

As noted above and as shown in FIG. 30, FIG. 35, and FIG. 39 for the first embodiment 3001, the third embodiment 3003, and the fifth embodiment 3005, respectively, in some embodiments, the second grasper jaw 330 is reversibly moveable. In these embodiments the actuator body 352 is further connected to the second grasper jaw 330 and configured for pivotal actuation of the second grasper jaw 330 by movement of the handle 302. For example, the actuator body 352 can be configured with respect to the second grasper jaw 330 as described above for the first grasper jaw 316. Other configurations can be suitable too. In these embodiments, translation of the actuator body 352 within the stem lumen 314 in the first direction causes the second grasper jaw 330 to pivot away from the first grasper jaw 316, thereby further exposing the grasper magnet 340 and allowing contact between the grasper magnet 340 and a magnetic suture 200 attracted thereto. Also in these embodiments translation of the actuator body 352 within the stem lumen 314 in the second direction causes the second grasper jaw 330 to pivot toward the first grasper jaw 316, thereby contributing to sequestering the grasper magnet 340 and grasping the magnetic suture 200 within the recess 342. These embodiments can be advantageous by providing a greater range of motion for the first and second grasper jaws 316, 330 during operation of the magnet-assisted suture grasper 300, and thus more space for a suture magnet 202 of a magnetic suture 200 to contact the grasper magnet 340 when the first grasper jaw 316 is in the second position 328.

As shown in FIG. 30, in some embodiments, the distal ends 308, 338 of the first and second grasper jaws 316, 330 have sharp tips 354, 356. This can be advantageous for piercing tissue during insertion of the magnet-assisted suture grasper 300 into a patient.

The embodiment 3001 of the magnet-assisted suture grasper 300 can be operated as follows.

After a magnetic suture 200 has been deposited inside a patient, the handle 302 of the magnet-assisted suture grasper 300 is moved, e.g., squeezed, to pivotally actuate the first and second grasper jaws 316, 330 via the actuator body 352, such that such that the first grasper jaw 316 pivots from the second position 328 to the first position 326, and the second grasper jaw 330 pivots toward from the first grasper jaw 316, to close the first grasper jaw 316 on the second grasper jaw 330. The distal end of the magnet-assisted suture grasper 300, including the first and second grasper jaws 316, 330 and the distal end 308 of the stem 304, is introduced into the patient to gain access to the site of the suture.

The handle is then moved, e.g., released, to pivotally actuate the first and second grasper jaws 316, 330, such that the first grasper jaw 316 pivots from the first position 326 to the second position 328, and the second grasper jaw 330 pivots away from the first grasper jaw 316, thereby exposing the grasper magnet 340 from the recess 342 formed between the first and second grasper jaws 316, 330. The first and second grasper jaws 316, 330 and the grasper magnet 340 are brought near the suture magnet 202 of the magnetic suture 200, so that the magnetic fields of the grasper magnet 340 and the suture magnet 202 can interact. The attractive force between the grasper magnet 340 and the suture magnet 202 pulls the suture magnet 202 towards the grasper magnet 340 and brings them into contact and axial alignment.

Then the handle 302 is again moved, e.g., squeezed, to pivotally to return the first grasper jaw 316 from the second position 328 to the first position 326, and to pivot the second grasper jaw 330 toward the first grasper jaw 316. As the first and second grasper jaws 316, 330 pivot toward each other, the grasper magnet 340 and the suture magnet 202 of the magnetic suture 200 fit within the recess 342 before the first grasper jaw 316 closes completely on the second grasper jaw 330. At this point, the magnetic suture 200 cannot escape the recess 342 formed between the first and second grasper jaws 316, 330.

Once the magnetic suture 200 has been captured, the magnet-assisted suture grasper 300 can be used to pull or push the magnetic suture 200 to a new location. The first and second grasper jaws 316, 330 allow the magnet-assisted suture grasper 300 to hold the magnetic suture 200 securely, even when the magnetic suture 200 is heavily loaded to the point that the load exceeds the attractive force between grasper magnet 340 and the suture magnet 202.

Once the magnetic suture 200 has been passed to the desired location, the magnetic suture 200 can be released from the magnet-assisted suture grasper 300. To release the magnetic suture 200, the handle 302 is again moved, e.g., released, to pivotally actuate the first and second grasper jaws 316, 330, thereby exposing the grasper magnet 340 and the suture magnet 202 of the magnetic suture 200 from the recess 342. The suture 204 can then be pulled to disconnect the grasper magnet 340 and the suture magnet 202.

With reference to FIGS. 43-47, a magnetic suture loop 400 also is disclosed. The magnetic suture loop 400 comprises a suture magnet 402 and a bifurcated suture 404 extending from the suture magnet 402 and forming a suture loop 406.

The magnetic suture loop 400 can be made similarly as described in U.S. Pub. No. 2021/0059667, as discussed above. Thus, in some embodiments the magnetic suture loop 400 further comprises a ferrule 408 with a tapered region 410 in which the bifurcated suture 404 is provided knotted and secured with an adhesive and a straight region 412 in which the suture magnet 402 is provided.

The magnetic suture loop 400 is advantageous for providing a means of snaring a second suture, for the purpose of pulling the second suture through the suture loop 406 created by the first suture. A surgeon can accomplish this as follows. The magnetic suture loop 400 is first passed through a tissue of a patient, so that the magnetic suture loop 400 has an entrance point and an exit point from the patient. The entrance point and exit points can be separate points or the same point. A strand of a second suture is then passed through the suture loop 406 of the magnetic suture loop 400. The magnetic suture loop 400 is then pulled through the tissue from the opposite end. As the magnetic suture loop 400 is pulled through the entrance point of the tissue, the suture loop 406 is closed around the second suture by the tissue, effectively snaring the second suture. This snaring action allows the magnetic suture loop to pull the second suture through the tissue and out the exit point, so that the second suture now occupies the path that was previously occupied by the magnetic suture loop 400. This is advantageous because it allows limiting permutations of suture size, material, and construction, without restricting choice as to the type of suture that will be used. For example, if a surgeon wishes to use a different style of suture than the magnetic suture loop 400, the surgeon can use the magnetic suture loop 400 to establish the path, and then use the technique described above to quickly and easily exchange the magnetic suture loop 400 for a different second suture.

With reference to FIGS. 48-52, a preloaded magnetic suture cartridge 500 also is disclosed. The preloaded magnetic suture cartridge 500 comprises a magnetic suture loop 400 and a cartridge tube 502. The magnetic suture loop 400 can be as described above. The cartridge tube 502 comprises a cartridge tube proximal opening 504, a cartridge tube distal opening 506, and a cartridge tube lumen 508 therebetween.

The magnetic suture loop 400 can be preloaded into the cartridge tube 502 during manufacture, such that the suture loop 406 of the magnetic suture loop 400 traverses the cartridge tube lumen 508, which is sized such that the suture loop 406 is free to enter the cartridge tube lumen 508 but the suture magnet 402 of the suture loop 406 does not enter the cartridge tube lumen 508, so that the suture loop 406 can freely pass through the cartridge tube lumen 508 in one direction but is captured in the opposite direction. The wall thickness of the cartridge tube 502 and the modulus of the material used in its construction are such that the cartridge tube 502 has greater column strength than the suture loop 406, allowing the preloaded magnetic suture cartridge 500, including the magnetic suture loop 400, to be easily inserted into and advanced through a cannula by pushing from one end.

This is advantageous because the suture loop 406 itself does not have sufficient column strength to allow the suture loop 406 to be pushed through a cannula from one end. The cartridge tube 502 therefore facilitates advancing the suture loop 406 through a cannula and into the intracorporeal working space. The cannula and the cartridge tube 502 can then be removed, leaving only the suture loop 406 behind. Alternatively, the cannula can be removed and the cartridge tube 502 with captured suture loop 406 can be left behind. Leaving the cartridge tube 502 in this manner may provide some benefit during the procedure because the stiffness of the cartridge tube 502 provides the operator with a means for directionally manipulating the suture magnet 402 of the magnetic suture loop 400 at the distal end of the suture loop 406 from outside the body. To this effect, a curve can be added to the distal end of the cartridge tube 502, which further enhances the operator's ability to directionally manipulate the suture magnet 402 of the magnetic suture loop 400 within the intracorporeal space.

A system for passing a magnetic suture also is disclosed. The system comprises the magnet-assisted suture grasper comprising (a) a suture retrieval needle, (b) a retriever body, (c) a grasper arm, and (d) a grasper magnet as described above. The system also comprises a magnetic suture comprising a suture magnet and a suture extending from the suture magnet as described above.

Another system for passing a magnetic suture also is disclosed. The system comprises the magnet-assisted suture grasper comprising (a) a handle, (b) a stem, (c) a first grasper jaw, (d) a second grasper jaw, (e) a grasper magnet, and (f) an actuator body as described above. The system also comprises a magnetic suture comprising a suture magnet and a suture extending from the suture magnet as described above.

Another system for passing a magnetic suture also is disclosed. The system comprises the magnet-assisted suture grasper comprising (a) a suture retrieval needle, (b) a retriever body, (c) a grasper arm, and (d) a grasper magnet as described above. The system also comprises a magnetic suture loop comprising a suture magnet and a bifurcated suture extending from the suture magnet and forming a suture loop as described above. In some embodiments, this system further comprises a cartridge tube as described above. The cartridge tube comprises a cartridge tube proximal opening, a cartridge tube distal opening, and a cartridge tube lumen therebetween. The suture loop traverses the cartridge tube lumen based on having been inserted through the cartridge tube distal opening. The suture magnet is disposed outside of the cartridge tube lumen adjacent the cartridge tube distal opening.

Another system for passing a magnetic suture also is disclosed. The system comprises the magnet-assisted suture grasper comprising (a) a handle, (b) a stem, (c) a first grasper jaw, (d) a second grasper jaw, (e) a grasper magnet, and (f) an actuator body as described above. The system also comprises a magnetic suture loop comprising a suture magnet and a bifurcated suture extending from the suture magnet and forming a suture loop as described above. In some embodiments, this system further comprises a cartridge tube as described above. The cartridge tube comprises a cartridge tube proximal opening, a cartridge tube distal opening, and a cartridge tube lumen therebetween. The suture loop traverses the cartridge tube lumen based on having been inserted through the cartridge tube distal opening. The suture magnet is disposed outside of the cartridge tube lumen adjacent the cartridge tube distal opening.

The magnet-assisted suture graspers disclosed herein can be used for passing a magnetic suture that includes a suture magnet at an end of the suture. Such a magnetic suture can be made, for example, as described in U.S. Pub. No. 2021/0059667. The magnet-assisted suture graspers disclosed herein also can be used for passing a magnetic suture that is magnetic based on including a magnetic metal within the suture.

The magnet-assisted suture graspers disclosed herein may be useful in procedures including, among others: (1) Inguinal hernia repair through high ligation of the patent processus vaginalis as described above; (2) Laparoscopic port closure (typical suture size 2-0 and larger); (3) Microsurgery (typical suture size 7-0 and smaller); (4) General surgery (typical suture size 2-0 to 0); and (5) Orthopedic surgery (typical suture size 0 and larger).

The magnet-assisted suture graspers also may be modified for use in ultrasound-guided surgical techniques. The magnet-assisted suture graspers would be modified by making the distal end of the suture retrieval needle echogenic. This could be done, for example, by applying an echogenic treatment at the distal tip of the suture retrieval needle or to the grasper jaws. The modified magnet-assisted suture graspers would then be used with a hypodermic needle for introducing a suture wherein the hypodermic needle also is echogenic at its distal end. Optionally the magnets of the magnet-assisted suture graspers and the magnetic suture and/or the ferrules that attach the magnets to wires of the magnet-assisted suture graspers and to the suture also may be made echogenic, for example by applying an echogenic treatment to the magnets and/or the ferrules.

Use of the modified magnet-assisted suture graspers in ultrasound-guided surgical techniques could result in reductions in operative time and complexity by eliminating the need for suction equipment. Suction equipment currently is needed to pass the suture through the needle.

The modified magnet-assisted suture graspers also may allow an alternative technique whereby the suture is dropped off and retrieved from inside the abdominal cavity. This would allow the repair to be completed entirely through a single needle-access point, which would provide improved cosmesis, and could result in less post-operative pain. Under the current laparoscopic approach (termed the PEAR/PIRS technique), the needle is introduced through the skin and directed medial around the defect, exiting inferior to the defect through the peritoneum into the abdominal cavity. Drop-off and retrieval of the suture occurs in this space inside the abdominal cavity. This is not currently possible under ultrasonic guidance because the suture is not echogenic, so the surgeon would have to retrieve the suture from inside the abdominal cavity completely blind. This would be nearly impossible with the current state of suture passer technology (i.e., snares, graspers, etc.). In contrast, the modified magnet-assisted suture graspers may allow this to work, especially if the needle points and ferrules are echogenic.

The mechanical grasper arm technology described herein could be integrated into the magnetic U-stitch suturing device disclosed in U.S. Pat. No. 10,245,021 to provide a more secure means of holding a magnetic suture during retrieval. In addition, this could allow the operation of the device to be changed such that the suture does not need to be pulled completely out of the body through the second cannula, but could simply be captured, and then the whole device removed, pulling the suture through the tissue directly. This should allow the magnetic U-stitch suturing device to be used to place multiple sutures with a single device.

In addition, the magnet-assisted suture graspers described herein could be integrated as end-of-arm tooling for robot-assisted surgery or into the end of an endoscope for direct manipulation of a suture with the endoscope.

Although the magnet-assisted suture graspers are described for grasping a magnetic suture, the magnet-assisted suture graspers also can be used for grasping sutures that include ferromagnetic elements that are attracted by magnets without necessarily including a suture magnet.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention.

CLAUSES

1. A magnet-assisted suture grasper for grasping a magnetic suture comprising:
   (a) a suture retrieval needle comprising a proximal end, a distal end, and a needle body extending therebetween, the needle body defining a needle body axis between the proximal and distal ends of the suture retrieval needle, the needle body having a proximal hole, a distal hole, and a needle lumen extending therebetween along the needle body axis;
   (b) a retriever body disposed within the needle lumen and translatable therein along the needle body axis;
   (c) a grasper arm comprising a proximal end, a proximal-to-intermediate portion, a distal portion, and a distal end, the grasper arm extending from the distal end of the retriever body and being reversibly moveable between a first position and a second position; and
   (d) a grasper magnet being disposed adjacent the proximal-to-intermediate portion of the grasper arm, the magnet-assisted suture grasper sequestering the grasper magnet within the needle lumen when the grasper arm is in the first position and exposing the grasper magnet from the needle lumen when the grasper arm is in the second position, wherein:
   the distal end of the grasper arm extends further distally than the grasper magnet,
   translation of the retriever body within the needle lumen in a first direction along the needle body axis causes the grasper arm to move from the first position to the second position, thereby exposing the grasper magnet and allowing contact between the grasper magnet and a magnetic suture attracted thereto, and
   translation of the retriever body within the needle lumen in a second direction opposite the first direction along the needle body axis causes the grasper arm to move from the second position to the first position, thereby sequestering the grasper magnet and grasping the magnetic suture within the needle lumen.

2. The magnet-assisted suture grasper according to clause 1, wherein the suture retrieval needle is straight, the needle body axis thereby being straight.

3. The magnet-assisted suture grasper according to clause 1, wherein the suture retrieval needle is curved, the needle body axis thereby being curved.

4. The magnet-assisted suture grasper according to any one of clauses 1-3, wherein the suture retrieval needle has a sharp tip.

5. The magnet-assisted suture grasper according to any one of clauses 1-4, wherein the grasper arm is integral to the retriever body.

6. The magnet-assisted suture grasper according to any one of clauses 1-5, wherein the grasper magnet is fixedly attached to the distal end of the retriever body, either directly or indirectly.

7. The magnet-assisted suture grasper according to any one of clauses 1-6, wherein the grasper magnet is fixedly attached to the grasper arm, either directly or indirectly, at the proximal-to-intermediate portion of the grasper arm.

8. The magnet-assisted suture grasper according to any one of clauses 1-6, further comprising a magnet wire having a proximal end and a distal end, wherein the proximal end of the magnet wire is fixedly disposed within the retriever body and the grasper magnet is fixedly attached to the distal end of the magnet wire, either directly or indirectly.

9. The magnet-assisted suture grasper according to any one of clauses 1-8, wherein:

the grasper arm further comprises an enlarged distal terminus at the distal end of the grasper arm;

the grasper arm is reversibly moveable between the first position and the second position based on translation of the grasper arm from inside of the needle lumen to outside of the needle lumen through the distal hole of the needle body; and the enlarged distal terminus at the distal end of the grasper arm has a size sufficiently small to allow contact between the grasper magnet and a suture magnet of a magnetic suture attracted thereto when the grasper arm is in the second position and to allow a suture of the magnetic suture to pass when the grasper arm is in the first position, and sufficiently large to block the suture magnet of the magnetic suture from exiting the needle lumen through the distal hole of the needle body when the grasper arm is in the first position.

10. The magnet-assisted suture grasper according to clause 9, wherein the enlarged distal terminus comprises a hook.

11. The magnet-assisted suture grasper according to any one of clauses 1-8, wherein:

the grasper arm is a first grasper arm;

the magnet-assisted suture grasper further comprises a second grasper arm comprising a proximal end, a proximal-to-intermediate portion, a distal portion, and a distal end, the second grasper arm extending from the distal end of the retriever body and being reversibly moveable between the first position and the second position;

the first grasper arm further comprises an enlarged distal terminus at the distal end of the first grasper arm;

the second grasper arm further comprises an enlarged distal terminus at the distal end of the second grasper arm;

the first and second grasper arms are reversibly moveable between the first position and the second position based on translation of the first and second grasper arms from inside of the needle lumen to outside of the needle lumen through the distal hole of the needle body; and the enlarged distal termini of the first and second grasper arms have sizes sufficiently small to allow contact between the grasper magnet and a suture magnet of a magnetic suture attracted thereto when the first and second grasper arms are in the second position and to allow a suture of a magnetic suture to pass when the first and second grasper arms are in the first position, and sufficiently large to block the suture magnet of the magnetic suture from exiting the needle lumen through the distal hole of the needle body when the first and second grasper arms are in the first position.

12. The magnet-assisted suture grasper according to clause 11, further comprising at least one additional grasper arm extending distally from the retriever body.

13. The magnet-assisted suture grasper according to any one of clauses 1-8, wherein:

the grasper arm is a first grasper arm;

the magnet-assisted suture grasper further comprises a second grasper arm comprising a proximal end, a proximal-to-intermediate portion, a distal portion, and a distal end, the second grasper arm extending from the distal end of the retriever body and being reversibly moveable between the first position and the second position;

the first and second grasper arms are connected at their distal ends, thereby forming a grasper arm loop;

the grasper arm loop is reversibly moveable between the first position and the second position based on translation of the grasper arm loop from inside of the needle lumen to outside of the needle lumen through the distal hole of the needle body;

the grasper arm loop circumscribes an area sufficiently large to allow contact between the grasper magnet and a suture of a magnetic suture attracted thereto when the grasper arm loop is in the second position; and the grasper arm loop has a thickness sufficiently great to block the suture magnet of the magnetic suture from exiting the needle lumen through the distal hole of the needle body when the grasper arm loop is in the first position.

14. The magnet-assisted suture grasper according to any one of clauses 1-8, wherein:

the grasper arm is a first grasper arm;

the magnet-assisted suture grasper further comprises a second grasper arm comprising a proximal end, a proximal-to-intermediate portion, a distal portion, and a distal end, the second grasper arm extending from the distal end of the retriever body and being reversibly moveable between the first position and the second position;

the first and second grasper arms are connected at their distal ends, thereby forming a grasper arm loop;

the first and second grasper arms further comprise an enlarged distal terminus at the distal ends of the first and second grasper arms;

the grasper arm loop is reversibly moveable between the first position and the second position based on translation of the grasper arm loop from inside of the needle lumen to outside of the needle lumen through the distal hole of the needle body;

the grasper arm loop circumscribes an area sufficiently large, and the enlarged distal terminus at the distal ends of the first and second grasper arms has a size sufficiently small, to allow contact between the grasper magnet and a suture magnet of a magnetic suture attracted thereto when the grasper arm loop is in the second position;

the enlarged distal terminus at the distal ends of the first and second grasper arms has a size sufficiently small to allow a suture of the magnetic suture to pass when the grasper arm loop is in the first position; and the enlarged distal terminus at the distal ends of the first and second grasper arms has a size sufficiently large to block the suture magnet of the magnetic suture from exiting the needle lumen through the distal hole of the needle body when the grasper arm loop is in the first position.

15. The magnet-assisted suture grasper according to any one of clauses 1-8, wherein:

the grasper arm is a first grasper arm;

the magnet-assisted suture grasper further comprises a second grasper arm comprising a proximal end, a proximal-to-intermediate portion, a distal portion, and a distal end, the second grasper arm extending from the distal end of the retriever body and being reversibly moveable between the first position and the second position;

the first grasper arm further comprises an enlarged distal terminus at the distal end of the first grasper arm;

the second grasper arm further comprises an enlarged distal terminus at the distal end of the second grasper arm;

the first and second grasper arms are reversibly moveable between the first position and the second position based on translation of the first and second grasper arms from inside of the needle lumen to outside of the needle lumen through the distal hole of the needle body;

the proximal-to-intermediate portions of the first and second grasper arms are substantially parallel to the needle body axis when the first and second grasper arms are in the first position;

at least one of the first or second grasper arms pivots reversibly outwardly from the needle body axis sufficiently far to allow contact between the grasper magnet and a suture magnet of a magnetic suture attracted thereto when the first and second grasper arms are in the second position; and the enlarged distal termini of the first and second grasper arms have sizes sufficiently small to allow a suture of the magnetic suture to pass when the first and second grasper arms are in the first position, and sufficiently large to block the suture magnet of the magnetic suture from exiting the needle lumen through the distal hole of the needle body when the first and second grasper arms are in the first position.

16. A system for passing a magnetic suture comprising:
the magnet-assisted suture grasper of any one of clauses 1-15; and
a magnetic suture comprising a suture magnet and a suture extending from the suture magnet.

17. A system for passing a magnetic suture comprising:
the magnet-assisted suture grasper of any one of clauses 1-15; and
a magnetic suture loop comprising a suture magnet and a bifurcated suture extending from the suture magnet and forming a suture loop.

18. The system according to clause 17, further comprising a cartridge tube, wherein:
the cartridge tube comprises a cartridge tube proximal opening, a cartridge tube distal opening, and a cartridge tube lumen therebetween;
the suture loop traverses the cartridge tube lumen based on having been inserted through the cartridge tube distal opening; and
the suture magnet is disposed outside of the cartridge tube lumen adjacent the cartridge tube distal opening.

19. A magnet-assisted suture grasper for grasping a magnetic suture comprising:
(a) a handle;
(b) a stem comprising a proximal end, a distal end, and a stem body extending therebetween, the stem being connected to the handle adjacent the proximal end of the stem, the stem body defining a stem body axis and including a stem lumen extending along the stem;
(c) a first grasper jaw comprising a proximal end, a proximal-to-intermediate portion, a distal portion, and a distal end, the first grasper jaw extending from the stem adjacent the distal end of the stem and being reversibly moveable between a first position and a second position;
(d) a second grasper jaw comprising a proximal end, a proximal-to-intermediate portion, a distal portion, and a distal end, the second grasper jaw extending from the stem adjacent the distal end of the stem;
(e) a grasper magnet being disposed adjacent the proximal-to-intermediate portion of the first grasper jaw, the magnet-assisted suture grasper sequestering the grasper magnet between the first and second grasper jaws in a recess formed in at least one of the first or second grasper jaws when the first grasper jaw is in the first position and exposing the grasper magnet from the recess when the first grasper jaw is in the second position; and
(f) an actuator body disposed within the stem lumen and translatable therein along the stem body axis, the actuator body connected to the handle and the first grasper jaw and configured for pivotal actuation of the first grasper jaw by movement of the handle;
wherein:
the distal ends of the first and second grasper jaws extend further distally than the grasper magnet, translation of the actuator body within the stem lumen in a first direction along the stem body axis causes the first grasper jaw to pivot from the first position to the second position, thereby exposing the grasper magnet and allowing contact between the grasper magnet and a magnetic suture attracted thereto, and translation of the actuator body within the stem lumen in a second direction opposite the first direction along the stem body axis causes the first grasper jaw to pivot from the second position to the first position, thereby sequestering the grasper magnet and grasping the magnetic suture within the recess.

20. The magnet-assisted suture grasper according to clause 19, wherein the first grasper jaw is straight from the proximal end of the first grasper jaw to the distal end of the first grasper jaw relative to the stem body axis.

21. The magnet-assisted suture grasper according to clause 19, wherein the first grasper jaw is curved from the proximal end of the first grasper jaw to the distal end of the first grasper jaw relative to the stem body axis.

22. The magnet-assisted suture grasper according to any one of clauses 19-21, wherein the first grasper jaw defines a first grasper jaw axis and the proximal-to-intermediate portion of the first grasper jaw comprises a recessed portion along the first grasper jaw axis that defines at least part of the recess.

23. The magnet-assisted suture grasper according to any one of clauses 19-21, wherein the second grasper jaw defines a second grasper jaw axis and the proximal-to-intermediate portion of the second grasper jaw comprises a recessed portion along the second grasper jaw axis that defines at least part of the recess.

24. The magnet-assisted suture grasper according to any one of clauses 19-21, wherein the first grasper jaw defines a first grasper jaw axis, the second grasper jaw defines a second grasper jaw axis, and the proximal-to-intermediate portions of the first and second grasper jaws comprise recessed portions along the first grasper jaw axis and the second grasper jaw axis, respectively, that define the recess.

25. The magnet-assisted suture grasper according to any one of clauses 19-24, wherein the grasper magnet is fixedly attached to the proximal-to-intermediate portion of the first grasper jaw.

26. The magnet-assisted suture grasper according to any one of clauses 19-24, wherein the grasper magnet is fixedly attached to the proximal-to-intermediate portion of the second grasper jaw.

27. The magnet-assisted suture grasper according to any one of clauses 19-24, wherein the grasper magnet is fixedly attached to the stem between the proximal-to-intermediate portions of the first and second grasper jaws.

28. The magnet-assisted suture grasper according to any one of clauses 19-27, wherein:
the second grasper jaw is reversibly moveable;
the actuator body is further connected to the second grasper jaw and configured for pivotal actuation of the second grasper jaw by movement of the handle;
translation of the actuator body within the stem lumen in the first direction causes the second grasper jaw to pivot away from the first grasper jaw, thereby further exposing the grasper magnet and allowing contact between the grasper magnet and a magnetic suture attracted thereto; and
translation of the actuator body within the stem lumen in the second direction causes the second grasper jaw to pivot toward the first grasper jaw, thereby contributing to sequestering the grasper magnet and grasping the magnetic suture within the recess.

29. The magnet-assisted suture grasper according to any one of clauses 19-28, wherein the distal ends of the first and second grasper jaws have sharp tips.

30. A system for passing a magnetic suture comprising:
the magnet-assisted suture grasper of any one of clauses 19-29; and
a magnetic suture comprising a suture magnet and a suture extending from the suture magnet.

31. A system for passing a magnetic suture comprising:
the magnet-assisted suture grasper of any one of clauses 19-29; and
a magnetic suture loop comprising a suture magnet and a bifurcated suture extending from the suture magnet and forming a suture loop.

32. The system according to clause 31, further comprising a cartridge tube, wherein:
the cartridge tube comprises a cartridge tube proximal opening, a cartridge tube distal opening, and a cartridge tube lumen therebetween;
the suture loop traverses the cartridge tube lumen based on having been inserted through the cartridge tube distal opening; and
the suture magnet is disposed outside of the cartridge tube lumen adjacent the cartridge tube distal opening.

What is claimed is:

1. A magnet-assisted suture grasper for grasping a magnetic suture comprising:
(a) a suture retrieval needle comprising a proximal end, a distal end, and a needle body extending therebetween, the needle body defining a needle body axis between the proximal and distal ends of the suture retrieval needle, the needle body having a proximal hole, a distal hole, and a needle lumen extending therebetween along the needle body axis;
(b) a retriever body disposed within the needle lumen and translatable therein along the needle body axis;
(c) a grasper arm comprising a proximal end, a proximal-to-intermediate portion, a distal portion, and a distal end, the grasper arm extending from the distal end of the retriever body and being reversibly moveable between a first position and a second position; and
(d) a grasper magnet being disposed adjacent the proximal-to-intermediate portion of the grasper arm, the magnet-assisted suture grasper sequestering the grasper magnet within the needle lumen when the grasper arm is in the first position and exposing the grasper magnet from the needle lumen when the grasper arm is in the second position, wherein:
the distal end of the grasper arm extends further distally than the grasper magnet,
translation of the retriever body within the needle lumen in a first direction along the needle body axis causes the grasper arm to move from the first position to the second position, thereby exposing the grasper magnet and allowing contact between the grasper magnet and a magnetic suture attracted thereto, and
translation of the retriever body within the needle lumen in a second direction opposite the first direction along the needle body axis causes the grasper arm to move from the second position to the first position, thereby sequestering the grasper magnet and grasping the magnetic suture within the needle lumen.

2. The magnet-assisted suture grasper according to claim 1, wherein the suture retrieval needle is straight, the needle body axis thereby being straight.

3. The magnet-assisted suture grasper according to claim 1, wherein the suture retrieval needle is curved, the needle body axis thereby being curved.

4. The magnet-assisted suture grasper according to claim 1, wherein the suture retrieval needle has a sharp tip.

5. The magnet-assisted suture grasper according to claim 1, wherein the grasper arm is integral to the retriever body.

6. The magnet-assisted suture grasper according to claim 1, wherein the grasper magnet is fixedly attached to the distal end of the retriever body, either directly or indirectly.

7. The magnet-assisted suture grasper according to claim 1, wherein the grasper magnet is fixedly attached to the grasper arm, either directly or indirectly, at the proximal-to-intermediate portion of the grasper arm.

8. The magnet-assisted suture grasper according to claim 1, further comprising a magnet wire having a proximal end and a distal end, wherein the proximal end of the magnet wire is fixedly disposed within the retriever body and the grasper magnet is fixedly attached to the distal end of the magnet wire, either directly or indirectly.

9. The magnet-assisted suture grasper according to claim 1, wherein:
the grasper arm further comprises an enlarged distal terminus at the distal end of the grasper arm;
the grasper arm is reversibly moveable between the first position and the second position based on translation of the grasper arm from inside of the needle lumen to outside of the needle lumen through the distal hole of the needle body; and
the enlarged distal terminus at the distal end of the grasper arm has a size sufficiently small to allow contact between the grasper magnet and a suture magnet of a magnetic suture attracted thereto when the grasper arm is in the second position and to allow a suture of the magnetic suture to pass when the grasper arm is in the first position, and sufficiently large to block the suture magnet of the magnetic suture from exiting the needle lumen through the distal hole of the needle body when the grasper arm is in the first position.

10. The magnet-assisted suture grasper according to claim 9, wherein the enlarged distal terminus comprises a hook.

11. The magnet-assisted suture grasper according to claim 1, wherein:
the grasper arm is a first grasper arm;
the magnet-assisted suture grasper further comprises a second grasper arm comprising a proximal end, a proximal-to-intermediate portion, a distal portion, and a distal end, the second grasper arm extending from the distal end of the retriever body and being reversibly moveable between the first position and the second position;
the first and second grasper arms are connected at their distal ends, thereby forming a grasper arm loop;
the grasper arm loop is reversibly moveable between the first position and the second position based on translation of the grasper arm loop from inside of the needle lumen to outside of the needle lumen through the distal hole of the needle body;
the grasper arm loop circumscribes an area sufficiently large to allow contact between the grasper magnet and a suture of a magnetic suture attracted thereto when the grasper arm loop is in the second position; and
the grasper arm loop has a thickness sufficiently great to block the suture magnet of the magnetic suture from exiting the needle lumen through the distal hole of the needle body when the grasper arm loop is in the first position.

12. The magnet-assisted suture grasper according to claim 1, wherein:
- the grasper arm is a first grasper arm;
- the magnet-assisted suture grasper further comprises a second grasper arm comprising a proximal end, a proximal-to-intermediate portion, a distal portion, and a distal end, the second grasper arm extending from the distal end of the retriever body and being reversibly moveable between the first position and the second position;
- the first and second grasper arms are connected at their distal ends, thereby forming a grasper arm loop;
- the first and second grasper arms further comprise an enlarged distal terminus at the distal ends of the first and second grasper arms;
- the grasper arm loop is reversibly moveable between the first position and the second position based on translation of the grasper arm loop from inside of the needle lumen to outside of the needle lumen through the distal hole of the needle body;
- the grasper arm loop circumscribes an area sufficiently large, and the enlarged distal terminus at the distal ends of the first and second grasper arms has a size sufficiently small, to allow contact between the grasper magnet and a suture magnet of a magnetic suture attracted thereto when the grasper arm loop is in the second position;
- the enlarged distal terminus at the distal ends of the first and second grasper arms has a size sufficiently small to allow a suture of the magnetic suture to pass when the grasper arm loop is in the first position; and
- the enlarged distal terminus at the distal ends of the first and second grasper arms has a size sufficiently large to block the suture magnet of the magnetic suture from exiting the needle lumen through the distal hole of the needle body when the grasper arm loop is in the first position.

13. A system for passing a magnetic suture comprising:
- the magnet-assisted suture grasper of claim 1; and
- a magnetic suture comprising a suture magnet and a suture extending from the suture magnet.

14. A system for passing a magnetic suture comprising:
- the magnet-assisted suture grasper of claim 1; and
- a magnetic suture loop comprising a suture magnet and a bifurcated suture extending from the suture magnet and forming a suture loop.

15. The system according to claim 14, further comprising a cartridge tube, wherein:
- the cartridge tube comprises a cartridge tube proximal opening, a cartridge tube distal opening, and a cartridge tube lumen therebetween;
- the suture loop traverses the cartridge tube lumen based on having been inserted through the cartridge tube distal opening; and
- the suture magnet is disposed outside of the cartridge tube lumen adjacent the cartridge tube distal opening.

* * * * *